(12) United States Patent
Boschert et al.

(10) Patent No.: US 7,217,687 B2
(45) Date of Patent: May 15, 2007

(54) USE OF OSTEOPONTIN FOR THE TREATMENT AND/OR PREVENTION OF NEUROLOGIC DISEASES

(75) Inventors: Ursula Boschert, Troinex (CH); Georg Feger, Thoiry (FR); Raghuram Selvaraju, Vandoeuvres (CH); Lilia Bernasconi, Perly (CH); Ruben Papoian, Cincinnati, OH (US)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 10/477,876

(22) PCT Filed: May 8, 2002

(86) PCT No.: PCT/EP02/05081

§ 371 (c)(1),
(2), (4) Date: Apr. 9, 2004

(87) PCT Pub. No.: WO02/092122

PCT Pub. Date: Nov. 21, 2002

(65) Prior Publication Data

US 2004/0235720 A1    Nov. 25, 2004

(30) Foreign Application Priority Data

May 17, 2001    (EP)    ................................... 01111296

(51) Int. Cl.
C07K 14/00    (2006.01)
(52) U.S. Cl. .......................................... 514/2; 530/351
(58) Field of Classification Search ................ 514/2; 530/351
See application file for complete search history.

(56) References Cited

FOREIGN PATENT DOCUMENTS

| WO | WO 00/37502 | 6/2000 |
|---|---|---|
| WO | WO 00/63241 | 10/2000 |
| WO | WO 00/64460 | 11/2000 |
| WO | WO 01/24831 | 4/2001 |

OTHER PUBLICATIONS

Ellison J. A. et al, "Matrix Remodeling After Stroke De Novo Expression of Matrix Proteins and Integrin Receptors", Annals of the New Yor Academy of Sciences, New York Academy of Sciences, New York, NY, US vol. 890, 1999, pp. 204-222 XP001029484.
Julie A. Ellison et al, "Osteopontin and its Integrin Receptor Alphavbeta3 are Upregulated During Formation of the Glial Scar After Focal Stroke", Stroke, American Heart Association, Dallas TX, US, vol. 29, No. 8, Aug. 1998, pp. 1698-1706, XP001029459.
Mun-Yong Lee et al, "Transient Upregulation of Osteopontin MRNA in Hippocampus and Striatum Following Global Forebrain Ischemia in Rats", Neuroscience Letters, Limerick, vol. 271, No. 2, 1999, pp. 81-84, XP001029474.
(Prevention of Relapses and Disability by Interferon @B-1A Subcutaneously in Multiple Sclerosis) Study Group P, "Randomised Double-Blind PlaceBlo-Controlled Study of Interferon Beta-1A in Relapsing/Remitting Multiple Sclerosis", vol. 352, No. 9139 Nov. 7, 1998, pp. 1498-1504, XP004265722.
Altschul S F et al, (1990) "Basic Local Alignment Search Tool" J Mol Biol. 215: 403-410.
Barres, B.A., and Raff, M.C. (Dec. 13, 1999). "Axonal Control Of Oligodendrocyte Development". Journal of Cell Biology. 147(6): 1123-1128.
Barres, B.A., et al. (1993). "Multiple Extracellular Signals Are Required For Long-Term Oligodendrocyte Survival". Development. 118(1): 283-295.
Bjartmar, C., et al (1999). "Axonal Pathology In Myelin Disorders". Journal of Neurocytology. 28: 383-395.
Breighton, B and Hayden, MR: S, (Feb. 21, 1981). "Huntington's Chorea" Afr Med J.; 59(8): 250.
Dal Canto, M.C., et al (1995). "Two Models Of Multiple Sclerosis: Experimental Allergic Encephalomyelitis (EAE) and Theiler's Murine Encephalomyelitis Virus (TMEV) Infection. A Pathological And Immunological Comparison". Microsc. Res. Tech. 32(3): 215-29.
Derynk R. et al., (1980). "Isolation And Structure Of A Human Fibroblast Interferon Gene" Nature 285: 542-547.
Devereux J et al, (1984). "A Comprehensive Set Of Sequence Analysis Programs For The VAX" Nucleic Acids Res, 12(1): 387-395.
Dubois-Dalcq, M., et al. (1999). "The Neurobiology Of X-Linked Adrenoleukodystrophy, A Demyelinating Peroxisomal Disorder". Trends in Neurosciences 22(1): 4-12.
Dubois-Dalcq, M., and Murray, K. (2000). "Why Are Growth Factors Important In Oligodendrocyte Physiology?" Pathol Biol (Paris) 48(1): 80-86,.
Fernández, P.A., et al. (2000). "Evidence That Axon-Derived Neuregulin Promotes Oligodendrocyte Survival In The Developing Rat Optic Nerve". Neuron 28(1): 81-90.
Franklin, R.J., and Hinks, G.L. (1999). "Understanding CNS Remyelination: Clues From Developmental And Regeneration Biology". Journal of Neurosciences Research 58(2): 207-213.
Grantham, (1974). "Amino Acid Difference Formula to Help Explain Protein Evolution", Science. 185: 862-864.
Grinspan, J.B., et al. (1996). "Re-Entry Into The Cell Cycle Is Required For Bfgf-Induced Oligodendroglial Dedifferentiation And Survival". Journal of Neuroscience Research. 46(4): 456-464.
Grinspan, J.B., et al (1993). "Trophic Effects Of Basic Fibroblast Growth Factor (bFGF) On Differentiated Oligodendroglia: A Mechanism For Regeneration Of The Oligodendroglial Lineage". Journal of Neuroscience Research. 36(6): 672-680.
Hajihosseini, M., et al (Dec. 15, 1996). "Origin Of Oligodendrocytes Within The Human Spinal Cord". Journal of Neuroscience. 16(24): 7981-7994.

(Continued)

Primary Examiner—Karen Cochrane Carlson
(74) Attorney, Agent, or Firm—Browdy and Neimark, PLLC

(57)    ABSTRACT

The invention relates to the use of osteopontin, or of an agonist of osteopontin activity, for treatment or prevention of a neurologic diseases.

19 Claims, 20 Drawing Sheets

OTHER PUBLICATIONS

Hartung, H.P., et al (1998). "Guillain-Barre Syndrome, CIDP And Other Chronic Immune-Mediated Neuropathies". Current Opinion in Neurology. 11: 497-513.

Hiremath, M.M., et al (1998). "Microglial/macrophage Accumulation During Cuprizone-Induced Demyelination in C57BL/6 Mice". Journal of Neuroimmunology. 92(1-2): 38-49.

Ichikawa H, et al (2000). "Osteopontin-Immunoreative Primary Sensory Neurons In The Rat Spinal And Trigeminal Nervous System", Brain Research. 863(1-2):276-281.

Jung, M., et al (1995). "Lines Of Murine Oligodendroglial Precursor Cells Immortalized By An Activated Neu Tyrosine Kinase Show Distinct Degrees Of Interaction With Axons In Vitro And In Vivo". European Journal of Neuroscience. 7(6): 1245-1265.

Kiefer et al. (Apr. 25, 1989). "The cDNA And Derived Amino Acid Sequence For Human Osteopontin". Nucleic Acids Res. 17(8):3306.

Kon S, et al (2000). "Antibodies To Different Peptides In Osteopontin Reveal Complexities In The Various Secreted Forms". Journal of Cellular Biochemistry. 77(3): 487-498.

Kon S, et al (2002). "Mapping Of Functional Epitopes Of Osteopontin By Monoclonal Antibodies Raised Against Defined Internal Sequences". Journal of Cellular Biochemistry. 84(2): 420-432.

Kunicki, T.J., et al (1997). "Molecular Determinants of arg-gly-asp Ligand Specificity for b3 Integrins". Journal of Biological Chemistry. 272(7): 4103-4107.

Lee, et al, (Aug. 20, 1999). "Transient Upregulation Of Osteopontin mRNA In Hippocampus And Striatum Following Global Forebrain Ischemia In Rats". Neuroscience Letters 271(2):81-84.

Lipton, S. A., and Rosenberg, P. A. (Mar. 3, 1994). "Excitatory Amino Acids As A Final Common Pathway For Neurologic Disorders". New England Journal of Medicine. 330: 613-22.

Loius, J.C., et al (1992). "CG-4 A New Bipontial Glial Cell Line From Rat Brain, Is Capable Of Differentiating In Vitro Into Either Mature Oligodendrocytes Or Type-2 Astrocytes". Journal of Neuroscience Research 31: 193-204.

Lubetzki, C., et al, (1993). "Even In Culture, Oligodendrocytes Myelinate Solely Axons". Proceedings of the National Academy of Sciences of the USA. 90:6820-6824.

Marchionni, M.A., et al, (1999). "Neuregulin In Neuron/Glial Interactions In The Central Nervous System. GGF2 Diminishes Autoimmune Demyelination, Promotes Oligodendrocyte Progenitor Expansion, And Enhances Remyelination". Advances in Experimental and Medical Biology. 468: 283-295.

Mark et al. (Sep. 1984). "Site-Specific Mutagenesis Of The Human Fibroblast Interferon Gene". Proc. Natl. Acad. Sci. USA., 81: 5662-5666.

Matthieu, J.M., et al, (1992). "Myelin Gene Expression During Demyelination And Remyelination In Aggregating Brain Cell Cultures". Journal of Neuroimmunology. 40(2-3): 231-234.

McDonald; J.W., et al, (1998). "Oligodendrocytes From Forebrain Are Highly Vulnerable To AMPA/kainate Receptor-Mediated Excitotoxicity". Nature Medicine. 4(3): 291-297.

Morell, P., et al, (1998). "Gene Expression In Brain During Cuprizone-Induced Demyelination And Remyelination". Molecular and Cellular Neurosciences. 12(4/5): 220-227.

Nait-Oumesmar, et al, (1999). "Progenitor Cells Of The Adult Mouse Subventricular Zone Proliferate, Migrate And Differentiate Into Oligodendrocytes After Demyelination". European Journal of Neuroscience. 11(12): 4357-4366.

Ng, W.P., et al, (1996). "Human Central Nervous System Myelin Inhibits Neurite Outgrowth". Brain Research. 720(1-2): 17-24.

Noseworthy, J.H. (1999). "Progress In Determining The Causes And Treatment Of Multiple Sclerosis". Nature. 399: A40-A47.

Oldberg et al., (Dec. 1986) "Cloning And Sequence Analysis Of Rat Bone Sialoprotein (Osteopontin) cDNA Reveals An Arg-Gly-Asp Cell-Binding Sequence". Proc Natl Acad Sci USA. 83(23):8819-8823.

Pantoni, L., et al, (1996). "Cerebral White Matter Is Highly Vulnerable To Ischemia". Stroke. 27(9): 1641-1646.

Pearson W R, (1990). "Rapid And Sensitive Sequence Comparison with FASTP and FASTA". Methods in Enzymology. 183, 63-99.

Pearson W R and Lipman D J, (Apr. 1988). "Improved Tools For Biological Sequence Comparison". Proc Nat Acad Sci USA. 85: 2444-2448.

Petry, K.G., et al, (2000). "Experimental Allergic Encephalomyelitis Animal Models For Analyzing Features Of Multiple Sclerosis". Pathologie Biologie. (Paris) 48(1): 47-53.

Pöhlau, D., et al, (1998). "Promoting Remyelination As A Future Therapeutic Principle In Multiple Sclerosis". Nervenarzt, 69, 841-850.

Prineas, J.W., et al, (1993). "Multiple Sclerosis: Remyelination Of Nascent Lesions". Annals of Neurology. 33(2): 137-151.

Rodriguez-Peña, A. (1999) "Oligodendrocyte Development And Thyroid Hormone". Journal of Neurobiology. 40(4): 497-512.

Rogister, B., et al, (1999). "From Neural Stem Cells To Myelinating Oligodendrocytes". Molecular and Cellular Neurosciences. 14(4-5): 287-300.

Sahrbacher, U.C., et al, (1998). "Mice With An Inactivation Of The Inducible Nitric Oxide Synthase Gene Are Susceptible To Experimental Autoimmune Encephalomyelitis". European Journal of Immunology 28(4): 1332-1338.

Saitoh Y, et al, (1995). "Expression Of Osteopontin In Human Glioma, Correlation With The Malignancy". Laboratory Investigations. 72(1): 55-63.

Scarlato, M., et al, (2000). "Analysis Of Oligodendroglial Differentiation Using cDNA Arrays". Journal of Neuroscience Research. 59(3): 430-5, 2000.

Scherer, Steven. (Jan. 1997). "Molecular Genetics Of Demyelination: New Wrinkles On An Old Membrane". Neuron. 18: 13-16.

Scolding, N., and Lassmann, H. (1996). "Demyelination and Remyelination". Trends in Neurosciences. 19(1): 1-2.

Shaw, C.E., et al, (1996). "Analysis Of Integrin Expression On Oligodendrocytes During Axo-Glial Interaction By Using Rat-Mouse Xenocultures". Journal of Neuroscience. 16(3): 1163-72.

Shin et al., (Oct. 1, 1999). "Expression Of Osteopontin mRNA In The Adult Rat Brain". Neuroscience Letters. 273(2):73-6.

Shepard H. M. et al., (1981). "A Single Amino Acid Change In IFN-$\beta_1$ Abolishes Its Antiviral Activity". Nature. 294: 563-565.

Sodek J, et al, (2000). "Osteopontin". Crit Rev Oral Biol Med. 11(3):279-303.

Smith, P.K., et al, (1985). "Measurement Of Protein Using Bicinchoninic Acid". Analytical Biochemistry. 150:76-85.

Smith, T. and Waterman (1981). "Identification of Common Molecular Subsequences". J Mol Biol. 147,195-197.

Storch, M.K., et al, (1998). "Multiple Sclerosis: In Situ Evidence For Antibody- And Complement-Mediated Demyelination". Annals of Neurology. 43(4): 465-71.

Trojaborg, W., (1998). "Acute And Chronic Neuropathies: New Aspects Of Guillain-Barre Syndrome And Chronic Inflammatory Demyelinating Polyneuropathy, An Overview And An Update". Electroencephalogrphy and Clinical Neurophysiology. 107: 303-316.

Trotter, J., et al, (1989), "Differentiation-Regulated Loss Of The Polysialylated Embryonic Form And Expression Of The Different Polypeptides Of The Neural Cell Adhesion Molecule By Cultured Oligodendrocytes And Myelin". Journal of Neuroscience Research 22(4): 369-83.

Wiechelman, K., et al, (1988). "Investigation Of The Bicinchoninic Acid Protein Assay: Identification Of The Groups Responsible For Color Formation". Analytical Biochemistry. 175, 231-237.

Whitney, L.W., et al, (1999). "Analysis Of Gene Expression In Multiple Sclerosis Lesions Using cDNA Microarrays". Annals of Neurology. 46(3): 425-428.

Arnett, H, et al, (Nov. 2001). "TNF α Promotes Proliferation Of Oligodendrocyte Progenitors And Remyelination". Nature Neuroscience. 4(11): 1116-1122.

Ashizawa, N, et al, (1996). "Osteopontin Is Produced By Rat Cardiac Fibroblasts And Mediates A(II)-Induced DNA Synthesis And Collagen Gel Contraction". J Clin Invest. 98: 2218-2227.

Ashkar, S, et al, (2000). "Eta-1 (osteopontin): An early Component Of Type-1 (Cell-Mediated) Immunity". Science. 287:860-864.

Barres, B, et al, (Jul. 10, 1992). "Cell-Death and Control of Cell-Survival in the Oligodendrocyte Lineage". Cell. 70: 31-46.

Baumann, N. and Pham-Dinh D (2001). "Biology Of Oligodendrocyte And Myelin In The Mammalian Central Nervous System". Physiological Reviews. 81(2): 871-927.

Blakemore, W., (1972). "Observations On Oligodendrocyte Degeneration, The Resolution Of Status Spongiosus And Remyelination In Cuprizone Intoxication In Mice". Journal of Neurocytology. 1: 413-426.

Blakemore, W., (1973). "Demyelination Of The Superior Cerebellar Peduncle In The Mouse Induced By Cuprizone". Journal of the Neurological Sciences. 20: 63-72.

Blaschuk, K., et al, (2000). "The Regulation Of Proliferation And Differentiation In Oligodendrocyte Progenitor Cells By αv Integrins". Development. 127: 1961-1969.

Bottenstein, J., and Sato G (1979). "Growth Of A Rat Neuroblastoma Cell Line In Serum-Free Supplemented Medium". Proc Natl Acad Sci USA. 76(1): 514-517.

Buttery PC, and ffrench-Constant C (1999). "Laminin-2/Integrin Interactions Enhance Myelin Membrane Formation By Oligodendrocytes". Molecular and Cellular Neuroscience. 14: 199-212.

Cardwell MC, and Rome LH (1988). "RGD-containing Peptides Inhibit The Synthesis Of Myelin-Like Membrane By Cultured Oligodendrocytes". J Cell Biol. 107: 1551-1559.

Carey, E.M., and Freeman N. (1983). "Biochemical Changes In Cuprizone-Induced Spongiform Encephalopathy. I. Changes In The Activities Of 2',3'-Cyclic Nucleotide 3'-Phosphohydrolase, Oligodendroglial Ceramide Galactosyl Transferase, And The Hydrolysis Of The Alkenyl Group Of Alkenyl, Acyl-Glycerophospholipids By Plasmalogenase In Different Regions Of The Brain". Neurochemical Research. 8(8): 1029-1044.

Chang, A., et al, (2000). "NG2-Positive Oligodendrocyte Progenitor Cells In Adult Human Brain And Multiple Sclerosis Lesions". Journal of Neuroscience. 20(17): 6404-6412.

Copelman, C., et al, (2001). "Myelin Phagocytosis And Remyelination Of Macrophage-Enriched Central Nervous System Aggregate Cultures". Journal of Neuroscience Research. 66: 1173-1178.

Corley, S., et al, (2001). "Astrocytes Attenuate Oligodendrocyte Death In Vitro Through An Alpha(6) Integrin-Laminin-Dependent Mechanism". GLIA. 36: 281-294.

Demerens, C., et al, (1999). "Eliprodil Stimulates CNS Myelination—New Prospects For Multiple Sclerosis?" Neurology. 52: 346-350.

Denhardt, DT, et al, (2001). "Role Of Osteopontin In Cellular Signaling And Toxicant Injury". Annual Review of Pharmacology and Toxicology. 41: 723-749.

Denhardt DT, and Noda M (1998). "Osteopontin Expression And Function: Role In Bone Remodeling". Journal of Cellular Biochemistry Suppleents. 30/31:92-102.

Diemel, LT, et al, (1998). "Macrophages in CNS Remyelination: Friend or Foe?" Neurochemical Research. 23(3): 341-347.

Dubois-Dalcq, M., and R. Armstrong (1990). "The Cellular and Molecular Events of Central-Nervous-System Remyelination". BioEssays. 12(12): 569-576.

Ellison JA, et al, (1999). "Matrix remodeling after stroke—De Novo expression of Matrix Proteins and Integrin Receptors". Neuroprotective Agents: Fourth International Conference. 890: 204-222.

Fawcett JW, and Asher RA (1999). "The Glial Scar And Central Nervous System Repair". Brain Research Bulletin. 49(6): 377-391.

Fok-Seang J, et al, (1998). "Cytokine-Induced Changes In The Ability Of Astrocytes To Support Migration Of Oligodendrocyte Precursors And Axon Growth". European Journal of Neuroscience. 10: 2400-2415.

Franklin, RJ, et al (1991). "Transplanted type-1 Astrocytes Facilitate Repair Of Demyelinating Lesions By Host Oligodendrocytes In Adult Rat Spinal Cord". Journal of Neurocytology. 20: 420-430.

Franklin, RJM, et al, (1999). "Magnetic Resonance Imaging Of Transplanted Oligodendrocyte Precursors In The Rat Brain". NeuroReport. 10: 3961-3965.

Frost, EE, et al (1999). "Integrins Mediate A Neuronal Survival Signal For Oligodendrocytes". Current Biology. 9: 1251-1254.

Gensert, J.M., and Goldman JE (Jul. 1997). "Endogenous Progenitors Remuelinate Demyelinated Axons In The Adult CNS". Neuron. 19: 197-203.

Gveric, D., et al (1999). "Insulin-like Growth Factors And Binding Proteins In Multiple Sclerosis Plaques". Neuropathology and Applied Neurobiology. 25: 215-225.

Helluin, O, et al (Jun. 16, 2000). "The Activation State of $α_vβ_3$ Regulates Platelet And Lymphocyte Adhesion To Intact And Thrombin-Cleaved Osteopontin". Journal of Biological Chemistry. 275(24): 18337-18343.

Horton, M.A. (1997). "The $α_vβ_3$ Integrin 'Vitronectin Receptor'". Int J Biochem Cell Biol. 29(5): 721-725.

Kopacek, J., et al, (Jan. 2000). "Upregulation Of The Genes Encoding Lysosomal Hydrolases, A Perforin-Like Protein, And Peroxidases In The Brains Of Mice Affected With An Experimental Prion Disease". Journal of Virology. 74(1): 411-417.

Lee, M., et al, (Sep. 18, 2001). "Expression Of Osteopontin mRNA In Developing Rat Brain". Cell Tissue Res. 306:179-185.

Levine, J.M., and R. Reynolds (1999). "Activation And Proliferation Of Endogenous Oligodendrocyte Precursor Cells During Ethidium Bromide-Induced Demyelination". Experimental Neurology. 160: 333-347.

Levine, J.M., et al (2001). "The Oligodendrocyte Precursor Cell In Health And Disease". Trends in Neurosciences. 24(1): 39-47.

Liaw L, et al (1998). "Altered Wound Healing In Mice Lacking A Functional Osteopontin Gene (spp1)". Journal of Clinical Investigation. 101(7): 1468-1478.

Loughlin, A.J. et al, (1997). "Myelination And Remyelination Of Aggregate Rat Brain Cell Cultures Enriched With Macrophages". Journal of Neuroscience Research. 47: 384-392.

Louis, J.C., et al (1992). "Cg-4, A New Bipotential Glial-Cell Line from Rat-Brain, Is Capable of Differentiating In Vitro Either Mature Oligodendrocytes Or Type-2 Astrocytes". Journal of Neuroscience Research. 31: 193-204.

Ludwin, S.K. (1978). "Central Nervous-System Demyelination and Remyelination in Mouse Ultrastructural-Study of Cuprizone Toxicity". Laboratory Investigation. 39(6): 597-612.

Ludwin, S.K. (1979). "Failure of Adequate Central Remyelination Following Long-Term Demyelination by Cuprizone". Journal of Neuropathology and Experimental Neurology. 38: 330, No. 88.

Mason, JL, et al (2000). "Mature Oligodendrocyte Apoptosis Precedes IGF-1 Production and Oligodendrocyte Progenitor Accumulation And Differentiation During Demyelination/Remyelination". Journal of Neuroscience Research. 61: 251-262.

Mason, J., et al (Sep. 15, 2001). "Interleukin-1β Promotes Repair of the CNS". Journal of Neuroscience. 21(18): 7046-7052.

Mason JL, et al (Aug. 1, 2000). "Insulin-like Growth Factor-1 Inhibits Mature Oligodendrocyte Apoptosis During Primary Demyelination". Journal of Neuroscience. 20: 5703-5708.

Matsushima, G., and P. Morell (2001). "The Neurotoxicant, Cuprizone, As A Model To Study Demyelination And Remyelination In The Central Nervous System". Brain Pathology. 11: 107-116.

Mayer, M., et al (1994). "Ciliary Neurotrophic Factor and Leukemia Inhibitory Factor Promote the Generation, Maturation and Survival of Oligodendrocytes In-Vitro". Development. 120: 143-153.

Mazzali, M., et al (2002). "Osteopontin—A Molecule For All Seasons". Q J Med-Monthly Journal of the Association of Physicians 95: 3-13.

McKinnon, R.D., et al (Nov. 1990). "FGF Modulates the PDGF-Driven Pathway of Oligodendrocyte Development". Neuron. 5: 603-614.

McMahon, E., et al (2001). "Absence of Macro-Phage-Inflammatory Protein-1α Delays Central Nervous System Demyelination In The Presence Of An Intact Blood-Brain Barrier". Journal of Immunology. 167:2964-2971.

McMorris, F.A., et al (1990). "Regulation Of Oligodendrocyte Development By Insulin-Like Growth Factors And Cyclic Nucleotides". Annals New York Academy of Sciences. 605: 101-109.

McMorris, F.A., et al(Feb. 1986). "Insulin-like Growth Factor I/somatomedin C: A Potent Inducer Of Oligodendrocyte Development". Proc Natl Acad Sci USA. 83: 822-826.

Meyer-Franke, A., et al (1999). "Astrocytes Induce Oligodendrocyte Processes To Align With And Adhere To Axons". Molecular and Cellular Neuroscience. 14: 385-397.

Miyachi, T, et al (2001). "Interleukin-β Induces The Expression Of Lipocortin 1 mRNA In Cultured Rat Cortical Astrocytes". Neuroscience Research. 40: 53-60.

Morell, P., et al (1998). "Gene Expression In Brain During Cuprizone-Induced Demyelination And Remyelination". Molecular and Cellular Neuroscience. 12: 220-227.

Murry, C.E., et al (1994). "Macrophages Express Osteopontin During Repair of Myocardial Necrosis". American Journal of Pathology. 145(6): 1450-1462.

Nam, T., et al (2000). "Thrombospondin And Osteopontin Bind To Insulin-Like Growth Factor (IGF)-Binding Protein-5 Leading To An Alteration In IGF-I-Stimulated Cell Growth". Endocrinology 141(3): 1100-1106.

Nishiyama, Akiko (Dec. 1998). "Glial Progenitor Cells In Normal And Pathological States". Keio J Med. 47(4): 205-208.

Nishiyama, Akiko (2001). "NG2 Cells In The Brain: A Novel Glial Cell Population". Human Cell. 14(1): 77-82.

Nishiyama, et al (1999). "NG2+ Glial Cells: A Novel Glial Cell Population In The Adult Brain". Journal of Neuropathology and Experimental Neurology. 58(11): 1113-1124.

Noble, M., et al (1995). "From Rodent Glial Precursor Cell To Human Glial Neoplasia In The Oligodendrocyte-Type-2 Astrocyte Lineage". GLIA. 15: 222-230.

O'Reilly, D.R. (1997). "Use Of Baculovirus Expression Vectors". Methods in Molecular Biology, vol. 62: Recombinant Gene Expression Protocols; R. Tuan Ed., Humana Press Inc., Totowa, NJ, Chapter 19, pp. 235-246.

Orentas, D., and R. Miller (1998). "Regulation of Oligodendrocyte Development". Molecular Neurobiology. 18: 247-259.

Padanilam, B., et al (1996). "Insulin-like Growth Factor I-Enhanced Renal Expression Of Osteopontin After Acute Ischemic Injury In Rats". Endocrinology. 137(5): No. 5, pp. 2133-2140.

Park, S., et al (2001). "Growth Factor Control of CNS Myelination". Developmental Neuroscience. 23: 327-337.

Pattison I., and Jean Jebbett (1973). "Clinical And Histological Recovery From The Scrapie-Like Spongiform Encephalopathy Produced In Mice By Feeding Them With Cuprizone". J Pathol. 109: 245-250.

Peireira LAV, et al (1996). "Biology Of The Repair Of Central Nervous System Demyelinated Lesions". Arquivos de Neuro-Psiquiatria. 54(2): 331-334.

Picard-Riera, Nathalie, et al, (Oct. 1, 2002). "Experimental Autoimmune Encephalomyelitis Mobilizes Neural Progenitors From the Subventricular Zone to Undergo Oligodendrogenesis in Adult Mice". PNAS. 99(20): 13211-13216.

Raff, M.C., et al, (Jun. 9, 1988). "Platelet-Derived Growth-Factor from Astrocytes Drives the Clock That Times Oligodendrocyte Development in Culture". Nature. 333: 562-565.

Redwine, J., and R. Armstrong (1998). "*In Vivo* Proliferation Of Oligodendrocyte Progenitors Expressing PDGF αR During Early Remyelination". Journal of Neurobiology. 37: 413-428.

Relvas, J.B., et al (2001). "Expression Of Dominant-Negative And Chimeric Subunits Reveals An Essential Role For β1 Integrin During Myelination". Current Biology. 11: 1039-1043.

Sakurai, Y., et al (1998). "Differentiation Of Oligodendrocyte Occurs In Contact With Astrocyte". Journal of Neuroscience Research. 52: 17-26.

Saris, C.J., et al, (Jul. 18, 1986). "The cDNA Sequence For The Protein-Tyrosine Kinase Substrate p36 (Calpactin I Heavy Chain) Reveals A Multidomain Protein With Internal Repeats". Cell. 46: 201-212.

Smith, Susan, (1996). "Lipocortin 1: glucocorticoids caught in the act?" Thorax. 51: 1057-1059.

Tanaka, F. et al, (2000). "Association of Osteopontin with Ischemic Axonal Death in Periventricular Leukomalacia". Acta Neuropathol. 100: 69-74.

Vabrick, I. and P. Shrager, (1998). "Ion Channel Redistribution And Function During Development Of The Myelinated Axon". Journal of Neurobiology. 37:80-96.

Wang, Xinkang, et al (1998). "Delayed Expression Of Osteopontin After Focal Stroke In The Rat". Journal of Neuroscience. 18(6): 2075-2083.

Weber, G.F. (2001). "The Metastasis Gene Osteopontin: A Candidate Target For Cancer Therapy". Biochimica et Biophysica Acta-Reviews on Cancer. 1552: 61-85.

Wolswijk, G., (1998). "Oligodendrocyte regeneration in the adult rodent CNS and the failure of this process in multiple sclerosis"; Neuronal Degeneration and Regeneration: from Basic Mechanisms to Prospects for Therapy. *Progress in Brain Research*. Van Leeuwen, et al, (Eds.). vol. 117, Chapter 18, pp. 233-247.

Yasuda, T., et al, (1995). "Apoptosis occurs in the oligodendroglial lineage, and is prevented by basic fibroblast growth factor". Journal of Neuroscience Research. 40: 306-317.

Denhardt, D., and Xiaojia Guo, (1993). "Osteopontin: A Protein with Diverse Functions". FASEB J. 7: 1475-1482.

Wolswijk, Guus, (2000), "Oligodendrocyte Survival, Loss and Birth in Lesions of Chronic-Stage Multiple Sclerosis", Brain. 123: 105-115.

Maeda, Y., et al (Jun. 2001). "Platelet-Derived Growth Factor-α Receptor Positive Oligodendroglia are Frequent in Multiple Sclerosis Lesions". Annals of Neurology. 49(6):776-785.

Weinstock-Guttman, B., and L. Jacobs (2000). "What is New in the Treatment of Multiple Sclerosis?" Drugs. 59(3): 401-410.

Fawcett JW et al "Peripheral nerve regeneration" Annu Rev Neurosci (1990) vol. 13, pp. 43-60.

Funakoshi H et al "Differential expression of mRNAs for neurotrophins and their receptors after axotomy of the sciatic nerve" J Cell Biol (1993) vol. 123, No. 2 pp.455-465.

| Development Cerebellum | osteop | MBP | PLP |
|---|---|---|---|
| C1 | 1 | 1 | 1 |
| C2 | 2 | 2 | 2 |
| C4 | 5 | 6 | 5 |
| C5 | 9 | 6 | 4 |
| C6 | 10 | 16 | 14 |
| C8 | 9 | ? | ? |
| C10 | 1 | 26 | 56 |
| C12 | 1 | 32 | 111 |
| C14 | 1 | 32 | 104 |
| C20 | 2 | 26 | 137 |
| CA | 3 | 9 | 39 |

|  | OPN E-coli | OPN Bac |
|---|---|---|
| 10 pM | 3.2% | 6.1% |
| 10 nM | 5.4% | 29.8% |
| 100 nM | ND | 14.8% |
| control | 1.4% | 1.4% |

Fig. 13

USE OF OSTEOPONTIN FOR THE TREATMENT AND/OR PREVENTION OF NEUROLOGIC DISEASES

This application is a national stage application of PCT/EP02/05081, filed May 8, 2002, which claims foreign priority to European application 01111296.8, filed May 17, 2001.

FIELD OF THE INVENTION

The present invention is generally in the field of neurologic diseases and disorders. It relates to neuroprotection, nerve myelination and generation or regeneration of myelin producing cells. In particular, it relates to demyelinating and neurodegenerative diseases, neuropathies, traumatic nerve injury, stoke and neurologic diseases caused by congenital metabolic disorders. More specifically, the present invention relates to the use of osteopontin, or of an agonist of osteopontin activity, for the manufacture of a medicament for treatment and/or prevention of a neurologic disease.

BACKGROUND OF THE INVENTION

Nerve myelination is an essential process in the formation and function of the central nervous system (CNS) and peripheral nervous system (PNS) compartments. The myelin sheath around axons is necessary for the proper conduction of electric impulses along nerves. Loss of myelin occurs in a number of diseases, among which are Multiple Sclerosis (MS) affecting the CNS, Guillain-Barre Syndrome, CIDP and others (see Abramsky and Ovadia, 1997; Trojaborg, 1998,Hartung et al, 1998). While of various etiologies, such as infectious pathogens or autoimmune attacks, demyelinating diseases all cause loss of neurologic function and may lead to paralysis and death. While present therapeutical agents reduce inflammatory attacks in MS and retards disease progression, there is a need to develop therapies that could lead to remyelination and recovery of neurologic function (Abramsky and Ovadia, 1997, Pohlau et al, 1998).

Injury to CNS induced by acute insults including trauma, hypoxia and ischemia can affect both neurons and white matter. Although most attention has been paid to processes leading to neuronal death, increasing evidence suggests that damage to oligodendrocytes, which myelinate axons, is also a specific component of CNS injury. Thus oligodendrocyte pathology was demonstrated at very early phase after-stroke (3 hours) in rats, suggesting that these cells are even more vulnerable to excitotoxic events than neuronal cells (Pantoni et al. 1996). One potential candidate mediating cell death is the marked elevation of glutamate concentration that accompanies many acute CNS injuries (Lipton et al. 1994). Indeed, beside neurons oligodendrocytes were also found to express functional glutamate receptors belonging to the AMPA/kainate subtype. Moreover oligodendrocytes display high vulnerability to glutamate application (McDonald et al. 1998).

Trauma is an injury or damage of the nerve. It may be spinal cord trauma, which is damage to the spinal cord that affects all nervous function that is controlled at and below the level of the injury, including muscle control and sensation, or brain trauma, such as trauma caused by closed head injury.

Cerebral hypoxia is a lack of oxygen specifically to the cerebral hemispheres, and more typically the term is used to refer to a lack of oxygen to the entire brain. Depending on the severity of the hypoxia, symptoms may range from confusion to irreversible brain damage, coma and death.

Stroke is usually caused by ischemia of the brain. It is also called cerebrovascular disease or accident. It is a group of brain disorders involving loss of brain functions that occur when the blood supply to any part of the brain is interrupted. The brain requires about 20% of the circulation of blood in the body. The primary blood supply to the brain is through 2 arteries in the neck (the carotid arteries), which then branch off within the brain to multiple arteries that each supply a specific area of the brain. Even a brief interruption to the blood flow can cause decreases in brain function (neurologic deficit). The symptoms vary with the area of the brain affected and commonly include such problems as changes in vision, speech changes, decreased movement or sensation in a part of the body, or changes in the level of consciousness. If the blood flow is decreased for longer than a few seconds, brain cells in the area are destroyed (infarcted) causing permanent damage to that area of the brain or even death.

A stroke affects about 4 out of 1,000 people. It is the 3rd leading cause of death in most developed countries, including the U.S. The incidence of stroke rises dramatically with age, with the risk doubling with each decade after age 35. About 5% of people over age 65 have had at least one stroke. The disorder occurs in men more often than women.

As mentioned above, a stroke involves loss of brain functions (neurologic deficits) caused by a loss of blood circulation to areas of the brain. The specific neurologic deficits may vary depending on the location, extent of the damage, and cause of the disorder. A stroke may be caused by reduced blood flow (ischemia) that results in deficient blood supply and death of tissues in that area (infarction). Causes of ischemic strokes are blood clots that form in the brain (thrombus) and blood clots or pieces of atherosclerotic plaque or other material that travel to the brain from another location (emboli). Bleeding (hemorrhage) within the brain may cause symptoms that mimic stroke.

The most common cause of a stroke is stroke secondary to atherosclerosis (cerebral thrombosis). Atherosclerosis ("hardening of the arteries") is a condition in which fatty deposits occur on the inner lining of the arteries, and atherosclerotic plaque (a mass consisting of fatty deposits and blood platelets) develops. The occlusion of the artery develops slowly. Atherosclerotic plaque does not necessarily cause a stroke. There are many small connections between the various brain arteries. If the blood flow gradually decreases, these small connections will increase in size and "by-pass" the obstructed area (collateral circulation). If there is enough collateral circulation, even a totally blocked artery may not cause neurologic deficits. A second safety mechanism within the brain is that the arteries are large enough that 75% of the blood vessel can be occluded, and there will still be adequate blood flow to that area of the brain.

A thrombotic stroke (stroke caused by thrombosis) is most common in elderly people, and often there is underlying atherosclerotic heart disease or diabetes mellitus. This type of stroke may occur at any time, including at rest. The person may or may not lose consciousness.

Strokes caused by embolism (moving blood clot) are most commonly strokes secondary to a cardiogenic embolism, clots that develop because of heart disorders that then travel to the brain. An embolism may also originate in other areas, especially where there is atherosclerotic plaque. The embolus travels through the bloodstream and becomes stuck in a small artery in the brain. This stroke occurs suddenly with immediate maximum neurologic deficit. It is not associated with activity levels and can occur at any time. Arrhythmias of the heart are commonly seen with this disorder and often are the cause of the embolus. Damage to the brain is often more severe than with a stroke caused by cerebral thrombosis. Consciousness may or may not be lost. The probable outcome is worsened if blood vessels damaged by stroke rupture and bleed (hemorrhagic stroke).

Peripheral Neuropathy is a syndrome of sensory loss, muscle weakness and atrophy, decreased deep tendon reflexes, and vasomotor symptoms, alone or in any combination.

The disease may affect a single nerve (mononeuropathy), two or more nerves in separate areas (multiple mononeuropathy), or many nerves simultaneously (polyneuropathy). The axon may be primarily affected (e.g. in diabetes mellitus, Lyme disease, or uremia or with toxic agents) or the myelin sheath or Schwann cell (e.g. in acute or chronic inflammatory polyneuropathy, leukodystrophies, or Guillain-Barré syndrome). Damage to small unmyelinated and myelinated fibers results primarily in loss of temperature and pain sensation; damage to large myelinated fibers results in motor or proprioceptive defects. Some neuropathies (e.g. due to lead toxicity, dapsone use, tick bite, porphyria, or Guillain-Barré syndrome) primarily affect motor fibers; others (e.g. due to dorsal root ganglionitis of cancer, leprosy, AIDS, diabetes mellitus, or chronic pyridoxine intoxication) primarily affect the dorsal root ganglia or sensory fibers, producing sensory symptoms. Occasionally, cranial nerves are also involved (e.g. in Guillain-Barré syndrome, Lyme disease, diabetes mellitus, and diphtheria). Identifying the modalities involved helps determine the cause.

Trauma is the most common cause of a localized injury to a single nerve. Violent muscular activity or forcible overextension of a joint may produce a focal neuropathy, as may repeated small traumas (e.g. tight gripping of small tools, excessive vibration from air hammers). Pressure or entrapment paralysis usually affects superficial nerves (ulnar, radial, peroneal) at bony prominences (e.g. during sound sleep or during anesthesia in thin or cachectic persons and often in alcoholics) or at narrow canals (e.g. in carpal tunnel syndrome). Pressure paralysis may also result from tumors, bony hyperostosis, casts, crutches, or prolonged cramped postures (e.g. in gardening). Hemorrhage into a nerve and exposure to cold or radiation may cause neuropathy. Mononeuropathy may result from direct tumor invasion.

Multiple mononeuropathy is usually secondary to collagen vascular disorders (e.g. polyarteritis nodosa, SLE, Sjögren's syndrome, RA), sarcoidosis, metabolic diseases (e.g. diabetes, amyloidosis), or infectious diseases (e.g. Lyme disease, HIV infection). Microorganisms may cause multiple mononeuropathy by direct invasion of the nerve (e.g. in leprosy).

Polyneuropathy due to acute febrile diseases may result from a toxin (e.g. in diphtheria) or an autoimmune reaction (e.g. in Guillain-Barré syndrome); the polyneuropathy that sometimes follows immunizations is probably also autoimmune.

Toxic agents generally cause polyneuropathy but sometimes mononeuropathy. They include emetine, hexobarbital, barbital, chlorobutanol, sulfonamides, phenytoin, nitrofurantoin, the vinca alkaloids, heavy metals, carbon monoxide, triorthocresyl phosphate, orthodinitrophenol, many solvents, other industrial poisons, and certain AIDS drugs (e.g. zalcitabine, didanosine).

Nutritional deficiencies and metabolic disorders may result in polyneuropathy. B vitamin deficiency is often the cause (e.g. in alcoholism, beriberi, pernicious anemia, isoniazid-induced pyridoxine deficiency, malabsorption syndromes, and hyperemesis gravidarum). Polyneuropathy also occurs in hypothyroidism, porphyria, sarcoidosis, amyloidosis, and uremia. Diabetes mellitus can cause sensorimotor distal polyneuropathy (most common), multiple mononeuropathy, and focal mononeuropathy (e.g. of the oculorrotor or abducens cranial nerves).

Malignancy may cause polyneuropathy via monoclonal gammopathy (multiple myeloma, lymphoma), amyloid invasion, or nutritional deficiencies or as a paraneoplastic syndrome.

Specific mononeuropathies: Single and multiple mononeuropathies are characterized by pain, weakness, and paresthesias in the distribution of the affected nerve. Multiple mononeuropathy is asymmetric; the nerves may be involved all at once or progressively. Extensive involvement of many nerves may simulate a polyneuropathy.

Ulnar nerve palsy is often caused by trauma to the nerve in the ulnar groove of the elbow by repeated leaning on the elbow or by asymmetric bone growth after a childhood fracture (tardy ulnar palsy). The ulnar nerve can also be compressed at the cubital tunnel. Paresthesias and a sensory deficit in the 5th and medial half of the 4th fingers occur; the thumb adductor, 5th finger abductor, and interossei muscles are weak and atrophied. Severe chronic ulnar palsy produces a clawhand deformity. Nerve conduction studies can identify the site of the lesion. Conservative treatment should be attempted before surgical repair is attempted.

The carpal tunnel syndrome results from compression of the median nerve in the volar aspect of the wrist between the transverse superficial carpal ligament and the longitudinal tendons of forearm muscles that flex the hand. It may be unilateral or bilateral. The compression produces paresthesias in the radial-palmar aspect of the hand and pain in the wrist and palm; sometimes pain occurs proximally to the compression site in the forearm and shoulder. Pain may be more severe at night. A sensory deficit in the palmar aspect of the first three fingers may follow; the muscles that control thumb abduction and opposition may become weak and atrophied. This syndrome should be distinguished from C-6 root compression due to cervical radiculopathy.

Peroneal nerve palsy is usually caused by compression of the nerve against the lateral aspect of the fibular neck. It is most common in emaciated bedridden patients and in thin persons who habitually cross their legs. Weakness of foot dorsiflexion and eversion (footdrop) occur. Occasionally, a sensory deficit occurs over the anterolateral aspect of the lower leg and dorsum of the foot or in the web space between the 1st and 2nd metatarsals. Treatment is usually conservative for compressive neuropathies (e.g. avoiding leg crossing). Incomplete neuropathies are usually followed clinically and usually improve spontaneously. If recovery does not occur, surgical exploration may be indicated.

Radial nerve palsy (Saturday night palsy) is caused by compression of the nerve against the humerus, e.g. as the arm is draped over the back of a chair during intoxication or deep sleep. Symptoms include weakness of wrist and finger extensors (wristdrop) and, occasionally, sensory loss over the dorsal aspect of the 1st dorsal interosseous muscle. Treatment is similar to that of compressive peroneal neuropathy.

Polyneuropathies are relatively symmetric, often affecting sensory, motor, and vasomotor fibers simultaneously. They may affect the axon cylinder or the myelin sheath and, in either form, may be acute (e.g. Guillain-Barré syndrome) or chronic (e.g. renal failure).

Polyneuropathy due to metabolic disorders (e.g. diabetes mellitus) or renal failure develops slowly, often over months or years. It frequently begins with sensory abnormalities in the lower extremities that are often more severe distally than proximally. Peripheral tingling, numbness, burning pain, or deficiencies in joint proprioception and vibratory sensation are often prominent. Pain is often worse at night and may be aggravated by touching the affected area or by temperature changes. In severe cases, there are objective signs of sensory loss, typically with stocking-and-glove distribution. Achilles and other deep tendon reflexes are diminished or absent. Painless ulcers on the digits or Charcot's joints may develop when sensory loss is profound. Sensory or proprioceptive deficits may lead to gait abnormalities. Motor involvement results in distal muscle weakness and atrophy. The autonomic nervous system may be additionally or selectively involved, leading to nocturnal diarrhea, urinary and fecal incontinence, impotence, or postural hypotension. Vasomotor symptoms vary. The skin may be paler and drier than normal, sometimes with dusky discoloration; sweating may be excessive. Trophic changes (smooth and shiny skin, pitted or ridged nails, osteoporosis) are common in severe, prolonged cases.

Nutritional polyneuropathy is common among alcoholics and the malnourished. A primary axonopathy may lead to secondary demyelination and axonal destruction in the longest and largest nerves. Whether the cause is deficiency of thiamine or another vitamin (e.g. pyridoxine, pantothenic acid, folic acid) is unclear. Neuropathy due to pyridoxine deficiency usually occurs only in persons taking isoniazid for TB; infants who are deficient or dependent on pyridoxine may have convulsions. Wasting and symmetric weakness of the distal extremities is usually insidious but can progress rapidly, sometimes accompanied by sensory loss, paresthesias, and pain. Aching, cramping, coldness, burning, and numbness in the calves and feet may be worsened by touch. Multiple vitamins may be given when etiology is obscure, but they have no proven benefit.

Uncommonly, an exclusively sensory polyneuropathy begins with peripheral pains and paresthesias and progresses centrally to a loss of all forms of sensation. It occurs as a remote effect of carcinoma (especially bronchogenic), after excessive pyridoxine ingestion (>0.5 g/day), and in amyloidosis, hypothyroidism, myeloma, and uremia. The pyridoxine-induced neuropathy resolves when pyridoxine is discontinued.

Hereditary neuropathies are classified as sensorimotor neuropathies or sensory neuropathies. Charcot-Marie-Tooth disease is the most common hereditary sensorimotor neuropathy. Less common sensorimotor neuropathies begin at birth and result in greater disability. In sensory neuropathies, which are rare, loss of distal pain and temperature sensation is more prominent than loss of vibratory and position sense. The main problem is pedal mutilation due to pain insensitivity, with frequent infections and osteomyelitis.

Hereditary motor and sensory neuropathy types I and II (Charcot-Marie-Tooth disease, peroneal muscular atrophy) is a relatively common, usually autosomal dominant disorder characterized by weakness and atrophy, primarily in peroneal and distal leg muscles. Patients may also have other degenerative diseases (e.g. Friedreich's ataxia) or a family history of them. Patients with type I present in middle childhood with footdrop and slowly progressive distal muscle atrophy, producing "stork legs." Intrinsic muscle wasting in the hands begins later. Vibration, pain, and temperature sensation decreases in a stocking-glove pattern. Deep tendon reflexes are absent. High pedal arches or hammer toes may be the only signs in less affected family members who carry the disease. Nerve conduction velocities are slow, and distal latencies prolonged. Segmental demyelination and remyelination occur. Enlarged peripheral nerves may be palpated. The disease progresses slowly and does not affect life span. Type II disease evolves more slowly, with weakness usually developing later in life. Patients have relatively normal nerve conduction velocities but low amplitude evoked potentials. Biopsies show wallerian degeneration.

Hereditary motor and sensory neuropathy type III (hypertrophic interstitial neuropathy, Dejerine-Sottas disease), a rare autosomal recessive disorder, begins in childhood with progressive weakness and sensory loss and absent deep tendon reflexes. Initially, it resembles Charcot-Marie-Tooth disease, but motor weakness progresses at a faster rate. Demyelination and remyelination occur, producing enlarged peripheral nerves and onion bulbs seen on nerve biopsy.

The characteristic distribution of motor weakness, foot deformities, family history, and electrophysiologic abnormalities confirm the diagnosis. Genetic analysis is available, but no specific treatment. Vocational counseling to prepare young patients for disease progression may be useful. Bracing helps correct footdrop; orthopedic surgery to stabilize the foot may help.

Neurodegenerative diseases comprise, among others, Alzheimer's disease, Parkinson's disease, Huntington's disease and Amyotrophic Lateral Sclerosis (ALS).

Alzheimer's disease is a disorder involving deterioration in mental functions resulting from changes in brain tissue. This includes shrinking of brain tissues, not caused by disorders of the blood vessels, primary degenerative dementia and diffuse brain atrophy. Alzheimer's disease is also called senile dementia/Alzheimer's type (SDAT). It is the most common cause of intellectual decline with aging. The incidence is approximately 9 out of 10,000 people. This disorder affects women slightly more often than men and occurs primarily in older individuals.

The cause is unknown. The neurochemical factors which may participate in generation of the disease include lack of the substances used by the nerve cells to transmit nerve impulses (neurotransmitters), including acetylcholine, somatostatin, substance P, and norepinephrine. Environmental factors include exposure to aluminum, manganese, and other substances. The infectious factors include prion (virus-like organisms) infections that affect the brain and spinal cord (central nervous system). In some families (representing 5 to 10% of cases) there is an inherited predisposition to development of the disorder, but this does not follow strict (Mendelian) patterns of inheritance. The diagnosis is usually made by ruling out other causes of dementia.

Researchers have found that in families that have multiple members with Alzheimer's, there is a particular gene variation which is common to all of those with the disease. The gene, which produces a substance called apolipoprotein E4, is not said to cause the disease, it's presence simply increases the chances that the disease may eventually occur. There are many people who have the E4 gene and never become afflicted with Alzheimer's.

The onset is characterized by impaired memory, with progressive loss of intellectual function. There may be mood changes, changes in language capability, changes in gait, and other changes as the disorder progresses. There is a decrease in the size (atrophy) of the tissues of the brain, enlargement of the ventricles (the spaces within the brain), and deposits within the tissues of the brain.

Parkinsons's disease is a disorder of the brain characterized by shaking and difficulty with walking, movement, and coordination. The disease is associated with damage to a part of the brain that controls muscle movement. It is also called paralysis agitans or shaking palsy.

The disease affects approximately 2 out of 1,000 people, and most often develops after age 50. It affects both men and women and is one of the most common neurologic disorders of the elderly. The term "parkinsonism" refers to any condition that involves a combination of the types of changes in movement seen in Parkinson's disease, which happens to be the most common condition causing this group of symptoms. Parkinsonism may be caused by other disorders or by external factors (secondary parkinsonism).

Parkinson's disease is caused by progressive deterioration of the nerve cells of the part of the brain that controls muscle movement (the basal ganglia and the extrapyramidal area). Dopamine, which is one of the substances used by cells to transmit impulses (transmitters), is normally produced in this area. Deterioration of this area of the brain reduces the amount of dopamine available to the body. Insufficient dopamine disturbs the balance between dopamine and other transmitters, such as acetylcholine. Without dopamine, the nerve cells cannot properly transmit messages, and this results in the loss of muscle function. The exact reason that the cells of the brain deteriorate is unknown. The disorder may affect one or both sides of the body, with varying degrees of loss of function.

In addition to the loss of muscle control, some people with Parkinson's disease become severely depressed. Although early loss of mental capacities is uncommon, with severe Parkinson's the person may exhibit overall mental deterioration (including dementia, hallucinations, and so on). Dementia can also be a side effect of some of the medications used to treat the disorder.

Huntington's Disease is an inherited, autosomal dominant neurologic disease. It is uncommon, affecting approximately 1 in 10000 individuals (Breighton and Hayden 1981). The disease does not usually become clinically apparent until the fifth decade of life, and results in psychiatric disturbance, involuntary movement disorder, and cognitive decline associated with inexorable progression to death, typically 17 years following onset.

The gene responsible for Huntington's disease is called huntingtin. It is located on chromosome 4p, presenting an effective means of preclinical and antenatal diagnosis. The genetic abnormality consists in an excess number of tandemly repeated CAG nucleotide sequences.

The increase in size of the CAG repeat in persons with Huntington's disease shows a highly significant correlation with age of onset of clinical features. This association is particularly striking for persons with juvenile onset Huntington's disease who have very significant expansion, usually beyond 50 repeats. The CAG repeat length in Huntington's disease families does exhibit some instability that is particularly marked when children inherit the huntingtin gene from affected fathers.

In HD, it is not known how this widely, expressed gene, results in selective neuronal death. Further, sequence analysis revealed no obvious homology to other known genes and no structural motifs or functional domains were identified which clearly provide insights into its function. In particular, the question of how these widely expressed genes cause selective neuronal death remains unanswered.

Amyptrophic Lateral Sclerosis, ALS, is a disorder causing progressive loss of nervous control of voluntary muscles because of destruction of nerve cells in the brain and spinal cord. Amyotrophic Lateral Sclerosis, also called Lou Gehrig's disease, is a disorder involving loss of the use and control of muscles. The nerves controlling these muscles shrink and disappear, which results in loss of muscle tissue due to the lack of nervous stimulation. Muscle strength and coordination decreases, beginning with the voluntary muscles (those under conscious control, such as the muscles of the arms and legs). The extent of loss of muscle control continues to progress, and more and more muscle groups become involved. There may be a loss of nervous stimulation to semi-voluntary muscles, such as the muscles that control breathing and swallowing. There is no effect on ability to think or reason. The cause is unknown.

ALS affects approximately 1 out of 100,000 people. It appears in some cases to run in families. The disorder affects men more often than women. Symptoms usually do not develop until adulthood, often not until after age 50.

Traumatic nerve injury may concern the CNS or the PNS. Traumatic brain injury (TBI), also simply called head injury or closed head injury (CHI), refers to an injury where there is damage to the brain because of an external blow to the head. It mostly happens during car or bicycle accidents, but may also occur as the result of near drowning, heart attack, stroke and infections. This type of traumatic brain injury would usually result due to the lack of oxygen or blood supply to the brain, and therefore can be referred to as an "anoxic injury".

Brain injury or closed head injury occurs when there is a blow to the head as in a motor vehicle accident or a fall. In this case, the skull hits a stationary object and the brain, which is inside the skull, turns and twists on its axis (the brain stem), causing localised or widespread damage. Also, the brain, a soft mass surrounded by fluid that allows it to "float," may rebound against the skull resulting in further damage.

There may be a period of unconsciousness immediately following the trauma, which may last minutes, weeks or months. Due to the twisting and rebounding, the traumatically brain injured patient usually receives damage or bruising to many parts of the brain. This is called diffuse damage, or "non-missile injury" to the brain. The types of brain damages occurring in non-missile injuries may be classified as either primary or secondary.

Primary brain damage occurs at the time of injury, mainly at the sites of impact, in particular when a skull fraction is present. Large contusions may be associated with an intracerebral hemorrhage, or accompanied by cortical lacerations. Diffuse axonal injuries occur as a result of shearing and tensile strains of neuronal processes produced by rotational movements of the brain within the skull. There may be small hemorrhagic lesions or diffuse damage to axons, which can only be detected microscopically.

Secondary brain damage occurs as a result of complications developing after the moment of injury. They include intracranial hemorrhage, traumatic damage to extracerebral arteries, intracranial herniation, hypoxic brain damage or meningitis.

An open head injury is a visible assault to the head and may result from a gunshot wound, an accident or an object going through the skull into the brain ("missile injury to the brain"). This type of head injury is more likely to damage a specific area of the brain.

So called mild brain injury may occur with no loss of consciousness and possibly only a dazed feeling or confused state lasting a short time. Although medical care administered may be minimal, persons with brain injury without coma may experience symptoms and impairments similar to those suffered by the survivor of a coma injury.

In response to the trauma, changes occur in the brain which require monitoring to prevent further damage. The brain's size frequently increases after a severe head injury. This is called brain swelling and occurs when there is an increase in the amount of blood to the brain. Later in the illness water may collect in the brain which is called brain edema. Both brain swelling and brain edema result in excessive pressure in the brain called intracranial pressure ("ICP").

Spinal cord injuries account for the majority of hospital admissions for paraplegia and tetraplegia. Over 80% occur as a result of road accidents. Two main groups of injury are recognised clinically: open injuries and closed injuries.

Open injuries cause direct trauma of the spinal cord and nerve roots. Perforating injuries can cause extensive disruption and hemorrhage. Closed injuries account for most spinal injuries and are usually associated with a fracture/dislocation of the spinal column, which is usually demonstrable radiologically. Damage to the cord depends on the extent of the bony injuries and can be considered in two main stages: Primary damage, which are contusions, nerve fibre transections and hemorrhagic necrosis, and secondary damage, which are extradural heamatoma, infarction, infection and edema.

Late effects of cord damage include: ascending and descending anterograde degeneration of damaged nerve fibers, post-traumatic syringomelyia, and systemic effects of paraplegia, such as urinary tract and chest infections, pressure sores and muscle wasting.

Neurologic disorders may further be due to congenital metabolic disorders. Myelin sheaths, which cover many nerve fibers, are composed of lipoprotein layers formed in early life. Myelin formed by the oligodendroglia in the CNS differs chemically and immunologically from that formed by the Schwann cells peripherally, but both types have the same function: to promote transmission of a neural impulse along an axon.

Many congenital metabolic disorders (e.g. phenylketonuria and other aminoacidurias; Tay-Sachs, Niemann-Pick, and Gaucher's diseases; Hurler's syndrome; Krabbe's disease and other leukodystrophies) affect the developing myelin sheath, mainly in the CNS. Unless the biochemical defect can be corrected or compensated for, permanent, often widespread, neurologic deficits result.

For instance, Krabbe disease or globoid cell leukodystrophy is a disorder involving the white matter of the peripheral and central nervous systems. Mutations in the gene for the lysosomal enzyme galactocerebrosidase (GALC) result in low enzymatic activity and decreased ability to degrade galactolipids found almost exclusively in myelin. Continued myelination and/or remyelination in patients requires functional endogenous oligodendrocytes or transplantation of normal oligodendrocytes or stem cells that can differentiate into oligodendrocytes, in order to provide for sufficient GALC expression (Wenger et al., 2000).

Neurofibromatosis 1 (NF1) is a common autosomal disorder with a wide range of neurologic manifestations.

Multiple system atrophy is a sporadic, adult-onset neurodegenerative disease of unknown etiology. The condition may be unique among neurodegenerative diseases by the prominent, if not primary, role played by the oligodendroglial cell in the pathogenetic process. The major difference to Parkinson's disease is that MSA patients do not respond to L-dopa treatment.

Demyelination in later life is a feature of many neurologic disorders; it can result from damage to nerves or myelin due to local injury, ischemia, toxic agents, or metabolic disorders. There is also evidence that demyelination may contribute to schizophrenia. Extensive myelin loss is usually followed by axonal degeneration and often by cell body degeneration, both of which may be irreversible. However, remyelination occurs in many instances, and repair, regeneration, and complete, recovery of neural function can be rapid. Central demyelination (ie, of the spinal cord, brain, or optic nerves) is the predominant finding in the primary demyelinating diseases, whose etiology is unknown. The most well known is MS.

Acute disseminated encephalomyelitis, postinfectious encephalomyelitis is characterized by perivascular CNS demyelination, which can occur spontaneously but usually follows a viral infection or viral vaccination (or, very rarely, bacterial vaccination), suggesting an immunologic cause. Acute inflammatory peripheral neuropathies that follow a viral vaccination or the Guillain-Barré syndrome are similar demyelinating disorders with the same presumed immunopathogenesis, but they affect only peripheral structures.

Metachromatic leukodystrophy is another demyelinating disease. Adrenoleukodystrophy and adrenomyeloneuropathy are rare X-linked recessive metabolic disorders characterized by adrenal gland dysfunction and widespread demyelination of the nervous system. Adrenoleukodystrophy occurs in young boys; adrenomyeloneuropathy, in adolescents. Mental deterioration, spasticity, and blindness may occur. Adrenoleukodystrophy is invariably fatal. Dietary and immunomodulatory treatments are under study.

Leber's hereditary optic atrophy and related mitochondrial disorders are characterized primarily by bilateral loss of central vision, usually affecting young men in their late teens or early twenties. Leber's hereditary optic atrophy can resemble the optic neuritis in MS. Mutations in the maternally inherited mitochondrial DNA have been identified.

HTLV-associated myelopathy, a slowly progressive spinal cord disease associated with infection by the human T-cell lymphotrophic virus, is characterized by spastic weakness of both legs.

Further neurologic disorders comprise neuropathies with abnormal myelination, an overview of which is given below.

Immune: Acute, Guillain Barré, Chronic, Chronic Immune Demyelinating Polyneuropathy (CIDP), Multifocal CIDP, Multifocal Motor Neuropathy (MMN), Anti-MAG Syndrome, GALOP Syndrome, Anti-Sulfatide Antibody Syndrome (with serum M-protein), Anti-GM2 antibody syndrome, POEMS Syndrome, Polyneuropathy Organomegaly, Endocrinopathy or Edema, M-protein, Skin changes, Perineuritis, IgM anti-GD1b antibody syndrome (occasional).

Toxins: Diphtheria, Buckthorn, Hexachlorophene, Sodium Cyanate, Tellurium.

Drugs: Predominantly demyelinating: Chloroquine, FK506 (Tacrolimus), Perhexiline, Procainamide, Zimeldine; Mixed demyelinating & axonal: Amiodarone, Eosinophilia-Myalgia syndrome, Gold, Suramin, Taxol.

Hereditary: Carbohydrate-deficient glycoprotein, Cataracts & Facial dysmorphism, Cockayne's syndrome, Congenital hypomyelinating, Congenital muscular dystrophy: Merosin deficient, Farber's disease (Lipogranulomatosis), HMSN & CMT, Dominant: IA, IB, III, HNPP, EGR2, Thermosensitive, Recessive: III (Dejerine-Sottas); 4A; 4B; 4B2; 4C; 4D (LOM); 4E; 4F; HMSN-R; CNS, X-linked: IX, Krabbe, Marinesco-Sjögren, Metachromatic Leukodystrophy, Niemann-Pick, Pelizaeus-Merzbacher (PLP), Refsum, Prion protein (PrP27-30): Glu200Lys mutation, Creutzfeld-Jakob disease, Mouse model: Prion over expression, Salla disease, SOX10, Tenascin-XA, Uneven packing of peripheral myelin sheaths, Ehlers-Danlos phenotype.

Metabolic (unusual): Diabetes (due to concurrent CIDP), Hypothyroidism, Hepatic disorders.

Mitochondrial: MNGIE Syndrome, Myopathy & external ophthalmoplegia, neuropathy, Gastro-Intestinal Encephalopathy, NARP Syndrome, Neuropathy, Ataxia, Retinitis, Pigmentosa.

Infections: Creutzfeld-Jakob disease, Diphtheria, HIV: Associated CIDP, Leprosy: Lepromatous; Mixed axonal-demyelinating; Colonized Schwan cells, Variant Creutzfeld-Jakob disease.

Further details can be taken from the following internet-site: www.neuro.wustl.edu/neuromuscular/nother/myelin.html.

Multiple Sclerosis (MS) is an inflammatory demyelinating disease of the central nervous system (CNS) that takes a relapsing-remitting or a progressive course. MS is not the only demyelinating disease. Its counterpart in the peripheral nervous system (PNS) is chronic inflammatory demyelinating polyradiculoneuropathy (CIDP). In addition, there are acute, monophasic disorders, such as the inflammatory demyelinating polyradiculoneuropathy termed Guillain-Barré syndrome (GBS) in the PNS, and acute disseminated encephalomyelitis (ADEM) in the CNS. Both MS and GBS are heterogeneous syndromes. In MS different exogenous assaults together with genetic factors can result in a disease course that finally fulfils the diagnostic criteria. In both diseases, axonal damage can add to a primarily demyelinating lesion and cause permanent neurologic deficits.

MS is the most common of the above demyelinating diseases. It is characterized as an autoimmune disorder, in which leukocytes of the immune system launch an attack on the white matter of the central nervous system (CNS). The grey matter may also be involved. Although the precise etiology of MS is not known, contributing factors may include genetic, bacterial and viral infection. In its classic manifestation (85% of all cases), it is characterized by alternating relapsing/remitting phases, which correspond to episodes of neurologic dysfunction lasting several weeks followed by substantial or complete recovery (Noseworthy, 1999). Periods of remission grow shorter over time. Many patients then enter a final disease phase characterized by gradual loss of neurologic function with partial or no recovery. This is termed secondary progressive MS. A small proportion (~15% of all MS patients) suffers a gradual and uninterrupted decline in neurologic function following onset of the disease (primary progressive MS). There is currently no clear curative treatment for the severest forms of MS, which are generally fatal.

The basic hallmark of MS is the demyelinated plaque with reactive glial scar formation, seen in the white matter tracts of the brain and spinal cord. Demyelination is linked to functional reduction or blockage in neural impulse conduction. Axonal transection and death is also observed in MS patients (Bjartmar et al., 1999). Pathological studies show the majority of involvement limited to the optic nerves, periventricular white matter, brain stem and spinal cord (Storch et al., 1998). The effects of these CNS deficiencies include the acute symptoms of diplopia, numbness and unsteady gait, as well as chronic symptoms such as spastic paraparesis and incontinence.

Molecular mechanisms underlying MS pathogenesis appear to stem from genetic and environmental factors, including viral and bacterial infections. These mechanisms promote increased migration of T lymphocytes and macrophages across the blood-brain barrier and into CNS tissue.

Demyelination is caused by attacks on myelin by activated macrophages and microglia, as well as damage to myelinating cells stemming from Fas-ligand signaling and complement- or antibody-mediated cytotoxicity. Therefore, demyelination occurs through both a direct attack on the myelin sheaths as well as elimination of the cells that produce and maintain myelin.

Genetic and environmental elements lead to an increased influx of inflammatory cells across the blood-brain barrier. This results in the increased migration of autoreactive T lymphocytes and macrophages into CNS tissue. Cytokine secretion by T cells activates antigen-presenting cells (APCs). When autoreactive T cells in the context of MHC class II molecules on APCs encounter putative 'MS antigens', often protein constituents of the myelin sheath, they may become activated. Several subsequent mechanisms can then act to damage oligodendrocytes and myelin. Complement- and antibody-mediated cytotoxicity may cause the majority of damage in some patients, while Fas-ligand signaling, and release of pro-inflammatory cytokines like TNF-$\alpha$ by CD4+ T cells may attack white matter in others. Activated macrophages may also play a role through enhanced phagocytosis and factor secretion. This causes widespread demyelination and, subsequent loss of conduction efficiency among the axons of the CNS. Subsequent repair mechanisms can, however, give rise to remyelination once the inflammatory process is resolved. The remyelinated axons of MS patients are recognized pathologically by the thin appearance of the sheaths around the remyelinated axons. Additional sodium channels are often found inserted into the demyelinated axonal membrane, compensating for the loss of conduction efficiency. Oligodendroglial precursors may enhance remyelination in MS lesions.

The oligodendrocyte performs a multitude of functions related to its production and maintenance of the myelin sheath. This provides insulation, support and conductance enhancement for the axons of multiple neurons. A single oligodendrocyte may myelinate up to 50 different axons. Myelination is restricted only to certain, large diameter axons; dendrites and other cell processes, such as those of astrocytes, remain unmyelinated. Axons appear to exert control over the number of myelinating oligodendrocytes, since axonal transection in the paradigm of the rat optic nerve inhibits myelin renewal and oligodendrocyte precursor production (reviewed in Barres and Raff, 1999). Oligodendrocyte proliferation and migration may be stimulated by factors released from axons during development. In this manner, the numbers of oligodendrocytes and axons are carefully matched within the CNS.

Oligodendrocytes, the perineuronal support cells of the CNS, myelinate axonal tracts and serve to enhance impulse transduction. They play roles in axonal survival and function. Note that, as shown in this diagram, an oligodendrocyte extends only one process to each axon it myelinates.

The multilamellar myelin sheath is a specialized domain of the glial cell plasma membrane, rich in lipid and low in protein. It serves to support axons and improve the efficiency of electrical signal conduction in the CNS by preventing the charge from bleeding off into the surrounding tissue. The nodes of Ranvier are the sites in the sheath along the axon where saltatory conductance occurs.

In the adult brain, oligodendrocytes develop from as yet poorly defined precursor cells in the subventricular zone of the brain and spinal cord (Nait-Oumesmar et al., 1999). These precursors are proliferative and express myelin transcripts and proteins, first emerging in the ventral region of the embryonic spinal cord several weeks before myelination (Hajihosseini et al., 1996). The process of myelination occurs in the post-natal brain. During post-natal development, these precursors migrate to the neuron tracts that are to be myelinated.

Oligodendrocytes mature from their precursor cells in a defined and specific manner (reviewed e.g. in Rogister et al., 1999). Oligodendrocyte development follows a defined pathway at which each stage is demarcated by several cell-specific markers: endothelial neural cell adhesion molecule (E-NCAM), vimentin, A2B5, the POU transcription factor Tst-1/Oct6/SCIP, pre-oligodendroblast antigen (POA), galactocerebroside (GalC), O1, O4, and the myelin-specific; proteins PLP, MBP, and MOG. Neural stem cells give rise to bipolar pre-GD3$^+$cells, which become O2A precursors. These cells can give rise to either oligodendrocytes or type 2 astrocytes. Progression continues through the pre-oligodendroglial and pre-GalC$^+$stages, before actual differentiation into oligodendrocytes. The end stages of the oligodendroglial lineage are defined by these cells' inability to proliferate. Mature oligodendrocytes express the cell-specific markers GalC and sulfatide (SUL), in addition to expressing myelin-specific proteins.

Oligodendrocytes therefore differentiate from mitotically active, migratory precursor cells. Once these cells have become post-mitotic, they transcribe and translate genes encoding myelin-specific proteins. The elaboration of the myelin sheath wrapping the axon is brought about by direct contact between the processes of the mature oligodendrocyte and the axon itself. CNS axon ensheathment is completed by compaction of the myelin sheath, which in its final form resembles a liquid crystal containing macromolecules in complex formation (Scherer, 1997). Promotion of myelination; demands consideration of the precise stoichiometric relationship between the individual structural proteins of the myelin sheath, since increasing or decreasing the amount of one component could result in perturbation of the entire sheath structure.

The inability of oligodendrocytes to sustain repair of demyelinated axons contributes to the cumulative neurologic dysfunction characterizing MS. Promotion of remyelination in MS patients could protect axonal loss and thus limit the progression in disability associated with the death of axons in the CNS.

The demyelinating phenotype of MS led to extensive studies on the nature of the active MS lesion. Naked axons and the absence of myelinating oligodendrocytes indicated the disruption of normal myelin and aberrations in the remyelinating process associated with MS. About 40% of MS lesions were shown to exhibit evidence of abortive remyelination, especially in the early phases of the disease (Prineas et al., 1993). This presents the realistic prospect that developing strategies for promoting myelin repair could prevent permanent nervous system damage. Success probability is particularly high in younger CNS lesions, where early remyelination has already been shown to take place. However, the myelinating or remyelinating oligodendrocyte is a cell under extreme metabolic stress, which under pressure of even minor additional insults can be irreversibly damaged (Scolding and Lassmann, 1996). This decreases the probability of spontaneous repair in an active MS lesion, where inflammation and other detriments pose obstacles to remyelination. Strategies promoting myelin repair may thus stack the odds further in favor of remyelination and axonal protection in active MS lesions.

The adult human CNS has been shown to contain oligodendrocyte precursor cells that are capable of proliferating, and which could mature into myelinating oligodendrocytes. In addition, it appears that the endogenous oligodendrocyte precursor populations adjacent to MS lesions are depleted during the chronic phases of the disease, due to inhibition of these precursors' ability to proliferate and differentiate (Wolswijk, 1998). Such precursor cells are generally quiescent in the environment of a chronic MS lesion, preventing them from actively contributing to remyelination. The situation in chronic MS lesions could therefore involve factors that hamper oligodendroglial regeneration or lack factors necessary for the stimulation of the oligodendrocyte precursor cell population (Wolswijk, 1998). This concept led to the hypothesis that an efficient therapy for MS should not be limited to suppressing inflammation but should also favor remyelination. The remyelinating cells could originate from a variety of sources, including surviving oligodendrocytes native to the lesion, cells derived from these survivors, or the adjacent precursor cells. It has been shown that mature oligodendrocytes can be induced to dedifferentiate and proliferate by factors such as basic fibroblast growth factor (bFGF), suggesting a mechanism for regeneration of the oligodendroglial lineage following demyelinating disease (Grinspan et al., 1996; Grinspan et al., 1993).

Additional evidence for the beneficial effects of remyelination in demyelinating disorders such as MS is provided by the studies performed with glial growth factors as treatments in animal models of the disease. Glial growth factor 2 (neuregulin/GGF-2), a CNS growth factor known to promote oligodendrocyte proliferation and survival, was shown to delay disease onset, reduce clinical severity and decrease relapse frequency in the EAE murine model of MS (Marchionni et al., 1999). Neuregulin was shown to have a beneficial effect on mature oligodendrocyte survival and is produced by axons (Fernández et al., 2000).

Other growth factors, including platelet-derived growth factor (PDGF) and IGF-1, have been demonstrated to promote remyelination and have therapeutic effects in EAE models (reviewed in Dubois-Dalcq and Murray, 2000). The success achieved with the stimulation of remyelination, through inducing cells of the oligodendrocyte lineage to proliferate and/or differentiate, indicates that prospects for remyelination as a therapeutic strategy for MS are favorable. It would also be important to identify molecules that inhibit myelin synthesis, since these could lower the effectiveness of repair strategies such as oligodendroglial cell transplantation in MS.

The process of remyelination could work in concert with anti-inflammatory pathways to repair damage and protect axons from transection and death.

Oligodendrocytes may be induced to remyelinate axonal tracts in the CNS, thereby contributing to amelioration of the disease condition. Remyelination enhancement would counteract the previous destruction wrought by invasion of immune system cells into CNS tissue and their attack on myelin sheaths.

Several analyses of oligodendroglial differentiation and multiple sclerosis lesions have been performed using microarray visualization of differential gene expression (DGE, Scarlato et al., 2000; Whitney et al., 1999). These have utilized significantly different array technologies to assay varying sets of genes. Analysis of gene expression in both differentiating oligodendrocytes and multiple sclerosis lesions have indicated significant changes in the expression of myelin-specific genes. In addition, other genes were pinpointed as being differentially regulated, many of which were known to be involved in processes such as cell cycle control, cytoskeletal reorganization and membrane trafficking (Scarlato et al., 2000).

Osteopontin is a highly phosphorylated sialoprotein that is a prominent component of the mineralized extracellular matrices of bones and teeth. OPN is characterized by the presence of a polyaspartic acid sequence and sites of Ser/Thr phosphorylation that mediate hydroxyapatite binding, and a highly conserved RGD motif that mediates cell attachment/signaling. Expression of osteopontin in a variety of tissues indicates a multiplicity of functions that involve one or more of these conserved motifs. While the lack of a clear phenotype in OPN "knockout" mice has not established, a definitive role for osteopontin in any issue, recent studies have provided some novel and intriguing insights into the versatility of this protein in diverse biological events, including developmental processes, wound healing, immunological responses, tumorigenesis, bone resorption, and calcification. The ability of osteopontin to stimulate cell activity through multiple receptors linked to several interactive signaling pathways can account for much of the functional diversity (Sodek et al.).

Osteopontin has also been shown to be expressed in primary sensory neurons in the rat spinal and trigeminal nervous systems, both in the neuronal cell bodies and in the axons (Ichikawa et al., 2000).

Osteopontin mRNA is expressed in the adult brain as shown by in situ hybridization. Expression was found in neurons of the olfactory bulb and the brain stem, and in the latter it was found in functionally diverse areas including motor-related areas, sensory system and reticular formation (Shin et al., 1999).

Another study investigated the spatial and temporal expression of osteopontin mRNA following transient forebrain ischemia in rats. The transient induction of OPN mRNA after global ischemia occurred earlier in the striatum than in the hippocampus. It was pronounced in the dorsomedial striatum close to the lateral ventricle and in the CA1 subfield and the subiculum of the hippocampus before microglial cells became more reactive. It also could be detected in the dentate hilus, and to a marginal extent in the CA3 (Lee M Y, Shin S L, Choi Y S, Kim E J, Cha J H, Chun M H, Lee S B, Kim S Y, Neurosci Lett Aug. 20, 1999 271:2 81–4).

Osteopontin is also called Eta-1. WO 00/63241 relates to methods for modulating immune responses, in particular methods for modulating type 1 immune responses using modulators of Eta-1 (early T lymphocyte activation-1)/osteopontin. Osteopontin modulators are said to be useful for treatment of infections, immune disorders and diseases, autoimmune disorders, including MS, various immunodeficiencies, and cancer. All modulators of osteopontin disclosed in WO 00/63241, which are envisaged to be useful in autoimmune diseases, including MS, are inhibitors of osteopontin/Eta-1, as explained in detail in section V. "Clinical Applications of the Modulatory Methods of the Invention", D "Autoimmune Diseases", on page 51 to 53 of WO 00/63241.

Interferons are a subclass of cytokines that exhibit anti-inflammatory, antiviral and antiproliferative activity. On the basis of biochemical and immunological properties, the naturally-occurring human interferons are grouped into three classes: interferon alpha (leukocyte), interferon beta (fibroblast) and interferon gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential antitumour and antiviral activities.

The three major IFNs are referred to as IFN-α, IFN-β and IFN-γ. Such main kinds of IFNs were initially classified according to their cells of origin (leucocyte, fibroblast or T cell). However, it became clear that several types may be produced by one cell. Hence leucocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkitt's lymphoma), which seems to produce a mixture of both leucocyte and fibroblast IFN.

The Interferon unit has been reported as a measure of IFN activity defined (somewhat arbitrarily) as the amount necessary to protect 50% of the cells against viral damage.

Every class of IFN contains several distinct types. IFN-β and IFN-γ are each the product of a single gene. The differences between individual types seem to be mainly due to variations in glycosylation.

IFNs-α are the most diverse group, containing about 15 types. There is a cluster of IFN-α genes on chromosome 9, containing at least 23 members, of which 15 are active and transcribed. Mature IFNs-α is not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. In effect, these new types of therapeutic agents can be called biologic response modifiers (BRMs), because they have an effect on the response of the organism to the tumour, affecting recognition via immunomodulation.

In particular, human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, Derynk et al. (Derynk R. et al, 1980) deduced the complete amino acid sequence of the protein. It is 166 amino acid long.

Shepard et al. (Shepard H. M. et al. 1981) described a mutation at base 842 (Cys→Tyr at position 141) that abolished its anti-viral activity, and a variant clone with a deletion of nucleotides 1119–1121.

Mark et al. (Mark D. F. et al, 1984) inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

Rebif® (recombinant human Interferon-β) is the latest development in interferon therapy for multiple sclerosis (MS) and represents a significant advance in treatment. Rebif® is interferon(IFN)-beta 1a, produced from mammalian cell lines and virtually identical to the naturally occurring human molecule.

The mechanisms by which IFNs exert their effects are not completely understood. However, in most cases they act by affecting the induction or transcription of certain genes, thus affecting the immune system. In vitro studies have shown that IFNs are capable of inducing or suppressing about 20 gene products IFN-β may act by three major pathways in MS:
regulation of T-cell functions such as activation, proliferation and suppressor cell function;
modulation of the production of cytokines: down-regulation of proinflammatory cytokines and up-regulation of inhibitory, antiinflammatory cytokines;
regulation of T-cell migration and infiltration into the CNS via the BBB (blood brain barrier).

The PRISMS study has established the efficacy of Interferon beta-1a given sub-cutaneously three times per week in the treatment of Relapsing-Remitting Multiple Sclerosis (RR-MS). This study showed that Interferon beta-1a can have a positive effect on the long-term course of MS by reducing the number and severity of relapses and reducing the burden of the disease and disease activity as measured by MRI. (Randomised, Double-Blind, Placebo-Controlled Study of Interferon beta-1a in Relapsing-remitting Multiple Sclerosis". The Lancet 1998; 352 (Nov. 7, 1998): 1498–1504.)

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such statement.

SUMMARY OF THE INVENTION

It is the object of the present invention to provide a novel means for the treatment and/or prevention of a neurologic disease.

The invention is based on the finding that the protein osteopontin promotes glial cell proliferation and differentiation, thus promoting myelination and regeneration of nerves. In accordance with the present invention, it has further been found that osteopontin has a beneficial effect in animal models of multiple sclerosis and peripheral neuropathies.

Therefore, the present invention relates to the use of osteopontin, or of an agonist of osteopontin activity, in a neurologic disease, such as traumatic nerve injury, stroke, demyelinating diseases of the CNS or PNS, neuropathies and neurodegenerative diseases.

In accordance with the present invention, osteopontin may also be used in combination with an interferon for treatment and/or prevention of neurologic diseases. The use of nucleic acid molecules, and expression vectors comprising osteopontin, and of cells expressing osteopontin, for treatment and/or prevention of a neurologic disease is also within the present invention. The invention further provides pharmaceutical compositions comprising osteopontin and an interferon, optionally together with one or more pharmaceutically acceptable excipients.

BRIEF DESCRIPTION OF THE DRAWINGS

FIG. 11A=control; FIG. 11B=OPN treated; FIG. 11C=magnification of FIG. 11B; FIG. 11D=another field of OPN treated mixed cortical cells, where no axons are visible.

FIG. 13 shows the proliferation of CG4 cells after treatment with different dosages (10 pM, 10 nM, 100 nM) of in vitro phosphorylated E. coli expressed osteopontin (OPN-E. coli) or baculovirus expressed osteopontin (OPN Bac).

DETAILED DESCRIPTION OF THE INVENTION

Figure 1:
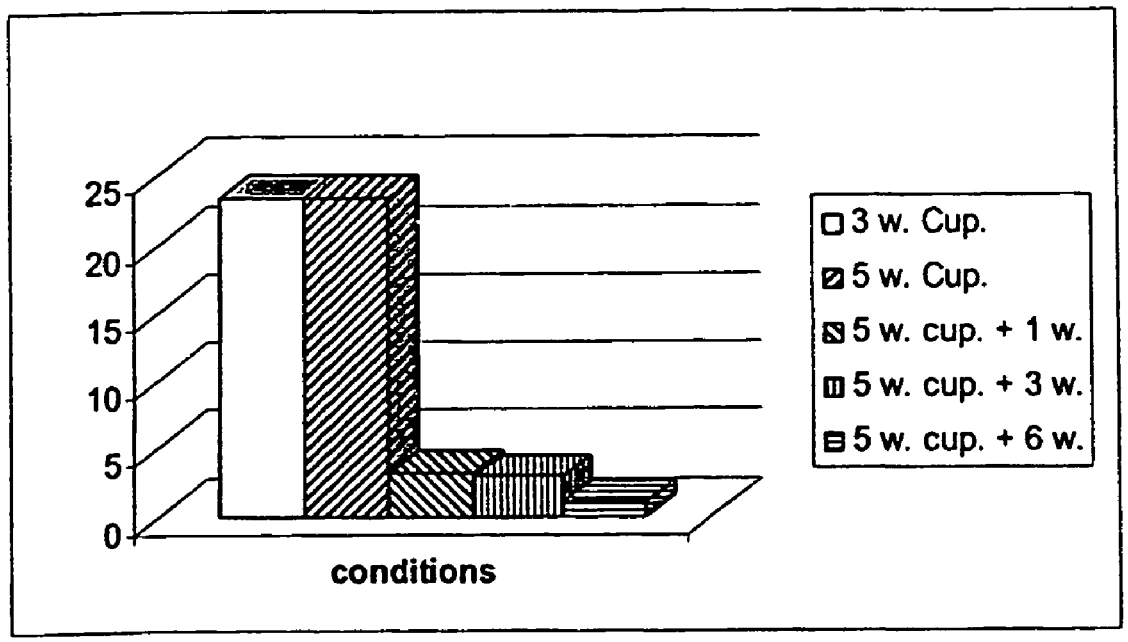
FIG. 1A shows a histogram depicting the levels of osteopontin expression after different times of cuprizone treatment, as measured by TaqMan® analysis. 3/5 w. Cup=three or five weeks of cuprizone treatment, 5w. cup+ 1/3/6w.=five weeks of cuprizone treatment and after withdrawal of cuprizone one/three or six weeks of recovery.
FIG. 1B shows the fold regulation of osteopontin, MBP and PLP mRNA compared to control C1 levels as measured by TaqMan® in different stages of cerebellar development. C1 to 20=postnatal cerebellum at day 1 to 20, CA=adult cerebellum.

The present invention is based on the finding that osteopontin is differentially expressed during oligodendrocyte differentiation and during the development of the cerebellum. It has further been found that expression of osteopontin cDNA in oligodendrocytes leads to a differentiated phenotype of these cells in vitro. Upon expression of osteopontin, oligodendrocytes display a phenotype similar to the phenotype of a differentiating, myelinating cell. In addition to these in vitro findings, it has been shown that osteopontin, and in particular the combination of osteopontin and an interferon, have a beneficial effect in an established model of multiple sclerosis. In an experimental model of peripheral neuropathy, osteopontin had a pronounced beneficial effect on nerve activity, and significantly reduced the percentage of degeneration and enhanced the extent of myelination.

The experimental evidence presented herein therefore provides for a new possibility of treating neurologic diseases, in particular those linked to nervous and glial cell function. These findings are particularly surprising because WO 00/63241 teaches to inhibit osteopontin in order to treat multiple sclerosis.

The invention therefore relates to the use of osteopontin, or of an agonist of osteopontin activity, for the manufacture of a medicament for treatment and/or prevention of neurologic diseases.

The term "osteopontin", as used herein, relates to full-length human osteopontin, having the amino acid sequence that has been known since the late eighties (Oldberg et al., 1986; Kiefer et al., 1989). The sequence of human osteopontin is reported herein as SEQ ID NO: 1 of the annexed sequence listing. The term "osteopontin", as used herein, further relates to any osteopontin derived from animals, such as murine, bovine, or rat osteopontin, as long as there is sufficient identity in order to maintain osteopontin activity, and as long as the resulting molecule will not be immunogenic in humans.

The term "osteopontin", as used herein, further relates to biologically active muteins and fragments, such as the naturally occurring isoforms of osteopontin. Osteopontin is expressed in functionally distinct forms that differ at the level of transcription (alternative splicing) and posttranslational modifications (phosphorylation, glycosylation). Three splice variants of OPN are known so far, designated OPN-a (herein also called "full-length" osteopontin), OPN-b and OPN-c (SEQ ID NO: 1, 2 and 3 of the annexed sequence listing, also depicted in FIG. 2). The isoforms were described e.g. by Kon et al. (2000), and characterized e.g. by Saitoh et al. (1995) and Kon et al. (2002).

A thrombin cleavage leads to two in vivo proteolytic cleavage fragments comprising the N- and C-terminal portions of the protein. Phosphorylation of osteopontin, in particular of the C-terminal portion of the proteins, may be important for osteopontin function. The term "osteopontin" as used herein, is therefore also meant to encompasses these proteolytic fragments and differentially phosphorylated osteopontin forms.

The term "osteopontin", as used herein, further encompasses isoforms, muteins, fused proteins, functional derivatives, active fractions or fragments, or circularly permutated derivatives, or salts thereof. These isoforms, muteins, fused proteins or functional derivatives, active fractions or fragments, or circularly permutated derivatives retain the biological activity of osteopontin. Preferably, they have a biological activity, which is improved as compared to wild type osteopontin.

The term "agonist of osteopontin activity", as used herein, relates to a molecule stimulating or imitating osteopontin activity, such as agonistic antibodies of the osteopontin receptor, or small molecular weight agonists activating signaling through an osteopontin receptor. Osteopontin mediates its function through at least two groups of receptors. First, it interacts with αv-integrins (αvβ3 and αvβ5 integrin receptors via an RGD (Arg-Gly-Asp) cell attachment motif under the positive influence of manganese (Kunicki et al., 1997). Second, it interacts with CD44 variant isoforms v6-v10. The C-terminal part of osteopontin is believed to be involved in, the interaction with CD44, while the N-terminal part of osteopontin is believed to be involved in interaction with integrin receptors, proliferation, survival and differentiation of macrophages. The N-terminal portion of osteopontin also induces IL-12 and IL-10 release. Any agonist, stimulator or enhancer, of any of these receptors is encompassed by the term "agonist of OPN activity", as used herein.

The term "agonist of osteopontin activity", as used herein, further refers to agents enhancing osteopontin mediated activities, such as promotion of cell attachment to extracellular matrix components, the morphogenesis of cells of the oligodendrocyte lineage intomyelin producing cells, to promote the recruitment, proliferation, differentiation or maturation of cells of the oligodendrocyte lineage (such as progenitors or precursor cells), to promote the protection of cells of the oligodendrocyte lineage from apoptosis and cell injury.

The terms "treating" and "preventing", as used herein, should be understood as preventing, inhibiting, attenuating, ameliorating or reversing one or more symptoms or cause(s)

of neurologic disease, as well as symptoms, diseases or complications accompanying neurologic disease. When "treating" neurologic disease, the substances according to the invention are given after onset of the disease, "prevention" relates to administration of the substances before signs of disease can be noted in the patient.

The term "neurologic diseases", as used herein encompasses all known neurologic diseases or disorders, or injuries of the CNS or PNS, including those described in detail in the "Background of the invention".

Neurologic diseases comprise disorders linked to dysfunction of the CNS or PNS, such as diseases related to neurotransmission, headache, trauma of the head, CNS infections, neuro-ophthalmologic and cranial nerve disorders, function and dysfunction of the cerebral lobes disorders of movement, stupor and coma, demyelinating diseases, delirium and dementia, craniocervical junction abnormalities, seizure disorders, spinal cord disorders, sleep disorders, disorders of the peripheral nervous system, cerebrovascular disease, or muscular disorders. For definitions of these disorders, see e.g. www.merck.com/pubs/manual/section14/sec14.htm.

Preferably, the neurologic diseases of the invention are selected from the group consisting of traumatic nerve injury, stroke, demyelinating diseases of the CNS or PNS and neurodegenerative diseases.

Traumatic nerve injury may concern the PNS or the CNS, it may be brain or spinal cord trauma, including paraplegia, as described in the "background of the invention" above.

Stroke may be caused by hypoxia or by ischemia of the brain. It is also called cerebrovascular disease or accident. Stroke may involve loss of brain functions (neurologic deficits) caused by a loss of blood circulation to areas of the brain. Loss of blood circulation may be due to blood clots that form in the brain (thrombus), or pieces of atherosclerotic plaque or other material that travel to the brain from another location (emboli). Bleeding (hemorrhage) within the brain may cause symptoms that mimic stroke. The most common cause of a stroke is stroke secondary to atherosclerosis (cerebral thrombosis), and therefore the invention also relates to the treatment of atherosclerosis.

Peripheral Neuropathy may be related to a syndrome of sensory loss, muscle weakness and atrophy, decreased deep tendon reflexes, and vasomotor symptoms, alone or in any combination. Neuropathy may affect a single nerve (mononeuropathy), two or more nerves in separate areas (multiple mononeuropathy), or many nerves simultaneously (polyneuropathy). The axon may be primarily affected (e.g. in diabetes mellitus, Lyme disease, or uremia or with toxic agents), or the myelin sheath or Schwann cell (e.g. in acute or chronic inflammatory polyneuropathy, leukodystrophies, or Guillain-Barré syndrome). Further neuropathies, which may be treated in accordance with the present invention, may e.g. be due to lead toxicity, dapsone use, tick bite, porphyria, or Guillain-Barré syndrome, and they may primarily affect motor fibers. Others, such as those due to dorsal root ganglionitis of cancer, leprosy, AIDS, diabetes mellitus, or chronic pyridoxine intoxication, may primarily affect the dorsal root ganglia or sensory fibers, producing sensory symptoms. Cranial nerves may also be involved, such as e.g. in Guillain-Barré syndrome, Lyme disease, diabetes mellitus, and diphtheria.

Alzheimer's disease is a disorder involving deterioration in mental functions resulting from changes in brain tissue. This may include shrinking of brain tissues, primary degenerative dementia and diffuse brain atrophy. Alzheimer's disease is also called senile dementia/Alzheimer's type (SDAT).

Parkinsons's disease is a disorder of the brain including shaking and difficulty with walking, movement, and coordination. The disease is associated with damage to a part of the brain that controls muscle movement, and it is also called paralysis agitans or shaking palsy.

Huntington's Disease is an inherited, autosomal dominant neurologic disease.

Amyptrophic Lateral Sclerosis, ALS, is a disorder causing progressive loss of nervous control of voluntary muscles, including of destruction of nerve cells in the brain and spinal cord. Amyotrophic Lateral Sclerosis, also called Lou Gehrig's disease, is a disorder involving loss of the use and control of muscles.

Multiple Sclerosis (MS) is an inflammatory demyelinating disease of the central nervous system (CNS) that takes a relapsing-remitting or a progressive course. MS is not the only demyelinating disease. Its counterpart in the peripheral nervous system (PNS) is chronic inflammatory demyelinating polyradiculoneuropathy (CIDP). In addition, there are acute, monophasic disorders, such as the inflammatory demyelinating polyradiculoneuropathy termed Guillain-Barré syndrome (GBS) in the PNS, and acute disseminated encephalomyelitis (ADEM) in the CNS.

Further neurologic disorders comprise neuropathies with abnormal myelination, such as the ones listed in the "Background of the invention" above, as well as carpal tunnel syndrome. Traumatic nerve injury may be accompanied by spinal column orthopedic complications, and those are also within the diseases in accordance with the present invention.

Neurologic disorders may further be due to congenital metabolic disorders. In a preferred embodiment of the invention, the neurologic disease is therefore due to a congenital metabolic deficit.

The congenital metabolic disorders encompassed by the present invention may be e.g. phenylketonuria and other aminoacidurias, Tay-Sachs, Niemann-Pick, and Gaucher's diseases, Hurler's syndrome; Krabbe's disease and other leukodystrophies. They may affect the developing myelin sheath, mainly in the CNS.

Neurologic diseases caused by congenital metabolic disorders have also been discussed in detail in the "Background of the invention".

Less well known neurologic diseases are also within the scope of the present invention, such as neurofibromatosis, or Multiple System Atrophy (MSA). Further disorders that may be treated in accordance with the present invention, have been described in detail in the "Background of the invention" above.

In a further preferred embodiment, the neurologic disease is a peripheral neuropathy, most preferably diabetic neuropathy. Chemotherapy associated neuropathies are also preferred in accordance with the present invention.

The term "diabetic neuropathy" relates to any form of diabetic neuropathy, or to one or more symptom(s) or disorder(s) accompanying or caused by diabetic neuropathy, or complications of diabetes affecting nerves as described in detail in the "Background of the invention2 above. Diabetic neuropathy may be a polyneuropathy. In diabetic polyneuropathy, many nerves are simultaneously affected. The diabetic neuropathy may also be a mononeuropathy. In focal mononeuropathy, for instance, the disease affects a single nerve, such as the oculomotor or abducens cranial nerve. It may also be multiple mononeuropathy when two or more nerves are affected in separate areas.

In yet a further preferred embodiment, the neurologic disorder is a demyelinating disease. Demyelinating diseases preferably comprise demyelinating conditions of the CNS, like acute disseminated encephalomyelitis (ADEM) and multiple sclerosis (MS), as well as demyelinating diseases of the peripheral nervous system (PNS). The latter comprise diseases such as chronic inflammatory demyelinating polyradiculoneuropathy. (CIDP and acute, monophasic disorders, such as the inflammatory demyelinating: polyradiculoneuropathy termed Guillain-Barré syndrome (GBS).

A further preferred embodiment of the invention relates to the treatment and/or prevention of a neurodegenerative disease. The neurodegenerative disease is selected from the group consisting of Alzheimer's disease, Parkinson's disease, Huntington's disease and ALS.

Preferably, the osteopontin is selected from a peptide, a polypeptide or a protein selected from the group consisting of:

(a) A polypeptide comprising SEQ ID NO: 1;

(b) A polypeptide comprising amino acids 1 to 168 or 170 of SEQ ID NO: 1;

(c) A polypeptide comprising amino acids 1 to 16 and 170 to 314 of SEQ ID NO: 1;

(d) A polypeptide comprising amino acids 170 to 314 of SEQ ID NO: 1;

(e) A polypeptide comprising SEQ ID NO: 2;

(f) A polypeptide comprising SEQ ID NO: 3;

(g) A mutein of any of (a) to (f), wherein the amino acid sequence has at least 40% or 50% or 60% or 70% or 80% or 90% identity to at least one of the sequences in (a) to (f);

(h) A mutein of any of (a) to (f) which is encoded by a DNA sequence which hybridizes to the complement of the native DNA sequence encoding any of (a) to (f) under moderately stringent conditions or under highly stringent conditions;

(i) A mutein of any of (a) to (f) wherein any changes in the amino acid sequence are conservative amino acid substitutions to the amino acid sequences in (a) to (f);

(j) a salt or an isoform, fused protein, functional derivative, active fraction or circularly permutated derivative of any of (a) to (f).

Figure 2:
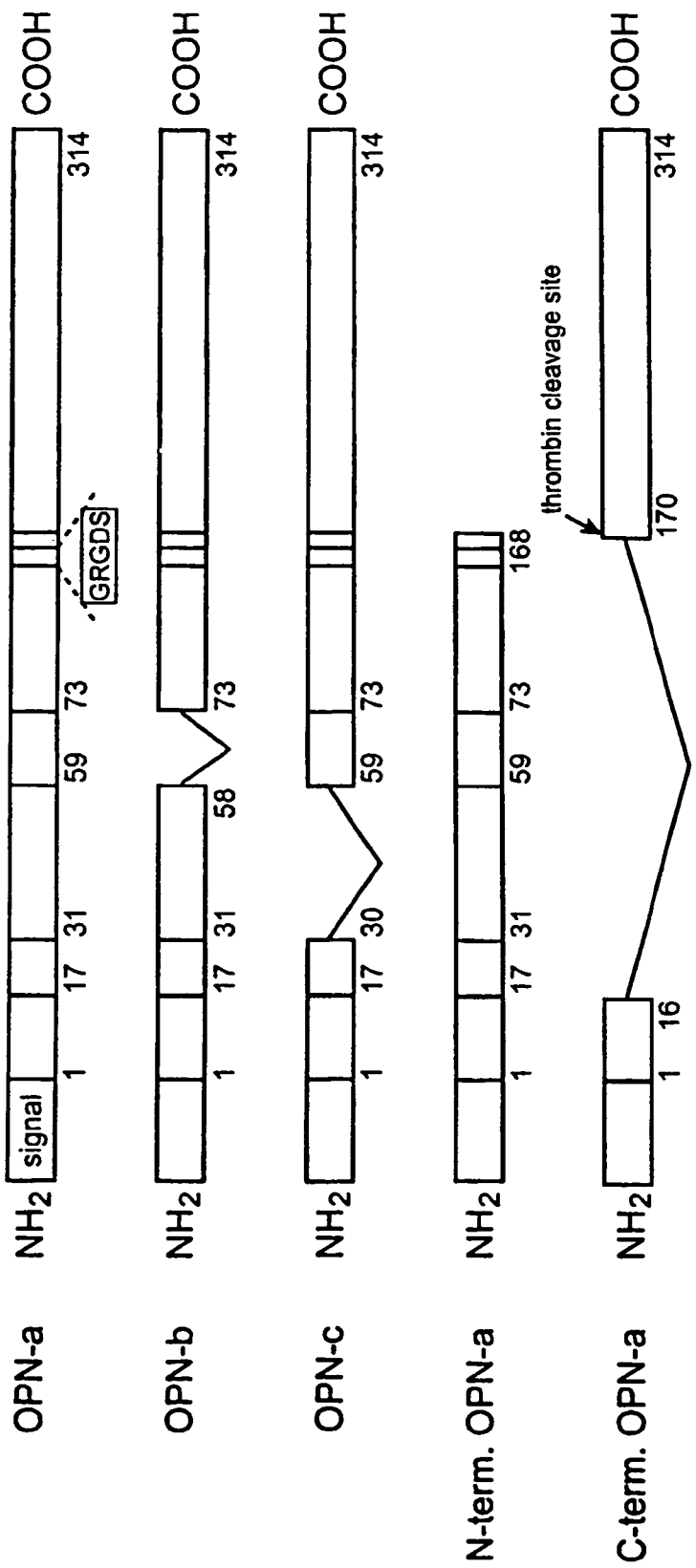
FIG. 2 schematically depicts the structure of osteopontin and its known isoforms as well as C and N terminal constructs.

Active fractions or fragments may comprise any portion or domain of any of the osteopontin isoforms, such as an N-terminal portion or a C-terminal portion, or any of OPN-a, -b, or -c, as shown in FIG. 2. The GRGDS motif may be present, or absent, or mutated. The heparin binding site may be mutated so as to render osteopontin devoid of heparin-binding. Full length osteopontin, or any active fragment thereof, may be phosphorylated at one or more of the following serine residues, such as the serine residues at the following positions: 8, 10, 11, 33, 46, 47, 60, 62, 65, 83, 86, 89, 92, 101, 104, 107, 110, 113, 153, 155, 175, 179, 199, 203, 208, 212, 218, 223, 227, 238, 242, 247, 251, 254, 259, 264, 275, 287, 292, 294, 295. Additionally, the serine phosphorylation sites may be mutated from serine to glutamate residues, in order to mimic phosphorylation.

The person skilled in the art will appreciate that even smaller portions of osteopontin may be enough to exert its function, such as an active peptide comprising the essential amino acid residues required for osteopontin function.

The person skilled in the art will further appreciate that muteins, salts, isoforms, fused proteins, functional derivatives of osteopontin, active fractions or circularly permutated derivatives of osteopontin, will retain a similar, or even better, biological activity of osteopontin. The biological activity of osteopontin and muteins, isoforms, fused proteins or functional derivatives, active fractions or fragments, circularly permutated derivatives, or salts thereof, may be measured in a co-culturing assay, such as the one described below in Example 8. Mixed cortical cultures contain oligodendrocytes, as well as other CNS derived cells (such as neurons, astrocytes, microglia), and induce or up-regulate the typical genes involved in myelination, like P0, MBP or MAG, upon incubation with OPN or the mutein, isoform, fragment, active fraction, functional derivative or salt. Expression of these genes can be measured by quantitative real time RT-PCR (TaqMan® RT-PCR) analysis, which is explained in detail in the examples below. A further simple assay to measure OPN activity is an oligodendrocyte proliferation assay, comprising incubating an adequate oligodendrocyte cell line, such as oli-neu or CG4 cells, with OPN or the mutein, isoform, fragment, active fraction, functional derivative or salt, as described in Example 7 below, for example.

Preferred active fractions have an activity which is equal or better than the activity of full-length osteopontin, or which have further advantages, such as a better stability or a lower toxicity or immunogenicity, or they are easier to produce in large quantities, or easier to purify. The person skilled in the art will appreciate that muteins, active fragments and functional derivatives can be generated by cloning the corresponding cDNA in appropriate plasmids and testing them in the co-culturing assay, as mentioned above.

The proteins according to the present invention may be glycosylated or non-glycosylated, they may be derived from natural sources, such as body fluids, or they may preferably be produced recombinantly. Recombinant expression may be carried out in prokaryotic expression systems such as *E. coli*, or in eukaryotic, such as insect cells, and preferably in mammalian expression systems, such as CHO-cells or HEK-cells.

As used herein the term "muteins" refers to analogs of osteopontin, in which one or more of the amino acid residues of a natural osteopontin are replaced by different amino acid residues, or are deleted, or one or more amino acid residues are added to the natural sequence of osteopontin, without changing considerably the activity of the resulting products as compared with the wild-type osteopontin. These muteins are prepared by known synthesis and/or by site-directed mutagenesis techniques, or any other known technique suitable therefor.

Muteins of osteopontin, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

Muteins in accordance with the present invention include proteins encoded by a nucleic acid, such as DNA or RNA, which hybridizes to DNA or RNA, which encodes OPN, in accordance with the present invention, under moderately or highly stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al.(Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12–20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30–60 minutes and then, a 0.1×SSC and 0.5% SDS at 68° C. for 30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See Ausubel, supra.

In a preferred embodiment, any such mutein has at least 40% identity or homology with the sequence of SEQ ID NO: 1, 2 or 3 of the annexed sequence listing. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global, alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Preferred changes for muteins in accordance with the present invention are what are known as "conservative" substitutions. Conservative amino acid substitutions of osteopontin polypeptides, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g. cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |

TABLE III-continued

Most Preferred Groups of Synonymous Amino Acids

| Amino Acid | Synonymous Group |
|---|---|
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of osteopontin, polypeptides or proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising osteopontin, or a mutein or fragment thereof, fused with another protein, which, e.g. has an extended residence time in body fluids. An osteopontin may thus be fused to another protein, polypeptide or the like, e.g. an immunoglobulin or a fragment thereof.

"Functional derivatives" as used herein, cover derivatives of osteopontin, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of osteopontin, and do not confer toxic properties on compositions containing it.

These derivatives may, for example, include polyethylene glycol side-chains, which may mask antigenic sites and extend the residence of an osteopontin in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g alkanoyl or carbocyclic aroyl groups) or O-acyl derivatives of free hydroxyl groups (for example that of seryl or threonyl residues) formed with acyl moieties.

As "active fractions" of osteopontin, muteins and fused proteins, the present invention covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has substantially similar activity to osteopontin.

The term "salts" herein refers to both salts of carboxyl groups and to acid addition salts of amino groups of OPN molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of OPN relevant to the present invention, i.e., exert a proliferative effect on oligodendrocytes.

In a preferred embodiment of the invention, osteopontin is fused to a carrier molecule, a peptide or a protein that promotes the crossing of the blood brain barrier ("BBB"). This serves for proper targeting of the molecule to the site of action in those cases, in which the CNS is involved in the disease. Modalities for drug delivery through the BBB entail disruption of the BBB, either by osmotic means or biochemically by the use of vasoactive substances such as bradykinin. Other strategies to go through the BBB may entail the use of endogenous transport systems, including carrier-mediated transporters such as glucose and amino acid carriers; receptor-mediated transcytosis for insulin or transferrin; and active efflux transporters such as p-glycoprotein. Strategies for drug delivery behind the BBB further include intracerebral implantation.

Functional derivatives of osteopontin may be conjugated to polymers in order to improve the properties of the protein, such as the stability, half-life, bioavailability, tolerance by the human body, or immunogenicity. To achieve this goal, osteopontin may be linked e.g. to Polyethlyenglycol (PEG). PEGylation may be carried out by known methods, described in WO 92/13095, for example.

Therefore, in a preferred embodiment of the present invention, osteopontin is PEGylated.

In a further preferred embodiment of the invention, the fused protein comprises an immunoglobulin (Ig) fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 6) introduced between osteopontin sequence and the immunoglobulin sequence, for instance. The resulting fusion protein has improved properties, such as an extended residence time in body fluids (half-life), or an increased specific activity, increased expression level. The Ig fusion may also facilitate purification of the fused protein.

In a yet another preferred embodiment, osteopontin is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM, for example. Fusion proteins may be monomeric or multimeric, hetero- or homomultimeric. The immunoglobulin portion of the fused protein may be further modified in a way as to not activate complement binding or the complement cascade or bind to Fc-receptors.

The invention further relates to the use of a combination of osteopontin and an immunosuppressive agent for the manufacture of a medicament for treatment and/or prevention of neurologic disorders, for simultaneous, sequential or separate use. Immunosuppressive agents may be steroids, methotrexate, cyclophosphamide, anti-leukocyte antibodies (such as CAMPATH-1), and the like.

The invention further relates to the use of a combination of osteopontin and an interferon for the manufacture of a medicament for treatment and/or prevention of neurologic disorders, for simultaneous, sequential, or separate use.

The term "interferon", as used in the present patent application, is intended to include any molecule defined as such in the literature, comprising for example any kinds of IFNs mentioned in the above section "Background of the Invention". The interferon may preferably be human, but also derived from other species, as long as the biological activity is similar to human interferons, and the molecule is not immunogenic in man.

In particular, any kinds of IFN-α, IFN-β and IFN-γ are included in the above definition. IFN-β is the preferred IFN according to the present invention.

The term "interferon-beta (IFN-β)", as used in the present invention, is intended to include human fibroblast interferon, as obtained by isolation from biological fluids or as obtained by DNA recombinant techniques from prokaryotic or eukaryotic host cells as well as its salts, functional derivatives, variants, analogs and fragments.

"Functional derivatives", as used herein, covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of the proteins as described above, such as the ability to bind the corresponding receptor and initiate receptor signaling, and do, not confer toxic properties on compositions containing it. Derivatives may have chemical moieties, such as carbohydrate or phosphate residues, provided such a derivative retains the biological activity of the protein and remains pharmaceutically acceptable.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g. alkanoyl or carbocyclic aroyl groups) or O-acyl derivatives of free hydroxyl group (e.g. that of seryl or threonyl residues) formed with acyl moieties. Such derivatives may also include for example, polyethylene glycol side-chains which may mask antigenic sites and extend the residence of the molecule in body fluids.

Of particular importance is a protein that has been derivatized or combined with a complexing agent to be long lasting. For example, PEGylated versions, as mentioned above, or proteins genetically engineered to exhibit long lasting activity in the body, can be used according to the present invention.

The term "derivatives" is intended to include only those derivatives that do not change one amino acid to another of the twenty commonly-occurring natural amino acids.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (osteopontin and IFN-beta, respectively) relevant to the present invention, i.e., the ability to bind to the corresponding receptor and initiate receptor signaling.

Interferons may also be conjugated to polymers in order to improve the stability of the proteins. A conjugate between Interferon β and the polyol Polyethlyenglycol (PEG) has been described in WO99/55377, for instance.

In another preferred embodiment of the invention, the interferon is Interferon-β (IFN-β), and more preferably IFN-β1a.

Osteopontin is preferably used simultaneously, sequentially, or separately with the interferon.

In a preferred embodiment of the present invention, osteopontin is used in an amount of about 0.0001 to 100 mg/kg of body weight, or about 0.01 to 10 mg/kg of body weight or about 1 to 5 mg/kg of body weight or about 2 mg/kg of body weight.

The invention further relates to the use of a nucleic acid molecule for manufacture of a medicament for the treatment and/or prevention of a neurologic disease, wherein the nucleic acid molecule comprises a nucleic acid sequence encoding a polypeptide comprising an amino acid sequence selected from the group consisting of:

(a) A polypeptide comprising SEQ ID NO: 1;
(b) A polypeptide comprising amino acids 1 to 168 or 170 of SEQ ID NO: 1;
(c) A polypeptide comprising amino acids 1 to 16 and 170 to 314 of SEQ ID NO: 1;
(d) A polypeptide comprising amino acids 170 to 314 of SEQ ID NO: 1;
(e) A polypeptide comprising SEQ ID NO: 2;
(f) A polypeptide comprising SEQ ID NO: 3;
(g) A mutein of any of (a) to (f), wherein the amino acid sequence has at least 40% or 50% or 60% or 70% or 80% or 90% identity to at least one of the sequences in (a) to (f);
(h) A mutein of any of (a) to (f) which is encoded by a DNA sequence which hybridizes to the complement of the native DNA sequence encoding any of (a) to (f) under moderately stringent conditions or under highly stringent conditions;
(i) A mutein of any of (a) to (f) wherein any changes in the amino acid sequence are conservative amino acid substitutions to the amino acid sequences in (a) to (f);
(j) an isoform, fused protein, functional derivative, active fraction or circularly permutated derivative of any of (a) to (f).

The nucleic acid may e.g. be administered as a naked nucleic acid molecule, e.g. by intramuscular injection.

It may further comprise vector sequences, such as viral sequence, useful for expression of the gene encoded by the nucleic acid molecule in the human body, preferably in the appropriate cells or tissues.

Therefore, in a preferred embodiment, the nucleic acid molecule further comprises an expression vector sequence. Expression vector sequences are well known in the art, they comprise further elements serving for expression of the gene of interest. They may comprise regulatory sequence, such as promoter and enhancer sequences, selection marker sequences, origins of multiplication, and the like. A gene therapeutic approach is thus used for treating and/or preventing the disease. Advantageously, the expression of osteopontin will then be in situ.

In a preferred embodiment, the expression vector is a lentiviral derived vector. Lentiviral vectors have been shown to be very efficient in the transfer of genes, in particular within the CNS. Other well established viral vectors, such as adenoviral derived vectors, may also be used according to the invention.

A targeted vector may be used in order to enhance the passage of osteopontin across the blood-brain barrier. Such vectors may target for example the transferrin receptor or other endothelial transport mechanisms.

In a preferred embodiment of the invention, the expression vector may be administered by intramuscular injection.

The use of a vector for inducing and/or enhancing the endogenous production of osteopontin in a cell normally silent for expression of osteopontin, or which expresses amounts of osteopontin which are not sufficient, are also contemplated according to the invention. The vector may comprise regulatory sequences functional in the cells desired to express osteopontin. Such regulatory sequences may be promoters or enhancers, for example. The regulatory sequence may then be introduced into the appropriate locus of the genome by homologous recombination, thus operably linking the regulatory sequence with the gene, the expression of which is required to be induced or enhanced. The technology is usually referred to as "endogenous gene activation" (EGA), and it is described e.g. in WO 91/09955.

The invention further relates to the use of a cell that has been genetically modified to produce osteopontin in the manufacture of a medicament for the treatment and/or prevention of neurologic diseases.

The invention further relates to a cell that has been genetically modified to produce osteopontin for manufacture of a medicament for the treatment and/or prevention of neurologic diseases. Thus, a cell therapeutic approach may be used in order to deliver the drug to the appropriate parts of the human body.

The invention further relates to pharmaceutical compositions, particularly useful for prevention and/or treatment of neurologic diseases, which comprise a therapeutically effective amount of osteopontin and a therapeutically effective amount of an interferon, optionally further a therapeutically effective amount of an immunosuppressant.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, epidural, topical, intrathecal, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of protein, the affinity of the protein, any residual cytotoxic activity exhibited by the antagonists, the route of administration, the clinical condition of the patient (including the desirability of maintaining a non-toxic level of endogenous osteopontin activity).

A "therapeutically effective amount" is such that when administered, the osteopontin exerts a beneficial effect on the neurologic disease. The dosage administered, as single or multiple doses, to an individual will vary depending upon a variety of factors, including osteopontin pharmacokinetic properties, the route of administration, patient conditions and characteristics (sex, age, body weight, health, size), extent of symptoms, concurrent treatments, frequency of treatment and the effect desired.

As mentioned above, osteopontin can preferably be used in an amount of about 0.0001 to 10 mg/kg or about 0.01 to 5 mg/kg or body weight, or about 0.01 to 5 mg/kg of body weight or about 0.1 to 3 mg/kg of body weight or about 1 to 2 mg/kg of body weight. Further preferred amounts of osteopontin are amounts of about 0.1 to 1000 µg/kg of body weight or about 1 to 100 µg/kg of body weight or about 10 to 50 µg/kg of body weight The route of administration, which is preferred according to the invention is administration by subcutaneous route. Intramuscular administration is further preferred according to the invention.

In further preferred embodiments, osteopontin is administered daily or every other day.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, osteopontin can be administered prophylactically or therapeutically to an individual prior to, simultaneously or sequentially with other therapeutic regimens or agents (e.g. multiple drug regimens), in a therapeutically effective amount, in particular with an interferon. Active agents that are administered simultaneously with other therapeutic agents can be administered in the same or different compositions.

The invention further relates to a method for treating a neurologic disease comprising administering to a patient in need thereof an effective amount of osteopontin, or of an agonist of osteopontin activity, optionally together with a pharmaceutically acceptable carrier.

A method for treating a neurologic disease comprising administering to a patient in need thereof an effective amount of osteopontin, or of an agonist of osteopontin activity, and an interferon, optionally together with a pharmaceutically acceptable carrier, is also within the present invention.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Example 1

Osteopontin is Differentially Expressed in in Vivo and in Vitro Models of Demyelinating Diseases Methods In Vitro Model Systems The Oli-neu cell line has been established via immortalization of oligodendroglial precursors with a replication-defective retrovirus encoding the t-neu oncogene, a constitutively active tyrosine kinase: this cell line was shown to be induced to differentiate in the presence of 1 mM dibutyryl-cAMP in the culture medium (Jung et al., 1995). This provided the possibility of studying oligodendrocytes as an isolated cell type.

The morphology and antigenic characteristics of cells of the mouse oligodendrocyte cell line Oli-neu, derived from A2B5 mouse oligodendrocyte precursors, in the untreated condition and after 6 days of pro-differentiating treatment with 1–5 mM dibutyryl-cAMP differs substantially. Whereas untreated Oli-neu cells have a round shape and are mostly bipolar like oligodendrocyte precursor cells, cAMP treated cells generate multiple processes, have a flat phenotype, and even produce flat, extended "sheath-like" structures Additionally, an in vitro myelination assay using mixed cortical cultures can be used to enable visualization of functional myelin in vitro. This system provides the possibility of studying how oligodendrocytes contact and myelinate axons in the presence of other CNS cell types (Lubetzki et al., 1993) In this system, biological factors can be tested, which might influence the proliferation of oligodendrocyte precursors or act on the differentiation and survival of oligodendrocytes, such as influencing the formation of real myelin segments. The need to study the process of myelination in vitro has led to the development of a range of assay types, including aggregating brain cell cultures (Matthieu et al., 1992), cerebellar slice cultures (Notterpek et al., 1993), and co-culturing systems (Shaw et al., 1996; Barres et al., 1993). These models have the advantage of permitting the study of oligodendrocyte behavior in conjunction with other cell types and how these cells are stimulated to produce myelin. Demyelination can also be provoked in such systems via specific insults, and the response process of remyelination can also be studied.

In Vivo Model Systems

There exist a wide range of experimental in vivo and in vitro models for multiple sclerosis. Most of the in vivo models are related to the classical animal model of MS, experimental allergic encephalomyelitis (EAE). There are many variations on this model, which has been adapted for use in a wide range of mammalian organisms, including the mouse, rat, and primate systems (reviewed in Petry et al., 2000). Additionally, methodologies have been formulated for "mimicking" the proposed viral component of MS in animal models such as the encephalitogenic Theiler's murine virus model of MS (Dal Canto et al., 1995).

Animal models for exclusively studying myelination in the CNS or PNS are less commonly used. It has proven useful to observe the process of developmental myelination in order to gain some insight into the mechanisms underlying oligodendroglial or Schwann cell differentiation, migration, and proliferation, following the "recapitulation hypothesis" (Franklin and Hinks, 1999). However, in order to compare developmental myelination, which occurs while the CNS or PNS is still being formed, and remyelination, which occurs in an adult paradigm, it has been necessary to formulate models that specifically address the process of remyelination.

The Cuprizone Model

One of the most well known and widely used of the remyelination models is the Cuprizone model for remyelination in the mouse. This involves oral administration of an organic compound, Cuprizone, a copper chelator that has been shown to be selectively toxic to oligodendrocytes (Morell et al., 1998).

Demyelination and remyelination occur in the corpus callosum of Cuprizone-treated mice. These pathological conditions can be visualized by staining with anti-CNPase antibody or MBP antibody. Myelin is stained with Luxol Fast Blue-periodic acid Schiff (LFB-PAS). Remyelinating oligodendrocyte precursors can be visualized using antibodies for PDGFα receptor or NG2.

Administration of Cuprizone to mice over a period of 3–5 weeks results in extensive demyelination of the corpus callosum. Concomitant with demyelination, synthesis of myelin-specific gene transcripts is upregulated after 3 weeks of Cuprizone administration (Morell et al., 1998).

Subsequent cessation of the Cuprizone regimen creates an environment conducive to recovery, such that 6 weeks after ceasing Cuprizone feeding, the mice exhibit extensive remyelination in the corpus callosum. Thus, the Cuprizone model provides a complete in vivo paradigm within which to study aspects of demyelination and remyelination. Its advantages include the absence of T-cell infiltration into CNS tissue, enabling more exclusive study of myelination processes, as well as the reproducibility of results (Hiremath et al., 1998).

For Cuprizone treatment, C57BU/6 female mice (8 weeks old, 20±3 g) were used in the study, which involved 6 groups, each containing 6 animals.

Group 1: control group fed with normal powdered chow;

Group 2: fed for 3 weeks on a powdered diet containing 0.2% Cuprizone (Cup3w);

Group 3: fed for 5 weeks on a powdered diet containing 0.2% Cuprizone (Cup5w);

Group 4: fed for 5 weeks on a powdered diet containing 0.2% Cuprizone, followed by a 1-week recovery period on a normal powdered diet (1wR);

Group 5: fed for 5 weeks on a powdered diet containing 0.2% Cuprizone, followed by a 3-week recovery period on a normal powdered diet (3wR);

Group 6: fed for 5 weeks on a powdered diet containing 0.2% Cuprizone, followed by a 6-week recovery period on a normal powdered diet (6wR).

Brains were collected from the animals in each group at the end of each treatment at fixed times. Mice were first anesthetized and perfused via the left ventricle. Brains were collected and serial coronal sections were made at the level of corpus callosum-caudate putamen (striatum) and hippocampus. Brain tissue sections were embedded in paraffin for immunohistochemistry and in situ hybridization.

Histological Tissue Preparation

Formalin was prepared by diluting 1 volume of formaldehyde (Fluka, 36% p.a.), and 1 volume of sterile PBS, with 8 volumes of sterile water. A silicon tube adapted to a peristaltic pump and fitted with a 20G, 1⅕ needle was filled with 10 ml of PBS. The tube was then filled continuously with 40 ml of formalin, with care being taken to prevent air bubble formation.

Animals were anesthetized with sodium pentobarbital (Sanofi®), diluted 1:1 with sterile PBS to a concentration of 3 mg/100 ml, prior to intracardial perfusion with fixative to permit subsequent histological analysis of organs and tissues. Each mouse received an intraperitoneal injection of 0.05 ml (0.75 mg/kg). Once animals were drowsy, their limbs were fixed with pins (25G ⅝ needles) through the skin onto a Styrofoam board. The abdomen of each animal was cleansed with ethanol and an incision made with sterile scissors in the skin at the level of the externo. The abdomen was then further cut to the right and to the left side. The externo was lifted with a pair of forceps and the diaphragm was opened through a diagonal incision, and a bilateral incision perpendicular to the rips was made to expose the thoracic cavity with the beating heart in the middle. The heart was held with forceps and the right atrium immediately cut to allow venous bleeding. The circulation of 10 ml PBS was permitted, followed by 40 ml formalin in the case of each mouse. The brain and spinal cord of each animal were carefully dissected out and placed in 10 ml formalin solution in a 50 ml Falcon® tube for 2 hours. The formalin solution was then changed by 10 ml sterile PBS and the material left at +4° C. overnight. The PBS solution was then changed again and the material was left at +4° C. for a few hours. The brain hemispheres and spinal cord were cut into approximately 0.5 cm slices and placed into plastic basquets compatible with the inclusion machine. Embedding of the brain and spinal cord in paraffin was done using an automatic Tissue Tek Vacuum Infiltration Processor E150/E300 (Miles Inc. Diagnostics) according to the program described below:

30 minutes in 50% ethanol
60 minutes in 70% ethanol
60 minutes in 70% ethanol
60 minutes in 80% ethanol
90 minutes in 80% ethanol
30 minutes in 96% ethanol
90 minutes in 96% ethanol
120 minutes in 96% ethanol
30 minutes in 100% xylene
60 minutes in 100% xylene Four 60 minute incubations in paraffin (Histosec, Merck 11609); last stage is for embedding.

All solutions were kept at 40° C. with the paraffin at 65° C. Once the tissue sections were ready, the brain and spinal cord sections were placed in the desired orientation on plastic chambers for paraffin block inclusion. The paraffin liquid was poured and allowed to cool quickly at 0° C. on a cool plate. Paraffin blocks were processed in a microtome for sectioning (5–10 μm). Sections were then mounted onto silane-treated glass slides (SuperFrost-Plus™, Menzel cat. no. 041300). Following mounting, slides were stored in a dust-free environment.

Cell Culture

Oli-neu: Mouse oligodendrocyte cell line (Oli-neu) cells were enriched via centrifugation and resuspended in Sato's medium (Trotter et al., 1989). Cells were cultured in 75-mL flasks at 37° C. and 5% $CO_2$ controlled conditions. Differentiation was performed with 1 mM dbcAMP added directly to cell culture medium. RNA was extracted using the Trizol Method (see below).

RNA Isolation

Total RNA was isolated from Oli-neu cells, cuprizone-treated mouse brain sections and mouse post-natal whole brains at different developmental stages using the Tri-ZOL® extraction protocol (Life Technologies AG, Basel, Switzerland). Poly(A)$^+$ RNA was prepared from total RNA samples using Qiagen OLIGOTEX™ columns (QIAGEN Inc., 28159 Stanford Avenue, Valencia, Calif. 91355, USA).

DGE Analysis Using cDNA Microarrays

Microarray experiments were done at Incyte Genomics (Incyte Genomics Inc., 3160, Porter Drive, Palo Alto, Calif. 94304, USA). DGE analysis was performed using Incyte's Mouse GEM™ 1 gene expression microarray (http://www.incyte.com/reagents/gem/products.shtml).

The Incyte chips used in these assays were loaded with cDNA molecules corresponding to 8734 genes, both known and unknown (EST sequences). Incyte's technology permitted micro samples of each of these genes to be spotted on a single array. Each cDNA molecule corresponding to a known gene or EST was 500–5000 bp in length. The Incyte specifications gave a detectable dynamic range of 2 to 2,000 pg for individual mRNA in a sample. The quantity of RNA required for each array experiment was 600 ng of poly(A)$^+$ RNA. Stated levels of detectable differential expression were given as ratios larger than 1.75.

Signal Normalization and Expression Level Determination

Ratios computed from the 2 fluorescence intensities provide quantitative measurement of the relative gene expression level in the 2 cell samples being analyzed. The ratios assigned to each gene are computed based on normalized expression levels. A normalization factor is computed by dividing the total expression of the second sample ($P_2$) by the total expression of the first sample ($P_1$). This factor is then applied to the expression level of each gene in $P_2$. Once this normalization step has been applied, the gene ratios are computed according to the following rule:

Let $E_1$ be the expression level of a given gene in sample 1 and let $E_2$ be the normalized expression level of the same gene in sample 2; if $E_2 > E_1$ then ratio=$E_2/E_1$, otherwise ratio=$-E_1/E_2$.

Since sample hybridization is performed simultaneously in competition, the Incyte chip technology is more precise in determining relative expression changes and becomes less reliable for the measurement of absolute expression levels. Nevertheless, it is possible to use these expression level values for comparing pairs of sample RNA populations that were not actually physically compared on a chip. Such in silico comparisons are less reliable but they can provide additional information on mechanisms that might apply to the systems being assayed.

Results

Models Used for Analysis of Differential Osteopontin Expression

Table IV shows the models, which were used for extraction of mRNA and chip hybridization (DGE analysis), as described above.

TABLE IV

Models used in DGE analysis

| Models | Treatments | Controls |
|---|---|---|
| 1. In vitro oligodendrocyte differentiation model | Oli-neu cells + dibutyryl-cAMP (6 hours) | Oli-neu cells (untreated) |
| | Oli-neu cells + dibutyryl-cAMP (6 days) | Oli-neu cells (untreated) |
| 2. In vivo Cuprizone demyelination/re-myelination model | Adult frontal brain + Cuprizone (3 weeks) | Untreated adult frontal brain |
| | Adult frontal brain + Cuprizone( 5 weeks) | Untreated adult frontal brain |
| | Adult frontal brain + Cuprizone (3 weeks) | Adult frontal brain + Cuprizone (5 weeks) |
| 3. Developmental myelination | Mouse post-natal day 10 (P10) cerebellum | Mouse post-natal day 2 (P2) cerebellum |

Positive control for DGE: Regulation of Myelin-specific genes.

As positive control, it was first tested if differential regulation of myelin-specific genes could be shown using DGE.

Table V shows the regulation observed for myelin-specific genes present on the Incyte microarrays. Differential expression values for each gene are reported from both the 3-week and 5-week time points of cuprizone treatment. This data is a positive control for verifying chip reliability. Since the regulation of myelin structural genes under our experimental conditions is well characterized, the observed expression of these genes measured on the chips could be used to indicate a) accuracy of the technology and b) reproducibility of our models.

TABLE V

In vivo regulation of myelin-specific genes in microarray assays on in vivo myelination models.

| Gene Name | Accession Number | Cup 3 w | Cup 5 w | P 2/10* |
|---|---|---|---|---|
| Myelin basic protein | AA059540 | 113.6 | 11.3 | +7.9 |
| Myelin vesicular protein/myelin and lymphocyte protein (MVP/MAL) | AA519027 | 33.5 | 11.7 | 0 |
| Cyclic nucleotide phosphodiesterase 1 (CNPase) | W63987 | 22.9 | 11.1 | +2.9 |

*Postnatal cerebellum day 2/10

The above table shows how some myelin-specific genes were regulated in the microarray assays performed on RNA from different in vivo models used to study demyelination, remyelination and developmental myelination. The changes in expression of these myelin-specific genes indicate how the process of myelination can be studied at the level of transcriptional regulation using microarrays.

After 3 weeks of cuprizone administration, the demyelinating effect of the treatment can be visualized in specific areas of the mouse brain. Therefore, at 3 weeks it was expected to observe the downmodulation of various genes associated with myelin synthesis and/or myelin maintenance. The downregulation of myelin-specific genes as observed via microarray serves as a confirmation of the accuracy and reliability of the experimental system. The data presented in Table V shows that the mRNA levels for MBP, downregulated 13.6-fold, and cyclic nucleotide-phosphodiesterase 1 (CNPase), downregulated 2.9-fold, were reduced at 3 weeks of cuprizone treatment compared to controls. However, the RNA levels for both these genes had returned to 1.3- and 1.1-fold below normal levels respectively after 5 weeks of cuprizone treatment, indicating that the biological system was attempting to establish remyelination by boosting synthesis of the structural myelin proteins.

Differential Regulation of Osteopontin:

On the chip, Osteopontin was upregulated at 3w (+2.2) and 5w (+2.8) Cuprizone.

Example 2

Confirmation of Differential Gene Expression of Osteopontin by Real-Time Quantitative Reverse Transcriptase (RT)-PCR Assay (TaqMan®)

Methods cDNA Template Generation

The cDNA templates for TaqMan® analysis were generated from total RNA samples via reverse-transcription (RT) using the TaqMan® reverse transcription reagents (P/N N808–0234). All RT reactions were performed in a 100-µl volume containing: 10 µl TaqMan RT buffer, 22 µl 25 mM $MgCl_2$ solution (5.5 mM), 20 µl deoxyNTPs mixture (500 µM of each dNTP), 5 µl random hexamers (2.5 µM), 2 µl RNase inhibitor (0.4 U/µl), 2.5 µl. MultiScribe™ Reverse Transcriptase (1.25 U/µl) and 38.5 µl RNA sample (1 µg total) in RNase-free $H_2O$. Reactions were performed on an Eppendorf MasterCycler at 25° C. for 10 min (incubation step), 48° C. for 30 min (reverse transcription), and 95° C. for 5 min (inactivation step). All synthesized cDNAs were stored at −20° C. in 20 µl volumes.

Primer Design and Verification

SYBR Green Real Time PCR forward and reverse primers for all confirmed genes and GAPDH (house keeping control) were designed using the Primer Express™ software from PE Biosystems according to the published sequences and ordered at 0.02 µM concentration from Interactiva (Interactiva: The Virtual Laboratory, Sedanstrasse 10, D-89077 Ulm). The specificity and optimal primer concentrations were tested for each primer set. Potential genomic DNA contamination was monitored by performing PCR reactions on negative control cDNA samples that had been subjected to reverse transcription reactions in the absence of the RT enzyme. Absence of non-specific amplification was confirmed by analyzing the PCR products via agarose gel electrophoresis on 3.5% MetaPhor gels or pre-cast NuSieve® 4% gels.

Table VI indicates the sequences of the gene-specific primers designed for performing TaqMan® analysis to confirm differential expression of genes shown to be differentially regulated on microarrays. The names of the genes corresponding to each primer pair and the GenBank accession number of the sequence used to design each primer with the PrimerExpress™ software are also included.

TABLE VI

Primers used for RT-PCR analysis

| Gene Name | Acces. Number | TaqMan® OLIGO NAME | TaqMan® OLIGO SEQUENCE | SEQ ID NO |
|---|---|---|---|---|
| Secreted phosphoprotein 1 (osteopontin) | AA 108928 | Osteopontin-166F Osteopontin-235R | AGCCTGCACCCAGATCCTATAG GCGCAAGGAGATTCTGCTTCT | 4 5 |

TaqMan Reactions

SYBR Green Real-Time PCR was performed with 5 µl/well of RT-products (0.5 ng total RNA), 25 µl/well of SYBR Green PCR master mix, (Applied Biosystems, CA, USA) with AmpErase Uracil N-Glycosylase (UNG) (0.5 Unit/well) and 20 µl of primers (300 nM). PCR was performed at 50° C. for 2 min (for AmpErase UNG incubation to eliminate any potential carryover by removing uracil incorporated into the PCR products generated from previous TaqMan runs), 95° C. for 10 min (for AmpliTaq Gold activation). Then samples were run for 40 cycles at 95° C. for 15 sec, 60° C. for 1 min on the ABI PRISM® 7700 Sequence Detection. System. The reverse-transcribed cDNA samples were thus amplified and their $C_T$ (threshold cycle) values were determined. All $C_T$ values were normalized to the housekeeping gene GAPDH. Where possible, samples were run in duplicate or triplicate to gauge the reproducibility of the result. A single specific DNA band for all confirmed genes and GAPDH was observed upon electrophoretic analysis.

Calculation of Gene Regulation Via Cycle Threshold ($C_T$)

The principle of real-time detection using the SYBR Green PCR master mix is based upon the direct detection of PCR product by measuring the increase in fluorescence created by the binding of SYBR Green dye to double-stranded DNA. This permits quantification of the relative increase in a gene-specific amplification product based on PCR growth curves.

Measurement of specific cDNA species relative to a control sample is performed by quantification of cDNA converted from a messenger RNA corresponding to the specific gene relative to a calibrator sample serving as a physiological reference. The calibration is provided by a sample from a control or untreated condition. Relative quantification of the cDNA species is completed via normalization to an endogenous control (in this case, GAPDH) to account for any variability in the initial concentration and quality of the total RNA used to generate template cDNAs and in conversion efficiency of reverse transcription reactions. Calculation of relative quantitation values was performed by taking the mean $C_T$ value for the replicate reactions run for each sample, calculating the difference ($\Delta C_T$) in mean $C_T$ between target samples and the endogenous controls, subtracting the mean $C_T$ of the calibrator for the target from the $\Delta C_T$ of that target ($\Delta\Delta C_T$) and finally expressing the relative quantification value for the target as $2^{-\Delta\Delta Ct}$ to gauge the extent of the up- or down-regulation in gene expression.

Normalization of Fluorescence Signals in TaqMan® Reactions

SYBR Green-dsDNA complex fluorescence signals are normalized to the passive reference or negative control reactions containing no template DNA. Normalization was performed via division of the emission intensity of SYBR Green-dsDNA complex in the experimental reaction by the emission intensity of the passive reference. This yields the $R_n$ (normalized reporter) ratio for the reaction:

$R_n^+ = R_n$ value of a reaction containing all components including template DNA $R_n^- = R_n$ value of an unreacted sample (no template DNA)

$\Delta R_n = (R_n^+) - (R_n^-)$ where:

$R_n^+$ = (emission intensity of SYBR Green-dsDNA complex)/PCR with template (emission intensity of passive reference)

$R_n^-$ = (emission intensity of SYBR Green-dsDNA complex)/No template (emission intensity of passive reference)

Calculation of Fold Regulation from Cycle Threshold ($C_T$) Values $\Delta R_n$ represents the magnitude of the signal generated by the given set of PCR conditions for a specific reaction. The cycle threshold parameter constitutes a measurement of the relative increase in amplification of the gene-specific product, which represents relative abundance of a specific transcript in an experimental cDNA population. It is fixed as the cycle point at which a statistically significant increase in $\Delta R_n$ is first detected. The threshold is defined as the average standard deviation of $R_n$ for the early cycles, multiplied by an adjustable factor. The cycle threshold parameter is used for quantitation of differential gene expression. Specific values are calculated for each gene-specific growth curve based on the point or cycle at which an increase above background fluorescence intensity is detected.

All calculation of relative quantitation values was performed by taking the mean $C_T$ value for the replicate reactions run for each sample, calculating the difference ($\Delta C_T$) in mean $C_T$ between target samples and the endogenous controls and subtracting the mean $C_T$ of the calibrator for the target from the $\Delta C_T$ of that target ($\Delta\Delta C_T$). Finally, the relative quantification value for the target was expressed as $2^{-\Delta\Delta Ct}$ to gauge the extent of up- or down-regulation in gene expression.

Results

Real-time quantitative reverse transcriptase (RT)-PCR (TaqMan) provides a sensitive and reliable approach to confirming and elucidating changes in gene expression. The TaqMan sequence detector (ABI PRISM® 7700 Sequence Detection System, Applied Biosystems, Foster City, Calif.) integrates a PCR-based assay with hardware/software instrumentation to provide a system for high-throughput quantification of nucleic acid sequences. This combines thermal cycling, fluorescence detection, and application-specific software to permit the cycle-by-cycle detection of the increase in the amount of a specific PCR product.

Expression of several highly regulated genes pinpointed via microarray analysis was verified using the TaqMan® platform. In each case, as far as possible, a time course for each model system being used was included. This permitted more data to be gathered regarding how specific genes behaved during a complete process:

Changes in gene expression could be quantitated via TaqMan® via direct detection of an increase in the PCR product via measurement of fluorescence created by the binding of SYBR Green dye to double-stranded DNA, represented by amplification products specific to the gene being assayed. Measurement of specific cDNA species relative to a control sample is performed by quantification of cDNA converted from a messenger RNA corresponding to the specific gene relative to a calibrator sample serving as a physiological reference. Calibration is provided by a sample from a control or untreated condition. Relative quantification of the cDNA species is calculated with normalization to GAPDH to account for any variability in initial concentration and quality of the total RNA used to generate template cDNAs and in the conversion efficiency of reverse transcription reactions.

Expression of secreted phosphoprotein 1 (osteopontin) gene was analyzed in a time course study spanning the demyelination/remyelination paradigm associated with the cuprizone model.

Results of TaqMan experiments for osteopontin expression in the cuprizone remyelination model are shown in FIG. 1(A). The mRNA levels of osteopontin were found to be upregulated 18 fold in mouse frontal brains after 3 weeks of cuprizone administration (3w. Cup.), and 25-fold after 5 weeks of treatment (5w. Cup.).

Osteopontin expression was downregulated after 1, 3 and 6 weeks of regeneration further to 5 weeks of cuprizone treatment (5w. cup.+1w. 3w. and 6w.). These findings indicate an important role of osteopontin in the demyelinating and remyelination phase of the model, since remyelination starts when demyelination is still ongoing.

FIG. 1(B) shows the results of osteopontin expression levels in developing Cerebellum. Osteopontin mRNA is transiently upregulated during early postnatal development, days C4 to C8, which is the time period of initiation of myelination in the cerebellum.

Microarray results had indicated upregulation of osteopontin in mouse frontal brains during cuprizone treatment. This analysis extends the profile of osteopontin expression to include both the demyelinating and remyelinating phases of cuprizone treatment, and shows that the osteopontin expression profile peaks during the demyelinating phase of cuprizone treatment, and during the recovery period returns to near baseline levels The results are shown in Table VII below.

The results of TaqMan® analysis of osteopontin expression confirmed its upregulation in the brains of mice fed with cuprizone for 3 and 5 weeks.

TABLE VII

TaqMan® analysis of osteopontin regulation in the Cuprizone model

| Tissue type | Experiment | Expression levels | regulation |
| --- | --- | --- | --- |
| Frontal brain | Cup. control | 1.00 | Control level |
| Frontal brain | Cup. control | −1.32 | down |
| Frontal brain | 3 w. Cup. | 17.51 | up |
| Frontal brain | 3 w. Cup. | 23.43 | up |
| Frontal brain | 5 w. Cup. | 20.25 | up |
| Frontal brain | 5 w. Cup. | 23.43 | up |
| Frontal brain | 5 w. Cup. + 1 w. R. | 1.79 | up |
| Frontal brain | 5 w. Cup. + 1 w. R. | 3.32 | up |
| Frontal brain | 5 w. Cup. + 3 w. R. | 2.95 | up |
| Frontal brain | 5 w. Cup. + 3 w. R. | 4.56 | up |
| Frontal brain | 5 w. Cup. + 5 w. R. | −1.16 | down |
| Frontal brain | 5 w. Cup. + 5 w. R. | 1.04 | Control level |
| Frontal brain | 5 w. Cup. + 5 w. R. | 1.07 | Control level |

Example 3

Confirmation of Differential Osteopontin Expression by Northern Blot

Methods

Blot Preparation

For specific genes, tissue specificity of expression was assayed using mouse Multi-Tissue Northern blots (Clontech Labs, 1020 East Meadow Circle, Palo Alto, Calif.). These contained 2 μg of poly(A)$^+$ RNA per lane from different tissues of the adult mouse. Separate blots were prepared for analysis of differential gene expression in both in vitro and in vivo situations. RNA isolated from the brains of cuprizone treated mice at 3 weeks, 5 weeks and the 1, 3 and 6-week time points during the recovery process (up to 6 weeks) was used on one set of blots. Whole brain RNA from different postnatal day stages was used on a second set. Finally, a time-course series of RNAs was prepared from Oli-neu cells grown in culture and treated for different lengths of time with dibutyryl-cAMP. This RNA was used to prepare a third set of blots. New blots were used with each gene-specific probe to ensure maximal detection efficiency and minimize variations in results due to uneven stripping after hybridization. All blots were hybridized twice, first with a probe against the gene of interest and then, following stripping, with a probe against mouse glyceraldehyde-3-phosphate (mGAPDH) to control for variations in RNA loading.

RNA (10 μg/well) was loaded onto a 1.2% denaturing agarose gel containing formaldehyde and 5×MOPS (209.27 g 3-(N-morpholino)-propanesulfonic acid, 20.5 g sodium acetate, 50 mL 0.5 M EDTA pH 8.0 in 5 L with sterile $H_2O$, to pH. 7.0 with 12 M NaOH). Each RNA sample was mixed with 2 μl ethidium bromide (0.01 mg/ml), 2 μl 5×3-(N-morpholino)propanesulfonic acid (MOPS), 3.5 μl 37% formaldehyde and 10 μl formamide. Samples were then heated at 65° C. for 10 minutes and quick-chilled on ice. Two microliters RNA loading buffer (50% glycerol, 1 mM EDTA, 0.4% bromophenol blue and 0.4% xylene cyanol dye) was added to each sample immediately prior to loading on the gel.

Each gel run was ~3 hours in a 1×MOPS running buffer (1L=330 mL 37% formaldehyde, 400 mL 5×MOPS, 270 mL DEPC-treated $H_2O$) at 5 V cm$^{-1}$ (gel length). This was followed by an overnight RNA transfer to a positively charged nylon membrane (Hybond™-N, Amersham Life Sciences, Amersham Place, Little Chalfont, Buckinghamshire, England HP7 9NA) using SSC solution as described (Terry Brown, Unit 4.9, Current Protocols, 1993 [ed. F. M. Ausubel, R. Brent, R. E. Kingston, D. D. Moore. J. G. Seidman, J. A. Smith, and K. Struhl]). The RNA transfer efficiency was checked by viewing the membrane and flattened gel under UV light. RNAs were cross-linked to the membrane via Stratalinker (Stratagene, USA). Blots were stored between sheets of Whatman 3 MM filter paper at room temperature prior to hybridization.

Probe Preparation

Radioactive $^{32}$P-labeled probes were prepared using gel-purified restriction fragments of cDNA clones (~500>800 bp in length) corresponding to genes of interest. DNA fragments were randomly labeled to a specific activity >10$^9$ cpm ml$^{-1}$ with $^{32}$P-dCTP using the HighPrime™ labeling system (Roche Diagnostics AG, Industriestraβe 7, 6343 Rotkreuz, Switzerland). Unincorporated $^{32}$P-dCTP was removed via gravity-based elution of the probe mixture through a Pharmacia NAP™-5 column containing Sephadex® G-25

Medium (DNA Grade in distilled water containing 0.15% Kathon® CG/ICP Biocide®).

Hybridization and Signal Detection

Probe hybridization was performed using ExpressHyb™ (Clontech Labs, 1020 East Meadow Circle, Palo Alto, Calif.) according to manufacturer specifications. Blots were exposed following hybridization to Hyperfilm™ MP (Amersham Pharmacia Biotech, England) at −80° C. in autoradiography cassettes. Stripping the probe following exposure was performed by incubating the blot for 10 minutes in sterile $H_2O$/0.5% SDS solution at 90–100° C. and then allowing the blot to cool for 10 minutes. Stripped membranes were sealed in plastic and stored at −20° C. until needed for reprobing.

Results

Northern blot analysis has previously been employed as a secondary confirmation technique in large-scale differential gene expression studies (Chang et al, 2000). Its sensitivity and accuracy permits analysis of not only tissue specificity of expression for a given gene of interest but also the magnitude of differential regulation between experimental and control conditions. This makes it a reliable method for confirming DGE results obtained via microarray analysis. Also, Northern blots provide information relating to transcript sizes and possible alternative splice isoforms corresponding to the gene of interest.

Custom Northern blots were prepared using RNA isolated from the brains of cuprizone-treated and control mice. These were probed with radioactively labeled DNA fragments from clones sent to us by Incyte Genomics. The ability of Northern blots to reproduce the results observed via TaqMan® analysis of gene expression was verified using a radioactively labeled probe against mouse osteopontin hybridized to a blot of RNAs isolated from the brains of mice treated with cuprizone. In this manner, it was possible to compare the Northern blot analysis to the TaqMan® analysis of the expression of osteopontin in the cuprizone model.

Figure 3:
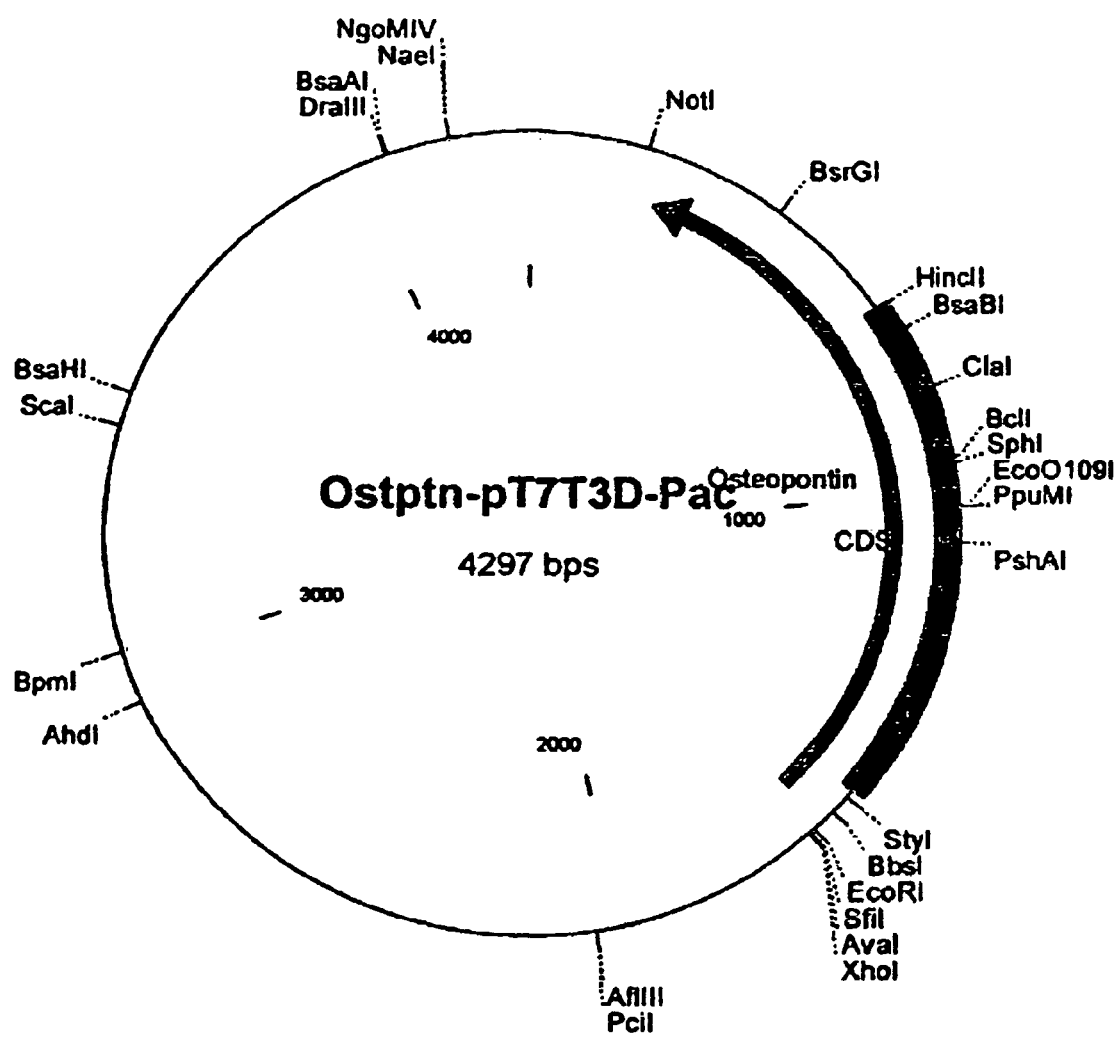
FIG. 3 schematically depicts the plasmid Pac containing the coding sequence for osteopontin.

FIG. 3 shows the open reading frame for mouse osteopontin inserted into the pT7T3D-Pac vector as ordered from Incyte Genomics. The grey region is the coding sequence and the arrow represents the complete cDNA for osteopontin. The clone insert was flanked by EcoRI and NotI restriction sites. To make a probe for use in Northern blotting in order to analyze tissue expression of this gene, an 893-bp fragment was cut from the clone using the HincII and StyI restriction enzymes. This fragment was gel-purified and labeled for use as a probe.

The expression of mouse osteopontin was ascertained via Northern blot analysis using a custom blot prepared with RNAs from the brains of mice from each stage in the cuprizone model, including recovery and untreated controls. The blot was probed first with a radioactively labeled fragment of the mouse osteopontin cDNA, stripped following exposure, and then reprobed with a radioactively labeled fragment of mouse GAPDH. This was used as a positive control to account for differences in observed expression levels based on variations in the overall amounts of RNA in each lane on the blot.

The expression of osteopontin in the brains of cuprizone-treated mice reaches a peak at 3 and 5 weeks of Cuprizone feeding, with slightly higher expression at 5 weeks. During the recovery phase, levels of osteopontin mRNA diminish relatively rapidly, with an appreciable reduction in expression 1 week after the cessation of cuprizone feeding. The levels of osteopontin mRNA return to approximately normal levels after 6 weeks recovery. This is qualitatively comparable to the results obtained in TaqMan® analysis of osteopontin expression in the cuprizone model (see FIG. 1A).

Example 4

Regulation of Osteopontin in Oli-Neu Cells

Figure 4:
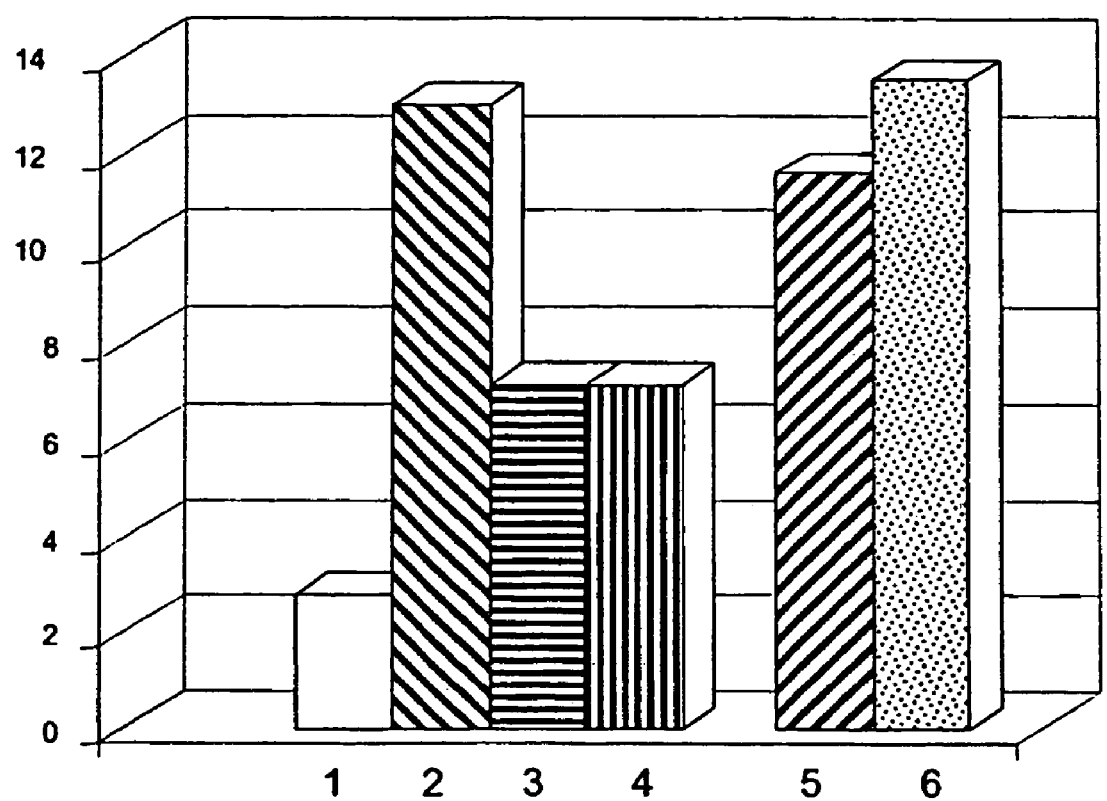
FIG. 4 shows a histogram illustrating the fold upregulation of osteopontin mRNA in oligodendrocyte cell line oli-neu treated with cAMP for 6 h (1), 2 d (2), 6 d (3) or 10 d (4) as compared to control. Columns 5 and 6 depict the osteopontin mRNA levels from a cuprizone experiment. (5): 3 weeks of cuprizone treatment, (6): 5 weeks of cuprizone treatment.
Figure 5:
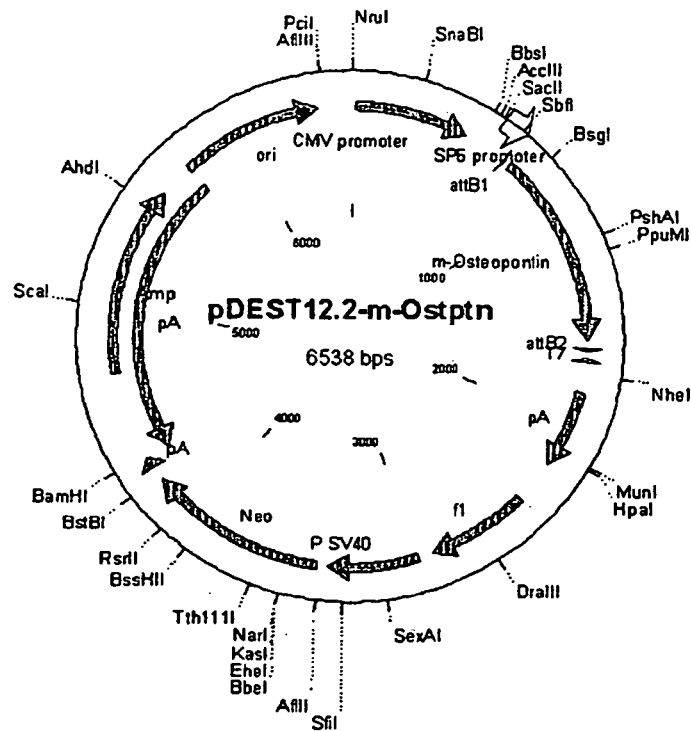
FIG. 5 shows schematically the plasmid pDEST 12.2 comprising the osteopontin coding sequence.
Figure 6:
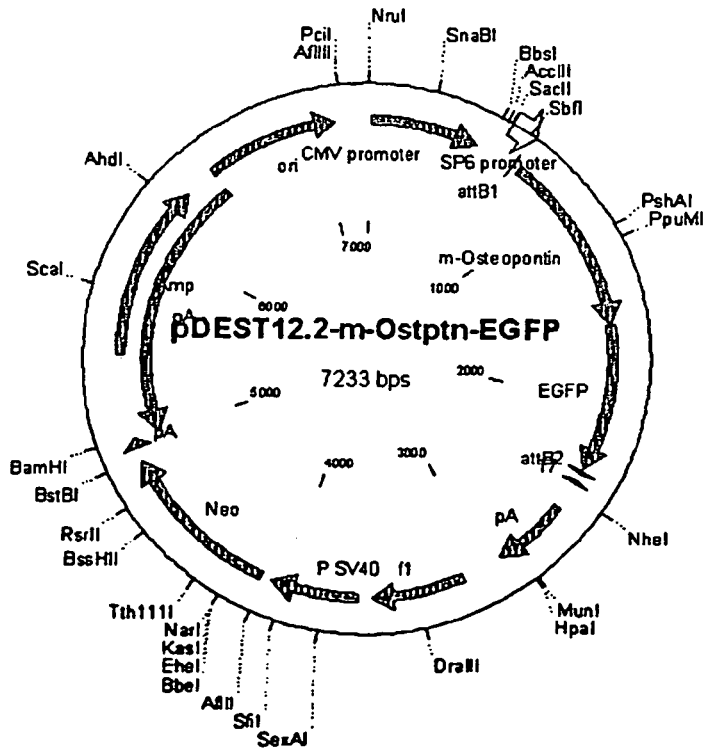
FIG. 6 shows schematically the plasmid pDEST 12.2 comprising the osteopontin coding sequence plus the coding sequence of EGFP, a fluorescent marker.
Figure 7:
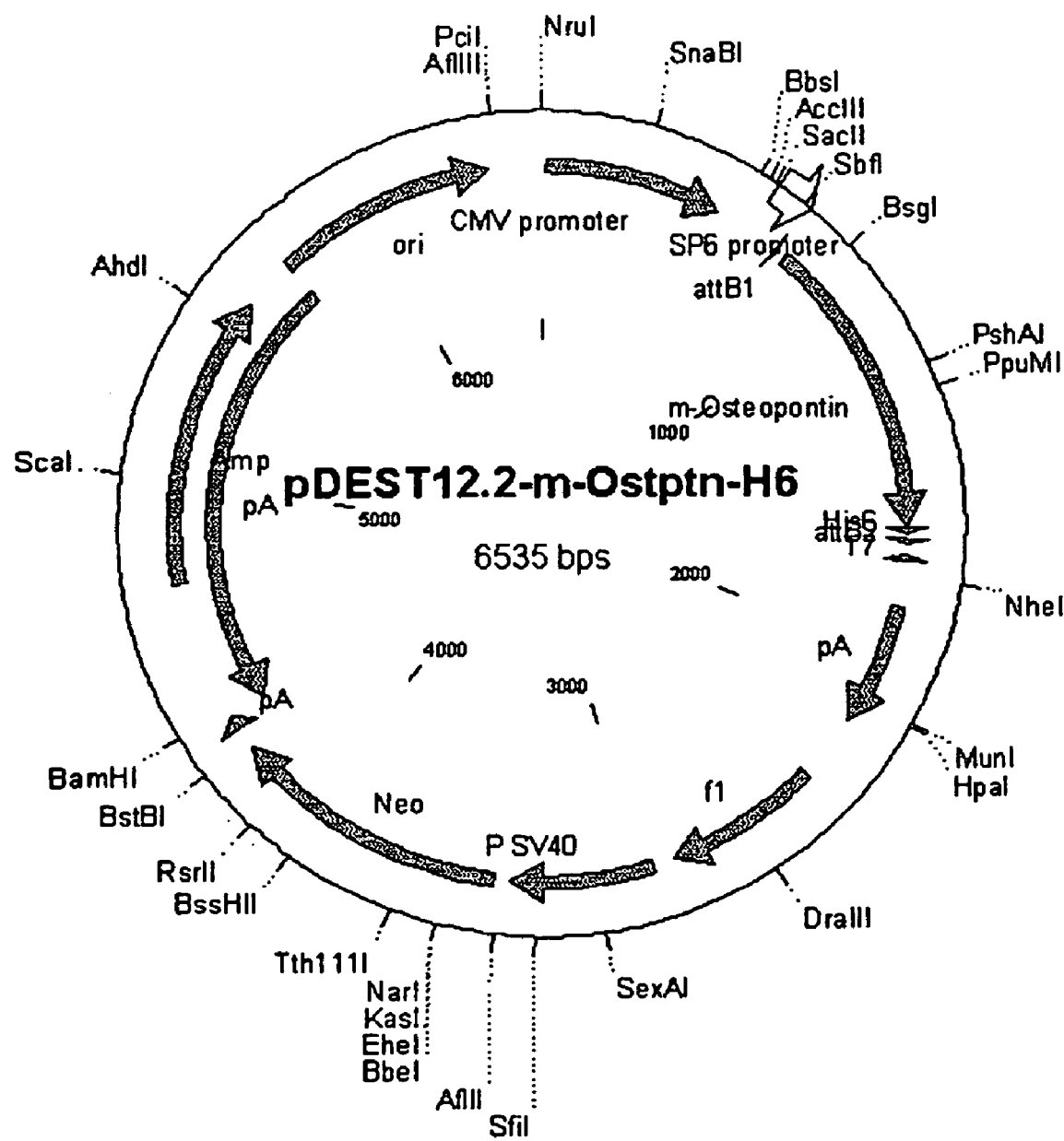
FIG. 7 shows schematically the plasmid pDEST 12.2 comprising the osteopontin coding sequence with a HIS-tag.

Osteopontin expression in oligodendrocytes (oli-neu) treated with cAMP was measured by TaqMan analysis. The results are shown in FIG. 4. Columns 1 to 4 show the results obtained in the oligodendrocytes. As compared to control (value=1), 6 h of treatment with cAMP (col. 1) led to an upregulation of osteopontin mRNA. After 2 d of cAMP treatment (col. 2), a 12 times upregulation was measured. Prolonged treatment for 6 to 10 d (col. 3,4) led to lower levels of osteopontin mRNA. A comparison to the regulation of osteopontin mRNA in the cuprizone model (col. 5, 6) showed that the upregulation of osteopontin after 3 and 5 weeks of curpizone in frontal brain was comparable to upregulation in oligodendrocytes after 2 d of cAMP treatment Example 5

Expression of Osteopontin in Oligodendrocytes

Method

Oli-neu cells were transiently transfected following the calcium phosphate precipitation method. Briefly, oli-neu cells from the exponential growth phase were seeded (10e5/ml) into 6-well plate the day before the transfection is performed. A solution of 100 μl of 250 mM CaCl2 was mixed with 5 μg of plasmid DNA. An equal volume (100 μl) of 2×HEPES solution (140 mM NaCl, 50 mM HEPES pH 7.05) supplemented with phosphate from 300 mM stock solution of Na2HPO4 and NaH2PO4 at pH 7.05 was added to the Ca/DNA solution. Exactly one minute later, the mixture was gently added to the culture plate and incubated for 4 hours at 37° C. in $CO_2$ incubator. After this time, the medium was replaced with fresh medium and the cells were then incubated for 24–72 hours before harvesting and analyzing by Western blotting.

Results

Different mouse osteopontin constructs, in pDEST12.2 vector (pDEST12.2-osteopontin-EGFP, pDEST12.2osteopontin-His6, pDEST12.2-osteopontin, see FIGS. 4 to 7, and pCIE-EGFP as control plasmid) were transfected in oli-neu cells. The protein was produced and secreted by the cells as detected by specific commercial antibodies (R&D Systems, AF808). The EGFP tagged construct made the monitoring of the transfection easier and 24 hours after the transfection, a specific change of cell morphology (increase in oligodendrocyte processes) could be detected in comparison with the pCIEGFP control (not shown), which indicated that osteopontin drives the mouse oligodendrocyte cell line oli-neu toward a more mature morphological phenotype. The morphology presented by osteopontin transfected oli-neu cells was very similar to the morphology of a myelinating oligodendrocyte.

These results demonstrate that the expression of osteopontin in oligodendrocytes is beneficial to drive these cells towards myelination, and therefore indicate a beneficial effect of osteopontin in diseases linked to oligodendrocyte dysfunction.

Example 6

Expression of Osteopontin Protein in Specific Regions of the Brain in the Cuprizone Model Osteopontin immunohistochemistry was performed on various time points during de- and remyelination in the Cuprizone model. Strong signals were found in the demyelinated corpus callosum and striatum bundles at 5 weeks of cuprizone treatment, a time point associated with prominent microglia recruitment to the sites of demyelination. In order to visualize the activated microglia cells, a CD68 staining at consecutive sections was carried out, and the similar expression patterns suggest microglia expression of osteopontin.

Interestingly, osteopontin was also found in cells lining the anterior ventricles. This region was described as the adult subventricular zone bearing multipotent stem cells for the production of neurons, astrocytes and oligodendrocytes. Double stainings with NG2, PSA-NCAM, PDGFα receptor will be performed in order to determine the oligodendrocyte precursor cells expressing osteopontin.

Example 7

Effects of Osteopontin Protein on Oligodendrocyte Proliferation

A murine primary oligodendrocyte (oligodendroglial) cell line immortalized with the t-neu oncogene ("oli-neu" cell line) was used in this experiment. The establishment and properties of the oli-neu cell line as well as the culturing conditions are described in Jung et al. (1995).

The aim of this study was the measurement of the effects of OPN on oligodendrocyte proliferation in a oli-neu proliferation assay. Cells were plated subconfluently. They were starved for 24 hours in insulin free medium before treatment with either control or recombinant proteins. Cell numbers were quantitated with Alamar blue, giving a fluorescent read out. Calculations for potentiation were based on the comparison to the IGF1 (control) standard curve. The calculations for inhibition of proliferation were based on the comparison to the dbcAMP standard curve.

Material

Equipments and Softwares

Wallac Victor 2 multilabel counter (excitation at 530–560 nm, emission at 590 nm)

Graph Pad Prism software

Reagents oli-neu cell line (Eur J Neuro 7:125–1265 (1995))

Alamar blue (BioSourceIntl. Inc., Camarillo, Calif. 93012)

Components for Sato medium were as follows:

| Product | Supplier | Stock | μl per 500 ml |
|---|---|---|---|
| DMEM | Seromed F0435 | 500 ml | |
| Transferrin | Sigma T-2252 | 100 mg/ml (1 mg in 10 ml PBS) | 50 |
| Sodium Selenite | Sigma S-9133 | 1 mg/2.56 ml PBS | 50 |
| Insulin | Sigma I-1882 | 10 mg/ml (100 mg/10 ml PBS) | 500 |
| Putrescine | Sigma P-7505 | 80.5 mg/ml (PBS) | 500 |
| Progesterone | Sigma P-0130 | 0.62 mg/ml (EtOH) | 50 |
| TIT (Triiodothyronine) | Sigma T-5516 | 1.7 mg/ml (1/3 HCl 1 N + 2/3 EtOH) | 100 |
| L-Thyroxine | Sigma T-0397 | 2.88 mg/ml + 1 drop NaOH 1 N | 100 |
| L-Glutamine | Gibco 25030-024 | 200 mM | 5000 |
| Gentamycin | Gibco 15750-037 | 50 mg/ml | 250 |
| Sodium Bicarbonate | Gibco 25080-052 | 7.50% | 13000 |
| Horse Serum | | | 5000 |

BioCoat flat bottom plate, coated with poly D lysine (356461) from Becton Dickinson); R3-IGF1 (I1146 from Sigma); DbcAMP (D-0627 from Sigma)

Method

Cultivation of Cells for in Vitro Bioassay

Oli-neu cells are adherent cells growing on Poly-L-Lysine substrate Cells were plated on BioCoatTM poly-lysine pre-coated 96 well plates. The cells were split 2–3×/week. In order to split, they were first washed with PBS and then detached with PBS plus 1 mMEDTA. Cells were grown in a humidified 10% CO2 incubator.

The freezing medium used was Sato Medium with 20% FCS and 10% DMSO. In this experiment, oli-neu cells of no higher than passage 16 were used. Cells were used at a final concentration of 4000 cells per well in 96 well plate after 24 starvation in Sato medium minus insulin.

Alamar Blue Staining

After 48 hrs in CO2 incubator, 10 μl of Alamar Blue stock was added to the wells and incubated for additional 2.5 hours. The fluorescence was monitored at 530–560 nm excitation and 590 nm emission wave length. Plates could be read up to 4 hours and up to 1 million relative fluorescence units.

Experimental Design

As controls, 100 ng/ml R3-IGF-1 (positive control), or 1 mM dbcAMP (negative control), or medium without insulin, or 100 nM of boiled OPN, were used. Experimental samples were 1 nM, 10 pM, 0.1 pM, 0.01 pM or 100 nM of recombinant osteopontin. Controls and experimental samples were diluted to the desired concentrations with a final volume of 50 μl in Sato medium minus insulin and added to wells. Oli-neu cells were grown in insulin-free medium for 24 hours, and then treated with controls or experimental samples for 48 hours. Detached oli-neu cells that were freshly starved for 24 hours in medium minus insulin, were harvested from the growth flask with PBS plus 1 mM EDTA. The cells were prepared at 300,000 cells per ml and added 50 μl per well. Then, the cells were incubated 48 hours at 37° C. in a humidified CO2 incubator. 10 μl alamar blue were added and the cells were returned to incubator for 2.5 hours. Then, 70 µl from each well were transferred to black 96 well plates and the fluorescence was measured immediately.

The proliferation of undifferentiated oli-neu cells was measured after 24 hours in response to different amounts of osteopontin, which was produced using the insect cells (BacOPN), or a mammalian expression system (HEK-OPN). The growth rate was quantified by measuring the cellular metabolic activity with a fluorometric/colorimetric growth indicator, Alamar Blue. This agent contains an oxidation-reduction indicator that shows both fluorescence and changes its color in response to chemical reduction of growth medium resulting from cell growth. The agent and assay used are described in Ahmed et al. (1994) and the U.S. Pat. No. 5,501,959.

Results

Figure 8:
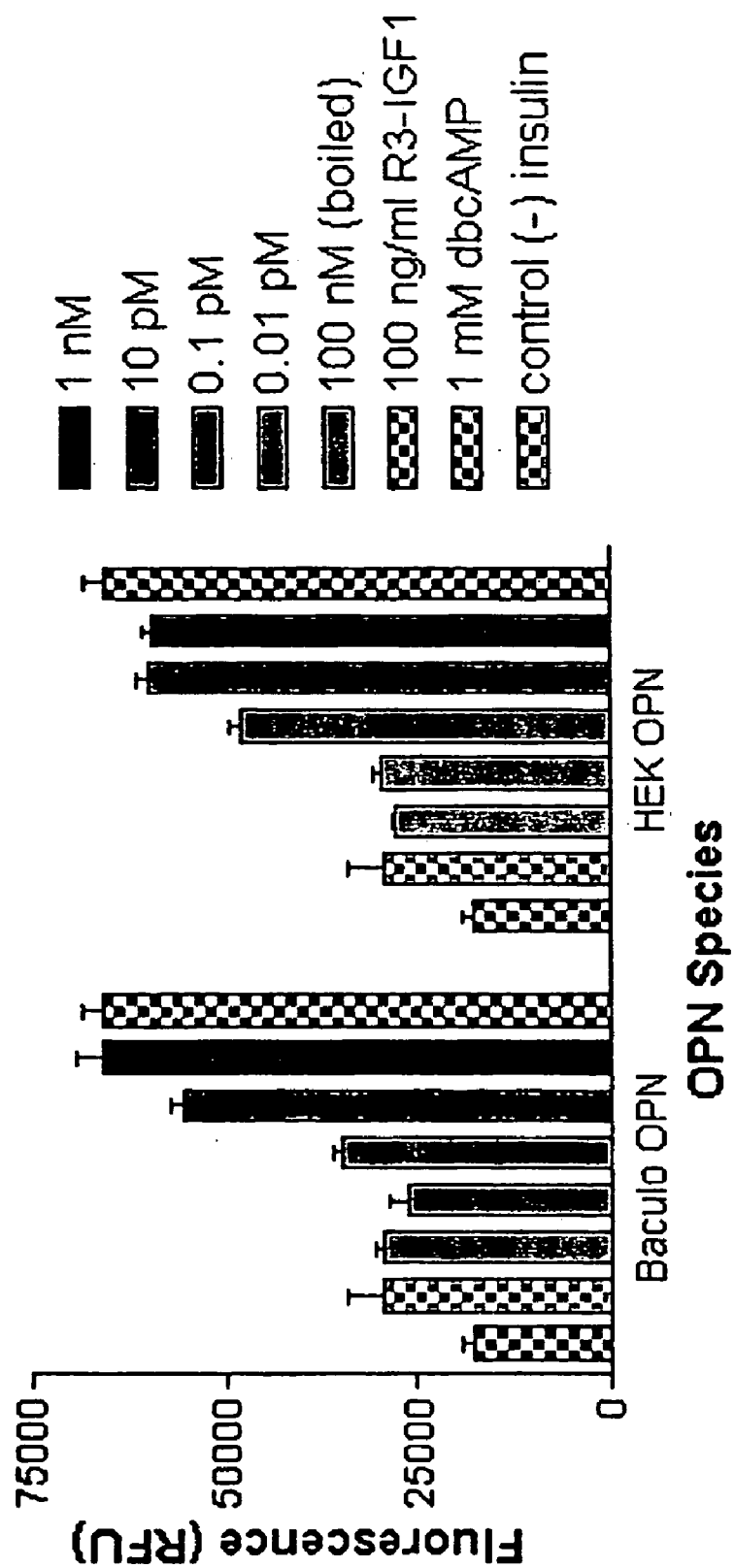
FIG. 8 shows the proliferation of oli-neu cells after insulin starvation and 24 hrs treatment with osteopontin expressed in baculovirus (Baculo-OPN) or HEK cell expressed osteopontin (HEK-OPN). Read-out is fluorescence of Alamar Blue, a dye staining living cells.
Figure 9:
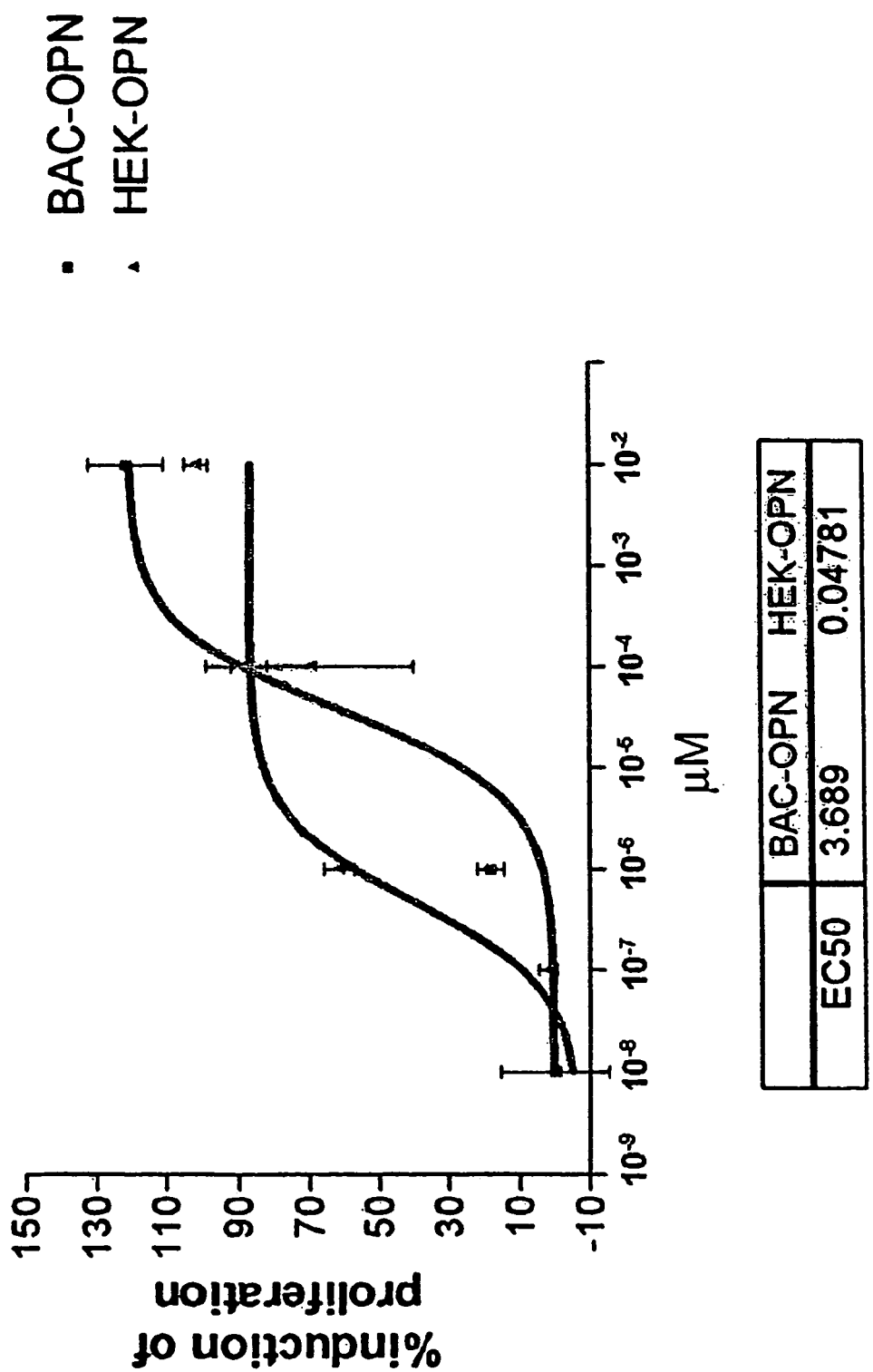
FIG. 9 shows the dose response curve of proliferation of insulin starved oli-neu cells after 24 hours of treatment with baculovirus expressed osteopontin (BAC-OPN) or HEK cell expressed osteopontin (HEK-OPN).
Figure 10:
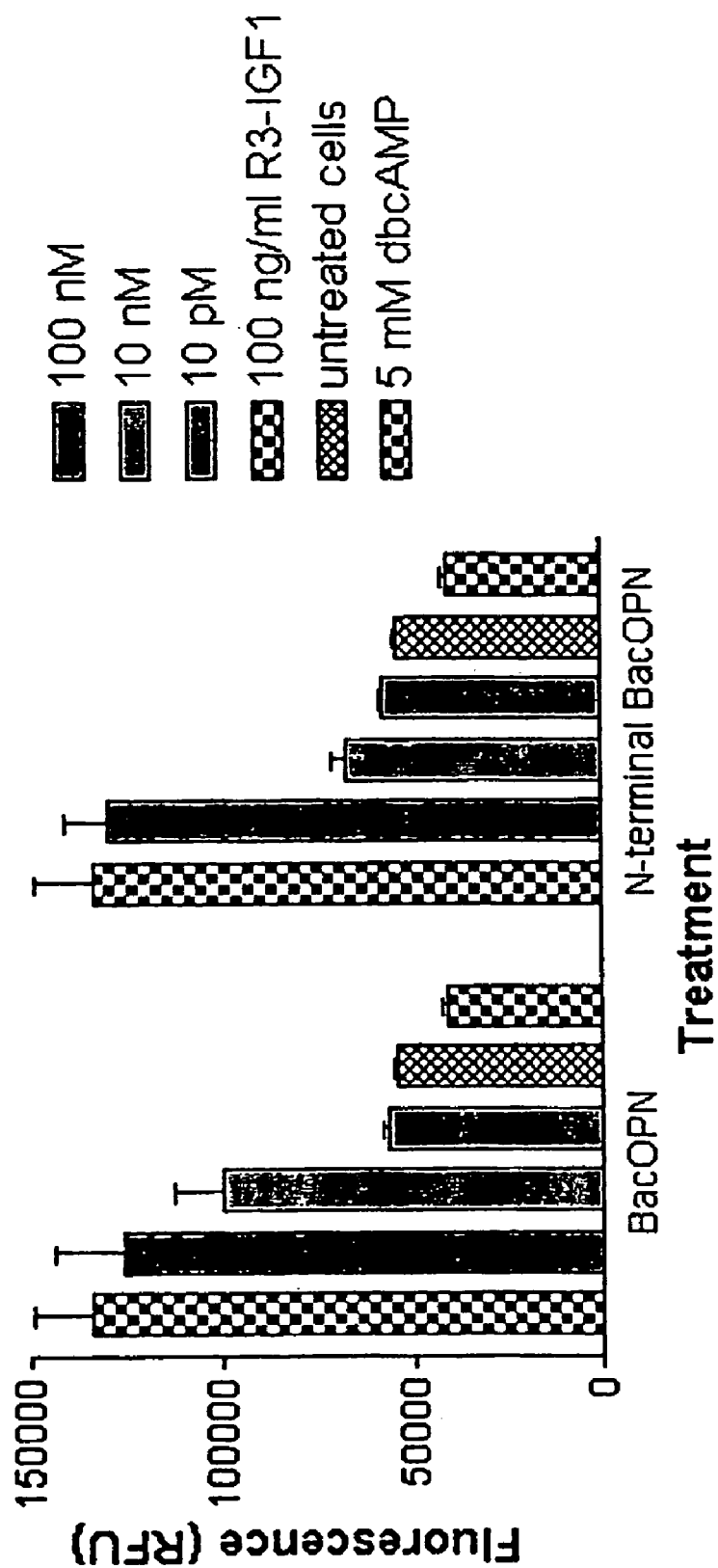
FIG. 10 shows the proliferation of oli-neu cells after insulin starvation and treatment with either full-length baculovirus expressed osteopontin (BacOPN) or an N-terminal fragment of osteopontin (N-terminal BacOPN).

The results are shown in FIGS. 8 to 10.

A dose response was observed with recombinant osteopontin, both baculovirus expressed and HEK cell expressed. Degeneration of the protein by boiling destroyed the biological activity, as expected. Addition of baculovirus expressed osteopontin (BacOPN) and HEK cell expressed OPN (HEK OPN) resulted in a dose-dependent increase of cell proliferation (FIG. 8) with a IC50 for BacOPn of 3.7 nM and 0.05 nM for HekOPN (FIG. 9). In addition, an N-terminal OPN construct corresponding to amino acids 1 to 168 of OPN isoform a (see FIG. 2, N-term. OPN-a) was expressed in insect cells. The purified protein was tested in the proliferation assay in comparison to the full-length protein. The truncated protein was active (10 nM, 100 nM), see FIG. 10.

Example 8

Figure 11:
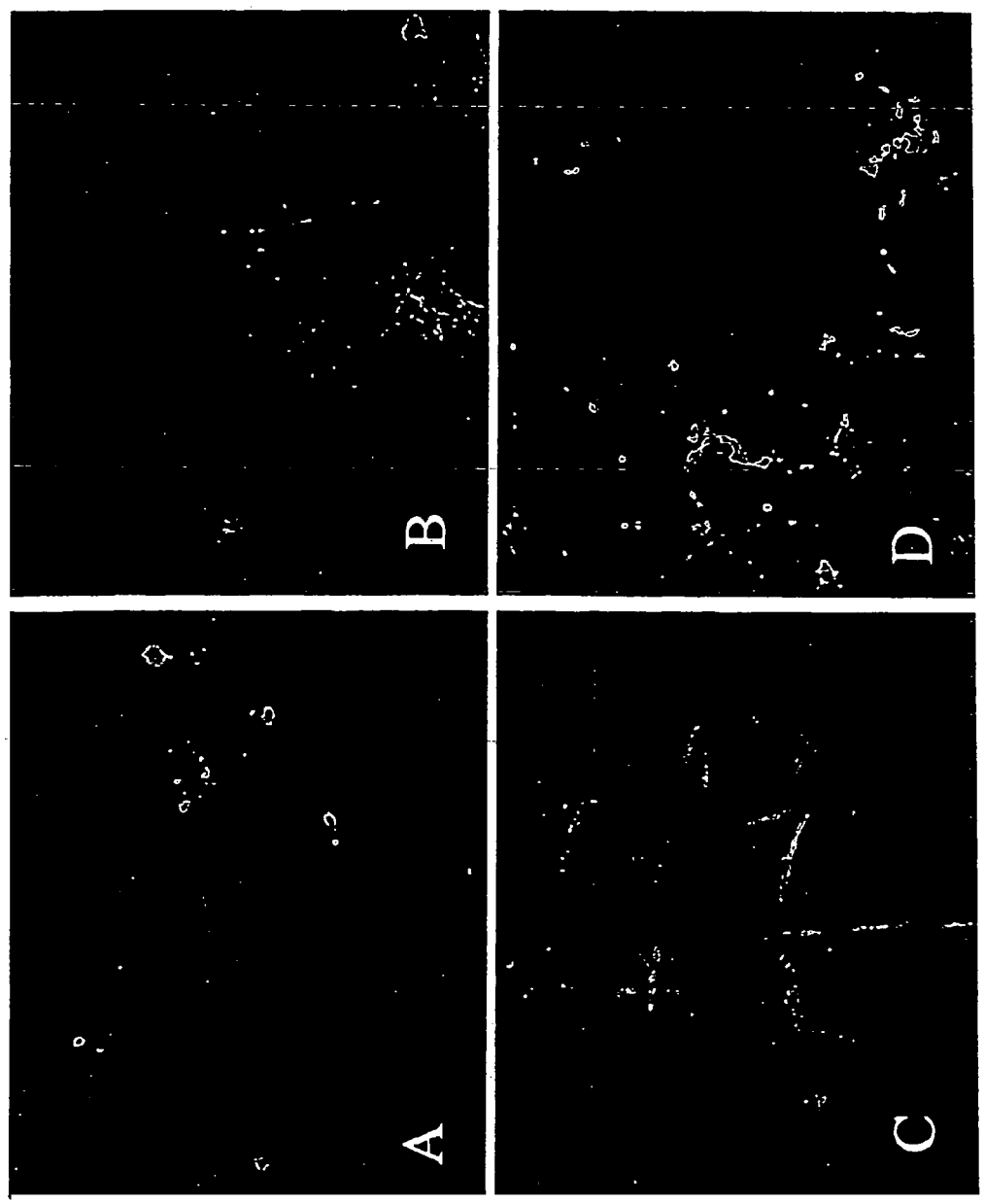
FIGS. 11A–D show the MBP immunohistochemistry in mixed cortical cultures treated with 100 nM of baculovirus expressed recombinant osteopontin.

Effects of Osteopontin on the Expression of Myelination Markers in Mixed Cortical Cultures Mixed cortical cultures, grown on coverslips, were treated with Bac OPN (100 nM) for 12 days from DIV (days in vitro) 5–17. At 17 days in vitro the cultures were fixed and stained with an anti-MBP antibody. The results show that BacOPN coverslips had more highly branched MBP positive oligodendrocytes than controls (FIG. 11). In addition, whereas in control cultures (FIG. 11A) no myelinating oligodendrocytes were seen, OPN treated cultures (FIGS. B, C and D) are rich in oligodendrocytes, which wrap around axons and form myelin segments and internodes. (FIGS. 11B to D). Counting of segment clusters revealed that while no segments could be observed in the control, three different OPN treated samples showed 16, 22, and 18 segment clusters. These results indicate that the treatment of cortical mixed cells with osteopontin leads to a differentiated phenotype of oligodendrocytes, which is characteristic for myelinating oligodendrocytes.

Example 9

Effects of Osteopontin on the Expression of MBP in Mixed Cortical Cultures as Measured by MBP ELISA MBP ELISA Was used in order to monitor MBP protein increase and thus myelination in OPN and LIF treated mixed cortical cultures.

Primary Cultures

The source of the material was embryonic mouse brain tissue from embryos, isolated from pregnant NMR1 female mice at 16 days post-coitum. Embryos were dissected according to the protocol of Lubetzki et al., cortices were dissociated via trypsin digestion and the dissociated cells (including neurons, astrocytes, oligodendrocytes, microglia and neuronal precursors) were seeded at $1*10^5$ cells per well onto poly-L-lysine pre-coated 96-well culture plates (at a 50-µl initial volume) for each well.

Recombinant Protein Treatment

Treatments were performed using recombinant proteins (positive control, recombinant mouse leukemia inhibitory factor (LIF) purchased from AMRAD Laboratories, at concentrations of 1 µg/ml, 100 ng/ml, and 10 ng/ml; mouse baculovirus-produced full-length osteopontin at concentrations of 100 nM, 10 nM, and 10 pM). All proteins were diluted in culture medium to the appropriate concentrations from stock material, prior to addition to cells in vitro. Cultures were allowed to grow for 5 days in vitro and then were treated for 17 days subsequently. Medium was changed every 3 days.

Microwell Plate Protocol for Sample Harvesting

Cells were lysed and samples harvested after 17 days in vitro (DIV17). Cell lysis was performed using triple detergent buffer.

| Triple detergent buffer | Final concentration |
|---|---|
| 50 ml Tris pH 8.01 M | 50 mM |
| 8.77 g NaCl | 150 mM |
| 2 ml NaN$_3$ (10%) | 0.02% |
| 5 ml SDS 20% | 0.1% |
| 10 ml NP40 | 1% |
| 5 g sodium deoxycholate | 0.5% |

A single protease inhibitors tablet (Roche no. 1836170) was added to 10 ml of triple detergent buffer solution prior to use.

Medium was removed from mixed cortical culture samples that had been seeded in 96-well pre-coated plates. Cells were washed gently twice with 50 µl of 1×PBS and then 50 µl of triple detergent buffer was added to each well. All microwell plates containing the lysed samples were then stored at −20° C. prior to analysis.

BCA Protein Assay

The Pierce BCA Protein Assay is a detergent-compatible formulation based on bicinchoninic acid (BCA) for the colorimetric detection and quantification of total protein. This method combines the well-known reduction of $Cu^{+2}$ to $Cu^{+1}$ by protein in an alkaline medium with the highly sensitive and selective colorimetric detection of the cuprous cation ($Cu^{+1}$) using a unique reagent containing bicinchoninic acid.

The purple-colored reaction product of this assay is formed by the chelation of two molecules of BCA with one cuprous ion. This water soluble complex exhibits a strong absorbance at 562 nm that is linear with increasing protein concentrations over a broad working range of 20 µg/ml to 2000 µg/ml. The BCA method is not a true end-point method—the final color continues to develop but, following incubation, the rate of color development is slowed sufficiently to allow large numbers of samples to be done in a single run. The macromolecular structure of protein, the number of peptide bonds and the presence of four amino acids (cysteine, cysteine, tryptophan and tyrosine) are reported to be responsible for color formation with BCA.

Microwell Plate Protocol for Determination of Total Protein Content

25 µl of each standard (BSA concentration: 2000 µg/ml, 1500 µg/ml, 1000 µg/ml, 750 µg/ml, 500 µg/ml, 250 µg/ml, 125 µg/ml, 25 µg/ml) and samples were added into the appropriate microwell plate wells. 25 µl of the diluent (triple detergent buffer) was used for the blank wells (working range 20–2000 µg/ml).

200 µl of working reagent (mixture of 50 parts of BCA Reagent A with 1 part of BCA Reagent B), was added to each well. Plate well was shaken for 30 seconds and incubated at 37° C. for 30 minutes. After incubation the absorbance values were measured at 570 nm.

MBP Sandwich ELISA 96-well flat-bottomed sterile microplates (Costar) were incubated overnight at +4° C. with the anti-MBP antibody (Chemicon, MAB5274) diluted 1:5000 in 1×PBS. 50 µl of the dilute antibody solution was added to each well.

The next day, the antibody solution was removed from all wells in the plates and a blocking step was performed using 50 µl of a 1% BSA solution in 1×PBS for each well. Blocking was performed for 1 hour at ambient temperature. Plates were robotically washed 3 times following the blocking step using PBS/Tween.

Incubation was performed after the addition of serial dilutions of the MBP peptide standard or samples in 1% BSA/PBS to the microwell plates. The MBP peptide 100 ng/ml stock solution was diluted 2 in 2. The dilutions used here were determined after calculation of total protein content using the results of the BCA Protein Assay. They were as follows:

100 µg; 50 µg; 25 µg; 12.5 µg; 6.2 µg; 3.1 µg.

Following incubation with the MBP standard and protein samples, plates were washed 3 times again in 1% BSA/PBS.

A second incubation was performed using a polyclonal anti-MBP antibody (Zymed 10–0038, 1:300) diluted in 1% BA/PBS. Plates were incubated for 2 hours at ambient temperature. Following this incubation, plates were again washed 3 times as above.

Incubation with goat anti-rabbit biotin (Vector BA-1000, 1:10,000), added in 50-µl volumes to all wells after dilution in 1% BSA/PBS, was performed for 1 hour at ambient temperature. Plates were again washed following the incubation as indicated above.

The final incubation was performed with 50 µl of streptavidin-conjugated horse radish peroxidase (strep-HRP) (Amersham RPN 1051, 1:8000) diluted in 1×PBS being added to each well. Plates were incubated for 1 hour at ambient temperature.

Following the washing step, the reaction was revealed using orthophenylenediamine dihydrochloride (OPD) (Sigma, solution prepared by adding 1 tablet to a 20-ml volume of water). This reaction was blocked via addition of 3 M HCl or 30% $H_2SO_4$. The optical density was measured using a multi-scan fluoroplate reader (Labsystems Multiskan EX) at 492 nm.

Results

Figure 12:
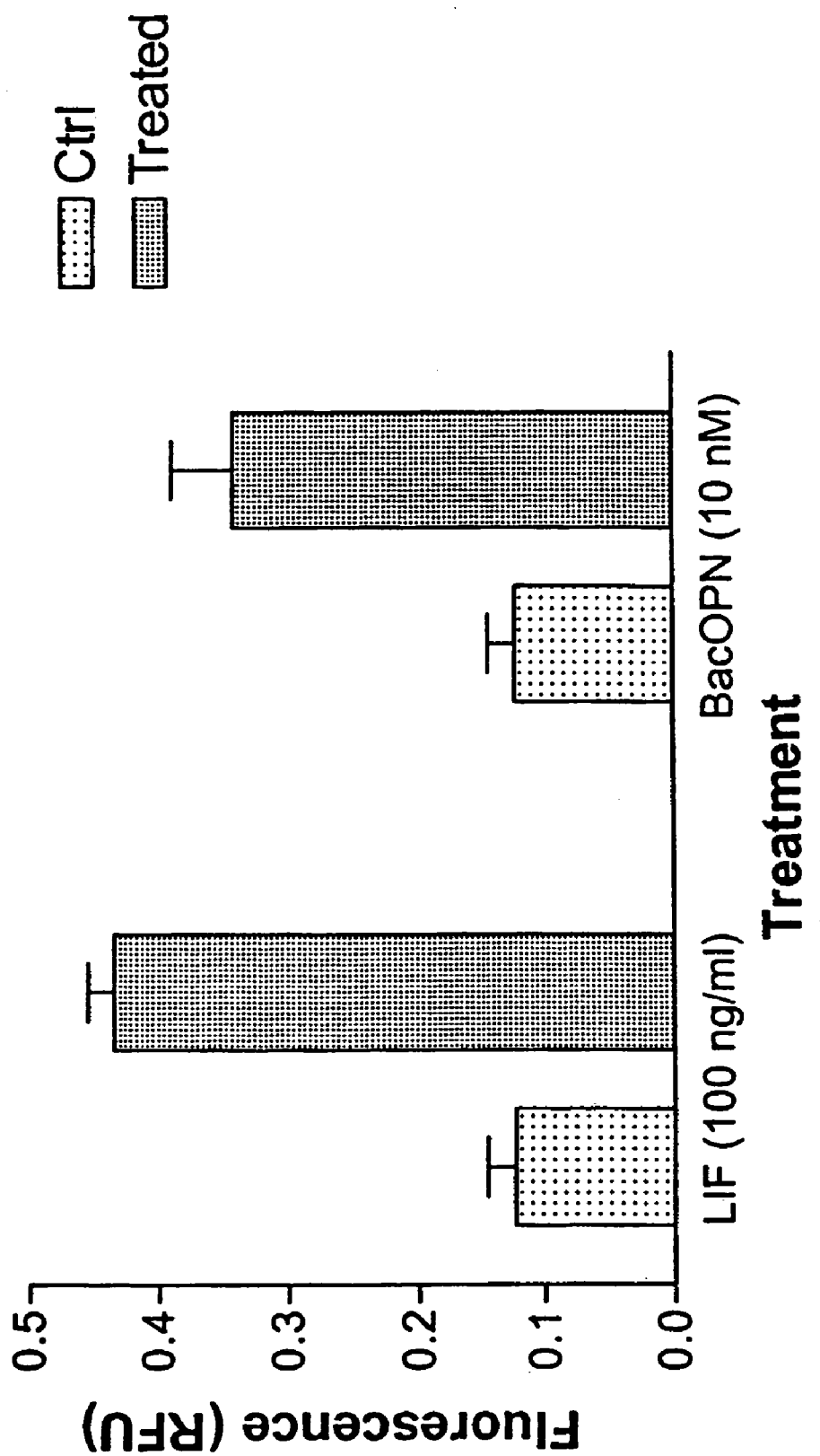
FIG. 12 shows the increase of MBP protein in myelinating, mixed cortical cultures after LIF and baculovirus expressed osteopontin treatment as measured by ELISA.

As shown in FIG. 12, MBP protein levels were increased 3 fold in bacOPN (10 nM) treated cultures at DIV 17 compared to control cultures. This observation supports the previous results showing a positive effect of baculovirus expressed OPN on oligodendrocyte precursor proliferation and myelination.

Example 10

Effect of Osteopontin on CG4 Proliferation

The CG4 cell line is a rat immortalized oligodendrocyte cell line, which was spontaneously obtained from primary A2B5 oligodendrocyte precursors. CG4 cells are a commonly used cell line to study oligodendrocyte differentiation or survival. The CG4 cell line has the following advantages:

High proliferative rate like oligodendrocyte progenitors (O2A-like) (GD3, A2B5-positive cells);

Low cost maintenance in conditioned medium (with effective growth-factor concentrations) obtained from B104 rat neuroblastoma cell line (Louis J. C. et al. 1992) obtained from ATCC.

Defined medium (without FBS) can be used (supplemented with FGF2+PDGF) instead of B104 conditioned medium for proliferation during short periods;

Differentiation into oligodendrocytes (O4,GalC-positive) can be triggered with a defined medium;

Differentiation into astrocytes (GFAP-positive) can be triggered in the presence of FBS.

Passage number 35 of the CG4 cells was used test an effect of two OPN proteins (expressed in *E. coli* or insect cells) on proliferation. R&D System *E. coli* produced osteopontin (Cat.441-OP) was used for this assay, which was then in vitro phosphorylated with protein kinase 2 (GST fused) in a 60 µl volume as follows:

| Kinase buffer 6x: | Sample Buffer 2x pH6 |
|---|---|
| Hepes 50 mM | Tris-Cl 0.125 |
| $MgCl_2$ 10 mM | Glycerol 20% |
| DTT 1 mM | DTT 0.2 M |
| Sodium Vanadate 0.2 mM | Bromophenol Blue 0.02% |
| Beta glycerolphosphate 25 mM | |

ATP Mix (60 µM)
30 µl ATP at 600 µM
5 µl of $^{32}$pATP
265 µl $H_2O_2$

In order to start the reaction ATP mix was added and the incubation was performed at 30° C. for 1 hour. After 90 minutes incubation at 30° C. (with agitation), 100 µl Glutathione Sepharose beads (Pharmacia) were added to the reaction mix that was previously washed in PBS in order to eliminate protein kinase. Then, the mix was incubated for one hour at room temperature with gentle agitation. The suspension was centrifuged at 500 g for 5 minutes to sediment the beads. Then, the supernatant was dialysed overnight supernatant at 4° C. against PBS. The protein was quantified by BCA (Pierce).

Kinase Reaction:
10 µl Casein Kinase at 0.05 µg/µl
10 µl *E. coli* OPN at 0.5 µg/µl
20 µl 50 mM Tris-HCL ph 8
10 µl kinase buffer 6×
10 µl ATP mix Proliferation Assay Bad OPN and in vitro phosphorylated OPN proteins were tested at 10 pM, 10 nM and 100 nM concentrations on proliferation of CG4 cells. As a readout BrdU (Amersham) was used as described in Avellana et al. 1996. The cells were cultured in 70% N1 defined medium (DMEM containing 4.5 g'l glucose, 2 mM glutamine, 100 U/ml penicillin. 100 µg/ml streptomycin and 1 mM sodium pyruvate and supplemented with 5 µg/ml transferrin, 100 mM putrescine, 30 nM sodium selenite and 10 ng/ml biotin) and 30% B104 conditioned medium (N1 without Biotin) (Louis J. C. et al. 1992). The assay was performed in poly-ornithine (100 µg/ml) treated 24 well plates seeded with $3\times10^4$ cell/per well. 10 nM BrdU was added the at the same time and cells were incubated for 18 hours. After fixation, immunocytochemistry was performed with an anti-BrdU antibody to detect cell divisions. Cells were also stained with Hoechst 44432 staining (Sigma) to allow total cell numbers counts. Images were acquired and analyzed using the Leica QWin Image Analysis System.

Results

The results are depicted in FIG. 13.

Baculovirus expressed osteopontin leads to increased proliferation of CG4 cells. The most pronounced effect could be observed at a concentration of 10 nM OPN, although 100 nM of OPN led to proliferation as well. In vitro phosphorylated, E. coli expressed OPN lead to minor proliferation of CG4 cells.

Analysis of the morphology of OPN treated versus non-treated CG4 cells revealed that while in the control, no differentiation could be observed, OPN treated CG4 cells were differentiated in that most of the cells developed processes. While differentiation was more pronounced using baculovirus expressed OPN, E. coli expressed, in vitro phosphorylated OPN lead to CG4 cell differentiation as well (not shown).

Example 11

Effect of Osteopontin on MOG-induced Experimental Autoimmune Encephalomyelitis (EAE) in Mice Purpose of the Study Osteopontin (OPN; AS900011) is a cytokine with pleiotropic functions including those in adhesion, migration, differentiation, survival and cytokine secretion of various cell types. OPN was identified in a differential gene expression (DGE) approach with the aim of detecting genes that could regulate remyelination and oligodendrocyte function (see Example 1). Treatment of oligodendrocyte precursors with recombinant baculovirus expressed OPN (AS900011) increased proliferation in a dose dependent manner ($IC_{50}$: 3.7 pM, see example 7). In addition, AS900011 showed an effect on the differentiation of CG4 cell line and primary neurospheres (see example 8). OPN is expressed in the demyelinated corpus callosum brain region of mice treated with Cuprizone, where expression was strongest in microglial cells (see example 1). In addition, OPN expression was observed in the sub-ventricular zone (SVZ), which has been suggested to generate oligodendrocyte precursors that participate in remyelination (see example 4). It is hypothesized that OPN, a cytokine with various immuno-regulatory properties, may also play a role as a modulator of neuronal and glial function.

The purpose of this study was to test the therapeutic effect of OPN in the model of MOG-induced EAE in mice.

Test Method

The method of induction of EAE used for this study has been adapted from the protocol published by Sahrbacher et al. (1998). Protection of animals used in the experiment is in accordance with Directive 86/609/EEC, enforced by the Italian D.L. No. 116 of Jan. 27, 1992. Physical facilities and equipment for accommodation and care of animals are in accordance with the provisions of EEC Council Directive 86/609. The Institute is fully authorized by Competent Veterinary Health Authorities. All parts of this protocol concerning animal care have been approved by the official Veterinarian. This protocol is authorized by Italian Ministry of Health (Decree No. 51/99-B).

Test System

Species, strain, substrain and sex:

C57 BL/6JICO female mice from the IFFA CREDO (Saint Germain sur l'Arbresle, France) colony was supplied by Charles River Italia (Calco, Lecco, Italy).

Justification for the selection of the test system:

The C57 BL/6JICO mouse was chosen as an experimental model; this selected strain has documented susceptibility to EAE.

Supplier:

Charles River Italia S.p.A.
Via Indipendenza, 11
23885-Calco (Lecco)

Acclimation:

At least 5 days before the study is initiated. In this period the animals will be observed daily to ascertain their fitness for the study.

Age and body weight (at randomization):

About 8 week old; 18–22 g

Housing:

10 animals/cage in air-conditioned rooms.
Temperature: 22° C.±2
Relative humidity: 55%±10
Air changes: about 15–20/hour filtered on HEPA 99.99%.
Light: 12 hour cycle (7 a.m. –7 p.m.)
Cage: Makrolon® cage 42.5×26.6×15 h each fitted with a stainless steel cover-feed rack. A grill is inserted on the cage bottom. The waste that drops through the grill onto the cage bottom will be periodically disposed of.

Animal Identification:

By an ear tag. Cage card will give experiment number, dosage, group and date of compound administration.

Diet:

GLP 4RF25 top certificate pelleted diet produced by Charles River Italia's feed licensee Mucedola S.r.l., Settimo Milanese. To facilitate nourishment of sick animals from day 7 wet pellets are placed every day on the cage bottom. The Producer supplies a certificate of analysis for nutrients and contaminants, the levels of which are within the limits proposed by EPA-TSCA (44FR:44053–44093, Jul. 26, 1979). RBM has the animal food reanalyzed at least twice a year for bacterial contamination. The diet is available "ad libitum" to the animals.

Water:

From the municipal main watering system. Water is filtered and distributed "ad libitum" to the animals by an automatic valve system. Plastic bottles are used in addition to the automatic watering system. Periodically drinking water is analyzed for microbiologic count, heavy metals, other contaminants (e.g. solvents, pesticides) and other chemical and physical characteristics. The acceptance limits of quality of the drinking water are those defined in the EEC Directive 801778.

Contaminants that might interfere with the objectives of the study are not expected to be present in diet or drinking water.

Test Substances:

Murine, 6 his-tagged Osteopontin (AS900011) and mIFNβ

Immunization Procedure:

Mice were immunized (day=0) by injecting s.c. in the left flank 0.2 ml of an emulsion composed of 200 μg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they received an i.p. injection of 500 ng pertussis toxin (List Biological Lab., Campbell, Calif., U.S.A.) dissolved in 400

μl of buffer (0.5 M NaCl, 0.017% Triton X-100, 0.015 M Tris, pH=7.5). On day 2 the animals were given a second i.p. injection of 500 ng pertussis toxin. On day 7, the mice received a second dose of 200 μg of $MOG_{35-55}$ peptide in CFA injected s.c. in the right flank. Starting approximately from day 8–10, this procedure results in a gradually progressing paralysis, arising from the tail and ascending up to the forelimbs.

Study Design:

The study involved 7 groups of 15 animals each. All the groups were immunized with $MOG_{35-55}$ peptide in CFA and pertussis toxin, according to the Immunization protocol and treated as follows:

Group 1: positive control group dosed with OPN vehicle alone (PBS+0.1% BSA) by s.c. route.

Group 2: positive control group dosed with mIFNβ vehicle alone (PBS) by s.c. route.

Group 3: dosed with 1 μg/kg s.c. of Osteopontin (AS900011)

Group 4: dosed with 10 μg/kg s.c of Osteopontin (AS900011)

Group 5: dosed with 100 μg/kg s.c. of Osteopontin (AS900011)

Group 6: dosed with 100 μg/kg s.c. of Osteopontin (AS900011) plus 20,000 U/mouse s.c. of mIFNβ

Group 7: dosed with 20,000 U/mouse s.c. of mIFNβ

The number of animals per group is the minimum number allowing an accurate assessment of observed pharmacological effects.

Vehicle:

PBS plus 0.1% BSA will be used to dilute Osteopontin to the appropriate concentration. PBS will be used to dilute mIFNβ to the appropriate concentration.

Administration Route:

Osteopontin (AS900011) at the dose of 1, 10 and 100 μg/kg was administered s.c. in a volume of 10 ml/kg. mIFNβ at the dose of 20,000 U/mouse will be administered s.c. in a volume of 200 μl/mouse. Group 1 will be dosed s.c. with PBS plus 0.1% BSA in a volume of 10 ml/kg and group 2 will be dosed s.c. with 200 μl/PBS/mouse.

Duration of Treatment:

The treatment of groups of this study was started for each animal at the appearance of a clinical score $\geq 1$ and will then be continued for 35 consecutive days.

Form of Administration:

The compound and mIFNβ were administered as solutions in the appropriate vehicle. Respective formulates will be prepared in accordance with the Sponsor's instructions.

Clinical Observations:

Starting from day 7 post-immunization the animals were individually examined for the presence of paralysis by means of a clinical score as follows:

0=no sign of disease 0.5=partial tail paralysis

1=tail paralysis 1.5=tail paralysis+partial unilateral hindlimb paralysis

2=tail paralysis+hindlimb weakness or partial hindlimb paralysis 2.5=tail paralysis+partial hindlimb paralysis (lowered pelvi)

3=tail paralysis+complete hindlimb paralysis 3.5=tail paralysis+complete hindlimb paralysis+incontinence 4=tail paralysis+hindlimb paralysis+weakness or partial paralysis of forelimbs 5=moribund or dead Observation of the animals took place in a quiet room. Clinical signs were monitored daily in each group of treatment in a blind fashion by a technician who is unaware of treatments.

Body weight of the animals were monitored daily.

Animals considered to be in pain distress or in moribund condition will be examined by the staff veterinarian or authorized personnel and, if necessary, humanely sacrificed to minimize undue pain or suffering.

Blood Sampling:

Twenty four hours after the last treatment, blood samples will be collected (under pentobarbital anaesthesia) from each animal. Serum will be separated by routine procedure and serum samples will be kept stored at −20° C. Frozen sera will be then shipped to SPRI for the relative determinations of compound serum concentration.

Histopathological Examinations:

At the end of treatment, the animals, under pentobarbital anaesthesia, will be perfused-fixed with 4% formaldehyde via the left ventricle. Then, their spinal cords will carefully be dissected out and fixed in formalin. Spinal cord slices will be embedded in paraffin blocks. Sectioning and staining with hematoxylin and eosin for inflammation, and with Kluver-PAS (Luxol fast blue plus Periodic Acid Schiff staining) for the detection of demyelination, will be performed.

Data Evaluation:

Results of clinical examinations are expressed as the mean (±SEM) score within each group. The effects of the test substances will be compared with that of the vehicle-treated positive control group. Differences of clinical score values among groups will be analysed by Kruskal-Wallis test followed, in case of significance, by the pairwise Wilcoxon test, at each measurement time. Body weight data will be evaluated by one-way ANOVA followed, in case of significance, by Tukey test. The S- Plus® software will be used.

Figure 14:
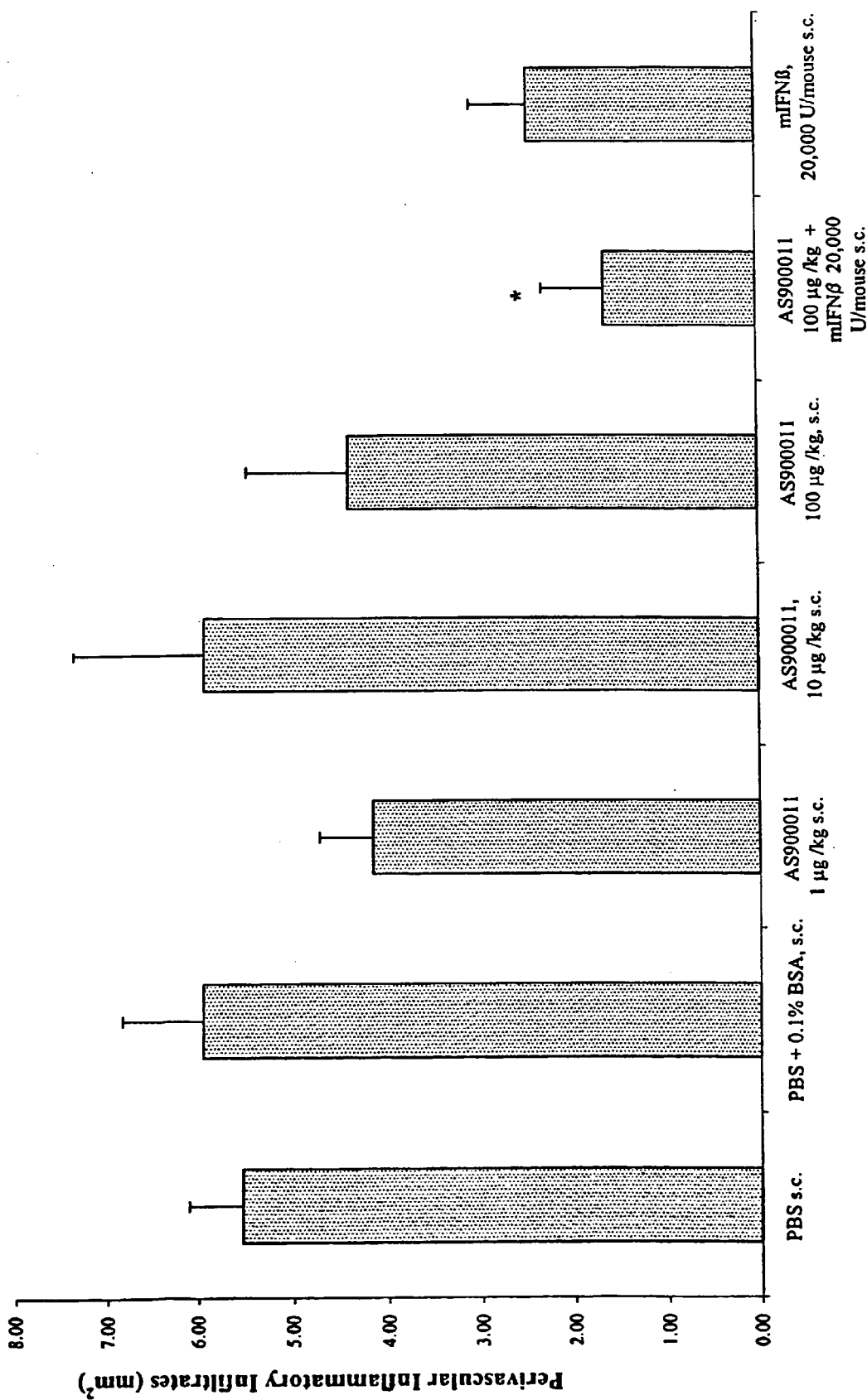
FIG. 14 shows the perivascular inflammatory infiltrates present in spinal cords of EAE mice treated subcutaneously with vehicle (PBS), vehicle plus 0.1% BSA, 1, 10 or 100 µg/kg of AS900011 (osteopontin) or with a combination of 100 µg/kg AS900011 and 20000 U/mouse murine interferon beta (mIFNβ), or 20000 U/mouse mIFNβ alone.
Figure 15:
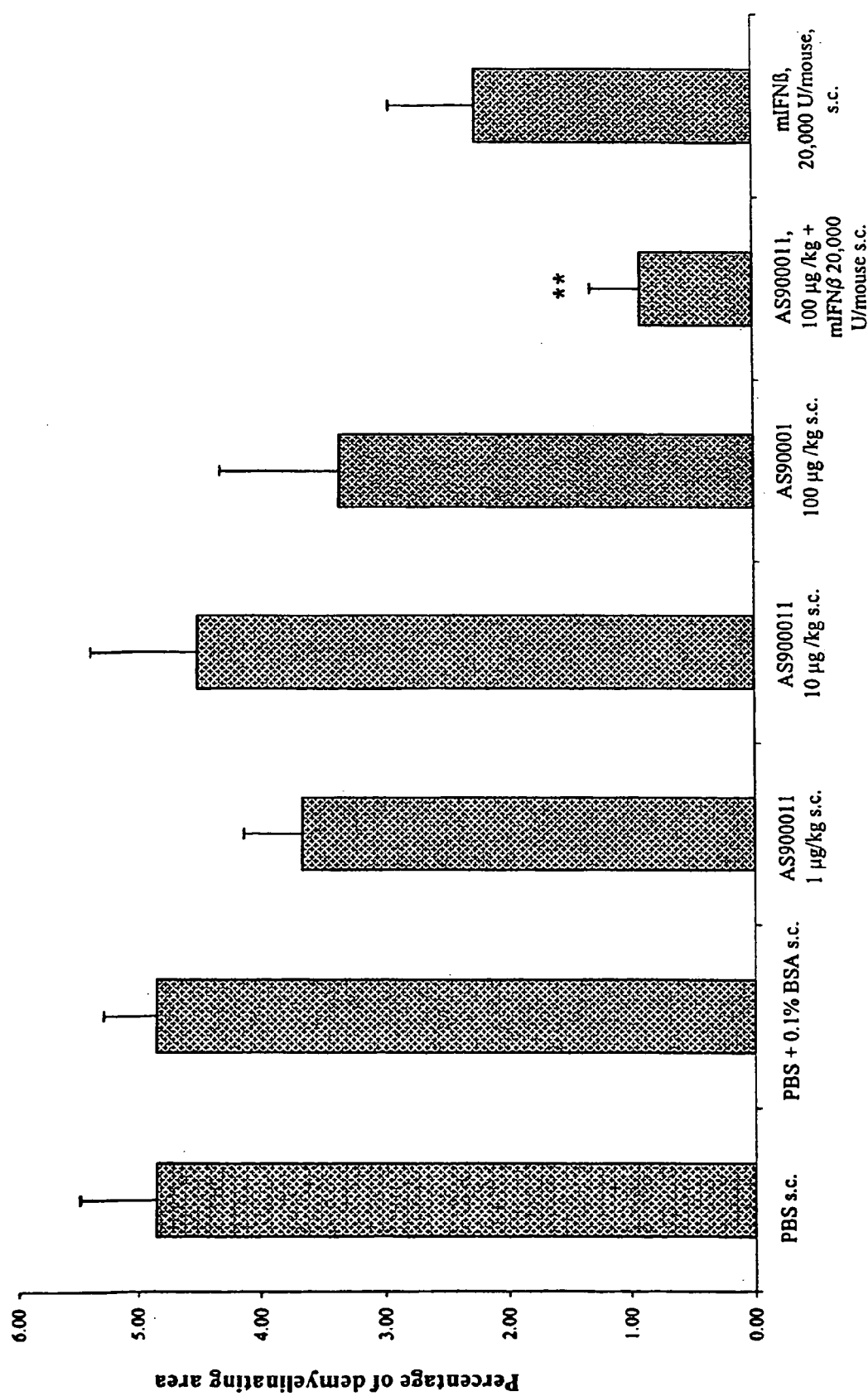
FIG. 15 shows the percentage of demyelinating area present in spinal cords of EAE mice treated subcutaneously with vehicle (PBS), vehicle plus 0.1% BSA, 1, 10 or 100 µg/kg of AS900011 (osteopontin) or with a combination of 100 µg/kg AS900011 and 20000 U/mouse murine interferon beta (mIFNβ) or 20000 U/mouse mIFNβ alone.
Figure 16:
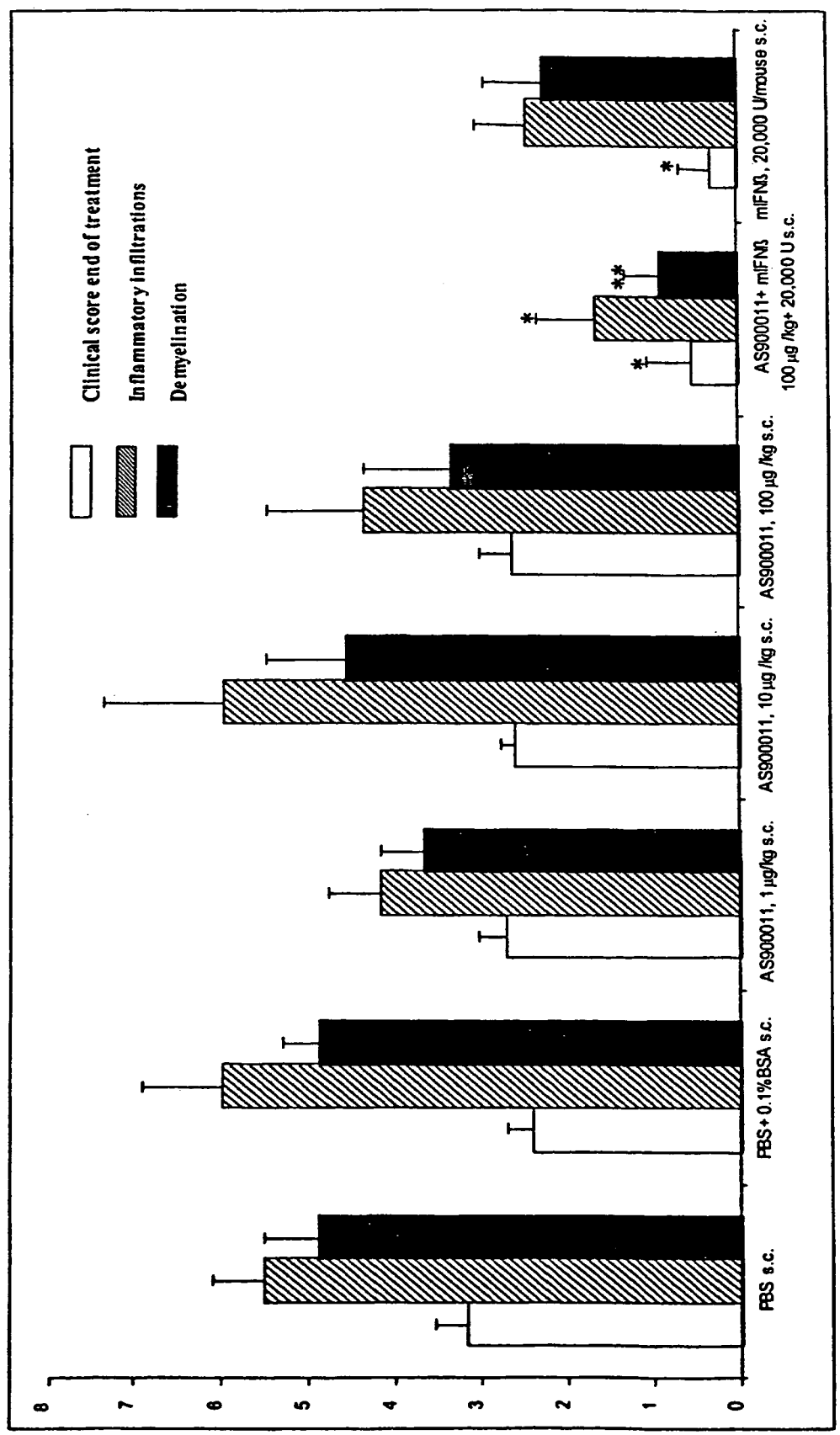
FIG. 16 shows clinical scores at the end of treatment, the inflammatory infiltrations and the demyelination in EAE mice treated subcutaneously with vehicle (PBS), vehicle plus 0.1% BSA, 1, 10 or 100 µg/kg of AS900011 (osteopontin) or with a combination of 100 µg/kg AS900011 and 20000 U/mouse murine interferon beta (mIFNβ) or 20000 U/mouse mIFNβ alone.

Results:

The results of this study are shown in FIGS. 14 to 16.

Histological analysis of the perivascular inflammatory infiltrated revealed that there was a trend towards a lower amount of perivascular infiltrates in OPN treated animals, especially at the lowest administered amount of 1 μg/kg. The combination of OPN and IFNβ, which is a compound known to be active in treatment of multiple sclerosis, was more efficacious than administration of OPN or IFN alone, respectively (FIG. 14).

Next, the percentage of demyelinated areas was measured (FIG. 15). Again, in animals treated with OPN, a trend towards less demyelinated areas could be observed. The combination of IFN and OPN lead to a highly significant reduction of demyelination, which was even much lower than the extent of demyelination that was observed with IFN alone (FIG. 15).

FIG. 16 summarizes the clinical scores observed at the end of the treatment, the inflammatory infiltrations and the demyelination measured in this study. Although the clinical scores observed in OPN treated mice were not significantly lower than the control, the combination of OPN and IFN led to a pronounced effect on the clinical scores, which was as low as with the positive control, interferon-beta. This observation is in agreement with the measurement of the inflammatory infiltrates and the extent of demyelination. Both parameters were significantly reduced after administration of OPN and IFNβ (FIG. 16).

In summary, the following results were obtained in this study:

Osteopontin (AS900011) tested alone at the doses of 1, 10 and 100 mg/kg s.c. did not reduce perivascular infiltrations and demyelination with statistical significance. The treatment with mIFNbeta (20,000 U/mouse s.c.) induced a reduction in perivascular infiltrations (55%) and demyelination (53%). When mIFNbeta at the same dose was combined with AS900011 at the dose of 100 mg/kg s.c., a significant and marked reduction in inflammatory infiltrations (71%) and demyelination (81%) was observed.

Histological data correlated with clinical scores observed at day 35 (end of treatment), when animals were sacrificed and spinal cord collected for histological analysis. Osteopontin (AS900011) tested alone at the doses of 1, 10 and 100 mg/kg s.c. did not significantly reduce disease severity. The treatment with mIFNbeta (20,000 U/mouse s.c.) significantly reduced disease severity. When mIFNbeta at the same dose was combined with AS900011 at the dose of 100 mg/kg s.c, a statistically significant decrease of clinical signs was observed.

These data suggest that the combined osteopontin and mIFNbeta treatment is effective in reducing both clinical and pathological effects in the mouse EAE model, and may therefore be an efficient treatment of multiple sclerosis.

Example 12

Protective Effect of Osteopontin on Neuropathy Induced by Sciatic Nerve Crush in Mice Abbreviations
CMAP: compound muscle action potential
EMG: electromyography
IGF-1: insulin-like growth factor
SC: subcutaneous
s.e.m.: standard error of the mean
vs: versus Introduction Neuropathies are usually selective as to the type of PNS neurone affected (e.g. sensory versus autonomic) and indeed also to the subtype of neurons (small versus large). Axotomy of peripheral nerves is the most commonly used animal model for appraising the neuroprotective effects of neurotrophic factors. Traumatic nerve injury, plexus lesions and root lesions are a serious complication of accidents. In addition, pressure on peripheral nerve that can cause myelin damage frequently seen in disorders such as carpal tunnel syndrome or is associated with spinal column orthopedic complications. Axotomy produces phenomena, like cell death, reduced axonal conduction velocity, and altered neurotransmitter levels in damaged neurons. Crush lesions allow for regeneration, an additional process of interest in relation to neuropathic states (McMahon S. and Priestley J. V. 1995).

A fundamental question in cellular neurobiology is the regulation of nerve regeneration after injury or disease. Functional nerve regeneration requires not only axonal sprouting and elongation, but also new myelin synthesis. Remyelination is necessary for the restoration of normal nerve conduction and for protection of axons from new neurodegenerative immunologic attacks. The primary goal of research in neurodegenerative disorders is ultimately to develop interventions which prevent neuronal death, maintain neuronal phenotype and repair neuronal and myelin damage. Many studies have been devoted to the unraveling of molecular and cellular mechanisms responsible for the complete regeneration of axotomized spinal motor neurons (Fawcett et al., 1990; Funakoshi et al., 1993). Injury-induced expression of neurotrophic factors and corresponding receptors may play an important role in the ability of nerve regeneration. Previous studies have shown a significant improvement of nerve regeneration with various peptides and nonpeptides compounds like insulin-like growth factor (IGF-1), ACTH (Lewis et al., 1993; Strand et al., 1980), testosterone (Jones, 1993), SR57746A (Fournier et al., 1993) and 4-Methylcatechol (Kaechi K et al. 1993, 1995; Hanaoka Y et al. 1992).

The present study was carried out to evaluate nerve regeneration in mice treated with osteopontin at different doses. In this model a positive effect of OPN on neuronal and axonal (sensory and motor neurons) survival and regeneration, on myelination or macrophage inflammation could lead to a restoration of motor function. The regeneration may be measured according to the restoration of sensorimotor functions and morphological studies. Therefore in the present work electrophysiological recordings and histomorphometric analysis were performed in parallel.

Materials and Methods

Animals

Eightyfour 8 weeks-old females C57bI/6 RJ mice (Elevage Janvier, Le Genest-St-Isle, France) were used. They were divided into 7 groups (n=12): (a) vehicle sham operated group; (b) vehicle nerve crush operated group; (c) nerve crush/osteopontine (1 μg/kg); (d) nerve crush/osteopontin (10 μg/kg); (e) nerve crush/osteopontin (100 μg/kg); (f) nerve crush/4-methylcatechol (10 μg/kg); (g) nerve crush/denaturated osteopontin (100 μg/kg).

They were group-housed (5 animals per cage) and maintained in an incubator with controlled temperature (21–22° C.) and a reversed light-dark cycle (12 h/12 h) with food and water available ad libitum. All experiments were carried out in accordance with institutional guidelines.

Lesion of the Sciatic Nerve

The animals were anaesthetized with IP injection of 60 mg/kg ketamine chlorhydrate (Imalgene 500®, Rhône Mérieux, Lyon, France). The right sciatic nerve was surgically exposed at mid thigh level and crushed at 5 mm proximal to the trifurcation of the sciatic nerve. The nerve was crushed twice for 30 s with a haemostatic forceps (width 1.5 mm; Koenig; Strasbourg; France) with a 90 degree rotation between each crush.

Planning of Experiments and Pharmacological Treatment

Electromyographical (EMG) testings were performed once before the surgery day (baseline) and each week during 3 weeks following the operation.

The day of nerve crush surgery was considered as day (D) 0. No test was performed during the 4 days following the crush.

Body weight and survival rate were recorded every day.

From the day of nerve injury to the end of the study, osteopontin and denaturated osteopontin were administered daily by SC route whereas daily injection of 4-methylcatechol was perform in IP.

At the 4$^{th}$ week, 4 animals per group were sacrificed and sciatic nerve was dissected to perform morphological analysis.

Electrophysiological Recording

Electrophysiological recordings were performed using a Neuromatic 2000M electromyograph (EMG) (Dantec, Les Ulis, France). Mice were anaesthetized by intraperitoneal injection of 100 mg/kg ketamine chlorhydrate (Imalgene 500®, Rhône Mérieux, Lyon, France). The normal body temperature was maintained at 30° C. with a heating lamp and controlled by a contact thermometer (Quick, Bioblock Scientific, Illkirch, France) placed on the tail.

Compound muscle action potential (CMAP) was measured in the *gastrocnemius* muscle after single 0.2 stimulation of the sciatic nerve at a supramaximal intensity (12.8 mA). The amplitude (mV), the latency (ms) and the duration (time needed for a depolarization and a repolarization session) of the action potential were measured. The amplitude is indicative of the number of active motor units, while the distal latency indirectly reflects motor nerve conduction and neuromuscular transmission velocities.

Morphometric Analysis

Morphometric analysis was performed 3 weeks after the nerve crush. Four randomly selected animals per groups were used for this analysis. They were anesthetized with IP injection of 100 mg/kg Imalgene 500®. A 5 mm segment of sciatic nerve was excised for histology. The tissue was fixed overnight with a 4% aqueous solution glutaraldehyde (Sigma, L'Isle d'Abeau-Chesnes, France) in phosphate buffer solution (pH=7.4) and maintained in 30% sucrose at +4° C. until use. The nerve was fixed in 2% osmium tetroxide (Sigma, L'Isle d'Abeau-Chesnes, France) in phosphate buffer for 2 h and dehydrated in serial alcohol solutions and embedded in Epon. Embedded tissues were then placed at +70° C. during 3 days for polymerisation. Transverse sections of 1.5 µm were made with a microtome and stained of 1% of toluidine blue (Sigma, L'Isle d'Abeau-Chesnes, France) for 2 min and dehydrated and mounted in Eukitt. Twenty sections per sample were observed using an optical microscope (Nikon, Tokyo, Japan) and morphometric analysis was performed on 6 randomized slices per nerve sample, with a semi-automated digital image analysis software (Biocom, France). Two fields per slice were studied. The following parameters were calculated: the percentage of degenerate fibers (per field) and total number of fibers.

Data Analysis

Global analysis of the data was performed using one factor or repeated measure analysis of variance (anova) and one way anova, and non-parametric tests (mann whitney test). dunnett's test was used further when appropriate. The level of significance was set at $p<0.05$. The results were expressed as mean±standard error of the mean (s.e.m.).

Results

All the animals survived after the nerve crush procedures. A mice (nerve crush/vehicle n°2) died on day 7 and 2 (vehicle sham operated n°3 and N°6) on day 14, as a consequence of anesthesia during the EMG evaluation.

Animal Weight

Figure 17:
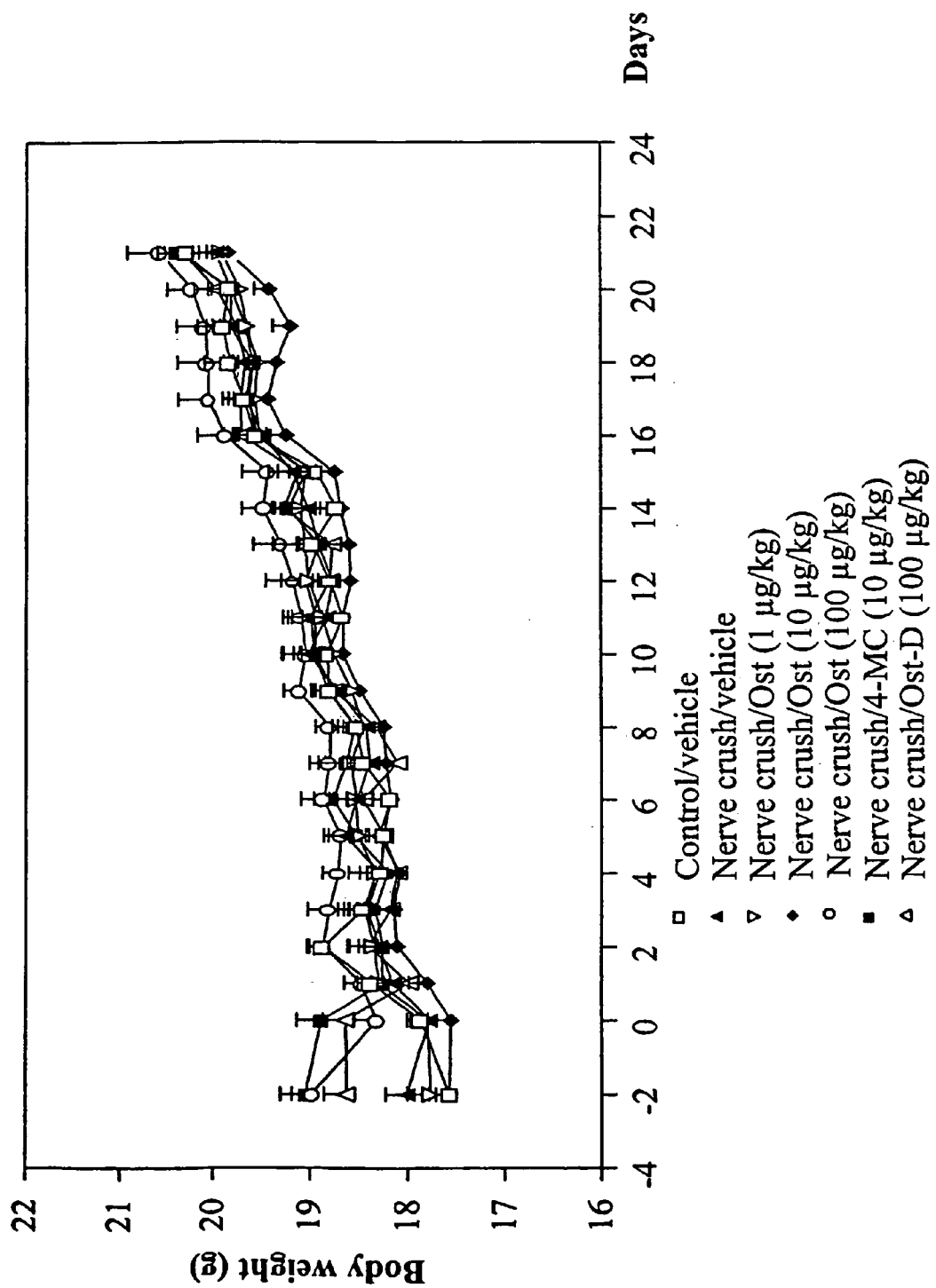
FIG. 17 shows the body weight of neuropathic mice induced by static nerve crush treated with vehicle, 1, 10 or 100 µg/kg of osteopontin (Ost), 10 µg/kg of a positive control compound (4-MC) or 100 µg/kg of denatured osteopontin (Ost-D).

As illustrated in FIG. 17, a significant intergroup was noted in the body weight evolution throughout the study [F (6, 132)=1.93 and $p<0.001$; repeated measures ANOVA].

All different groups displayed an increase of body weight throughout the study.

Electrophysiological Measurements

Figure 18:
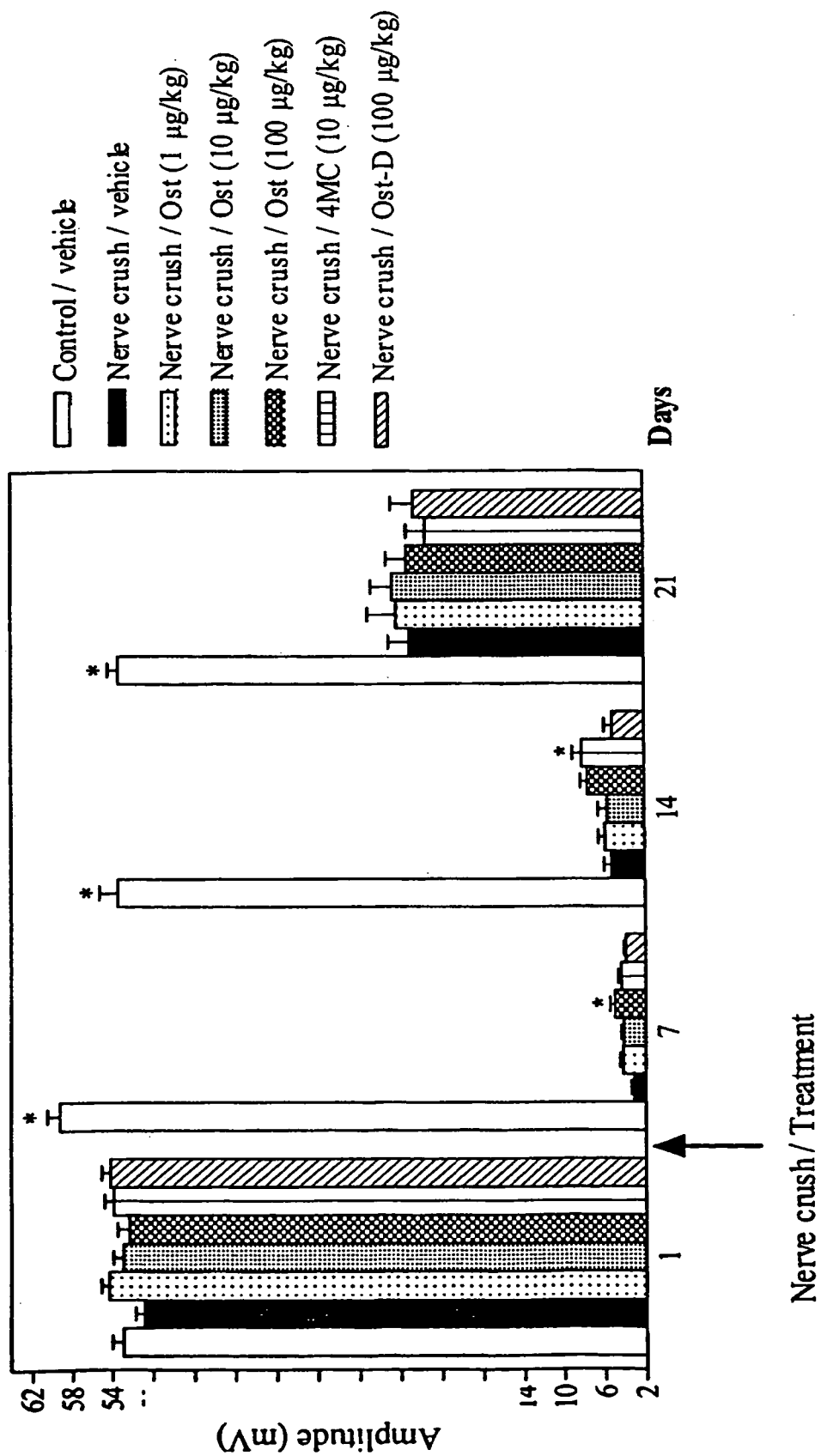
FIG. 18 shows the amplitude of the compound muscle action potential in the neuropathic mice treated with vehicle, 1, 10 or 100 µg/kg of osteopontin (Ost). 10 µg/kg of a positive control compound (4-MC) or 100 µg/kg of denatured osteopontin (Ost-D).
Figure 19:
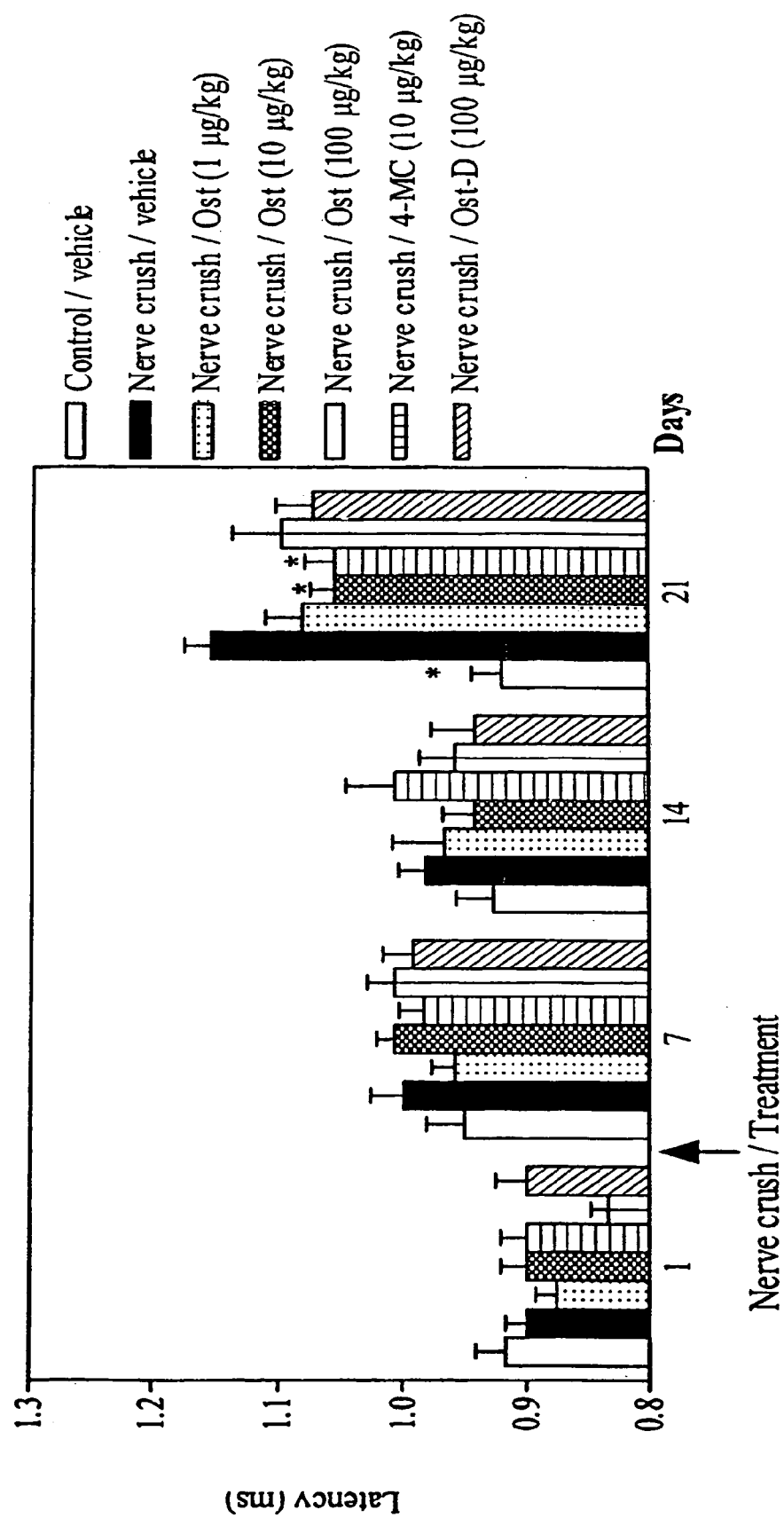
FIG. 19 shows the latency of the compound muscle action potential in the neuropathic mice treated with vehicle, 1, 10 or 100 µg/kg of osteopontin (Ost), 10 µg/kg of a positive control compound (4-MC) or 100 µg/kg of denatured osteopontin (Ost-D).

Amplitude of the Compound Muscular Action Potential (FIG. 18):

There was a significant intergroup difference in amplitude of the CMAP throughout the study [F (6, 18)=49.185 and $p<0.001$; repeated measure ANOVA] (FIG. 19).

After the nerve injury, all animals submitted to nerve crush displayed a significant decrease of CMAP amplitude in comparison with sham operated group ($p<0.001$; Dunnett's test).

Moreover, on D 7 and D 14, CMAP amplitude of mice treated with osteopontin at 100 µg/kg or 4-methylcatechol at 10 µg/kg, were significantly higher than the nerve crush/vehicle one ($p<0.05$; Dunnett's test).

No significant difference was noted between nerve crush/vehicle group and nerve crush/D-osteopontin 100 µg/kg.

Figure 20:
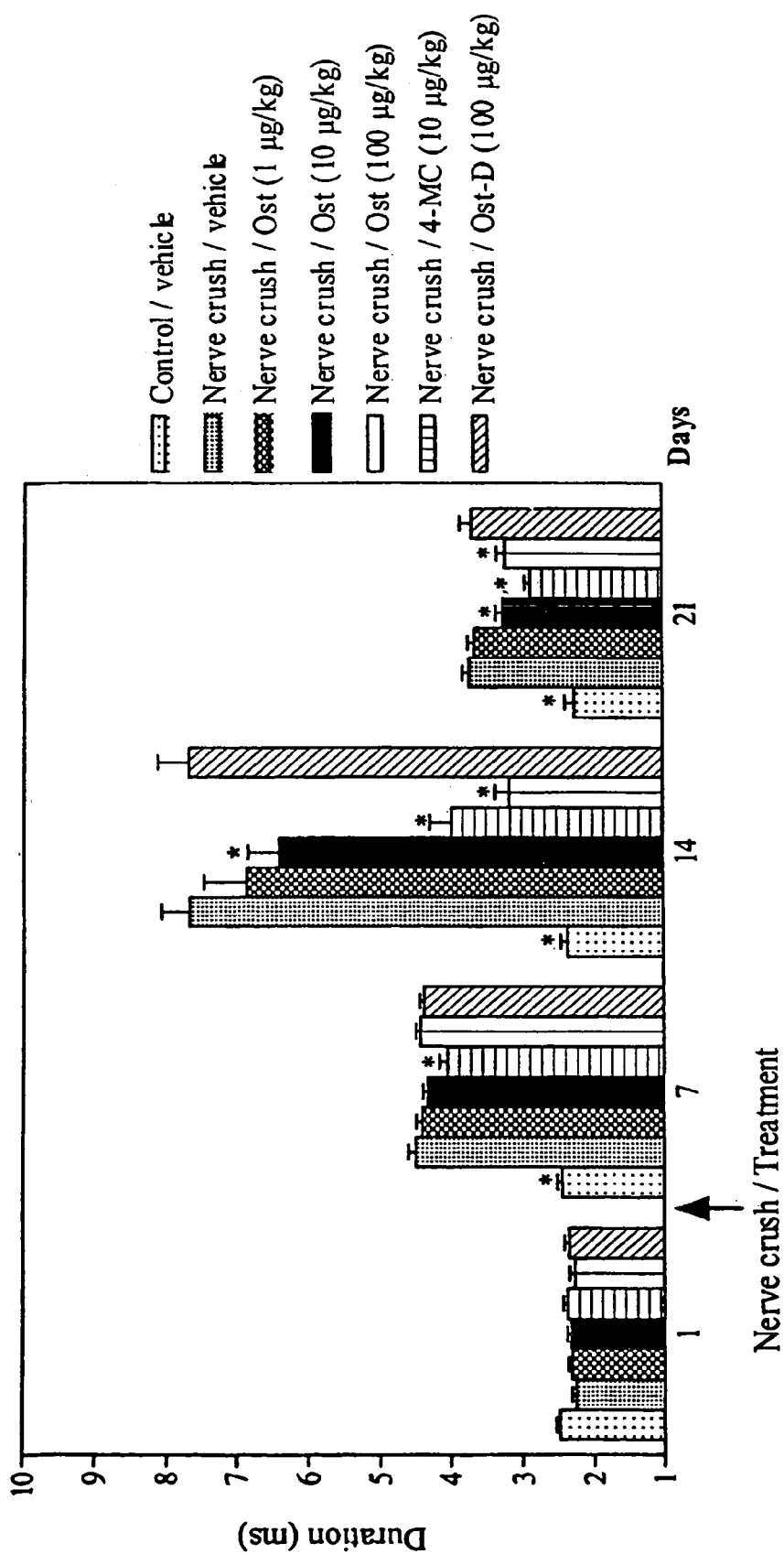
FIG. 20 shows the duration of the compound muscle action potential in the neuropathic mice treated with vehicle, 1, 10 or 100 µg/kg of osteopontin (Ost), 10 µg/kg of a positive control compound (4-MC) or 100 µg/kg of denatured osteopontin (Ost-D).

Latency of the Compound Muscular Action Potential (FIG. 19):

As illustrated in FIG. 20, a significant intergroup difference was found in the CMAP latency [F (6, 18)=2.521 and $p<0.001$; repeated measures ANOVA]. On D 21, nerve crush groups presented an increased CMAP latency in comparison with sham operated group ($p<0.001$; Dunnett's test). Moreover, osteopontin treatment at 10 and 100 µg/kg showed a significant effect, indeed latency of these groups was significantly smaller than that of nerve crush/vehicle one ($p=0.017$; Dunnett's test).

There was no significant difference between the nerve crush/vehicle and nerve crush/D-osteopontin 100 µg/kg groups.

Duration of the Compound Muscular Action Potential (FIG. 20):

There was a significant intergroup difference in the CMAP duration throughout the study [F (6, 18)=25.15 and $p<0.001$; repeated measures ANOVA] (FIG. 20).

Since D 7, a significant increase of CMAP duration was observed in nerve crush groups (sham operated group vs nerve crush groups: $p<0.001$; Dunnett's test). Moreover, at D 7 nerve crush/osteopontin 100 µg/kg displayed a duration significantly shorter than that of nerve crush/vehicle group ($p<0.001$; Dunnett's test).

On D 14 and D 21, three groups presented a significant decreased duration in comparison with the nerve crush/vehicle group: (a) nerve crush/osteopontin 10 µg/kg; (b) nerve crush/osteopontin 100 µg/kg; (c) nerve crush/4-methylcatechol 10 µg/kg.

Furthermore, no significant difference was observed between the nerve crush/vehicle and nerve crush/D-osteopontin 100 µg/kg groups.

Morphometric Analysis

Figure 21:
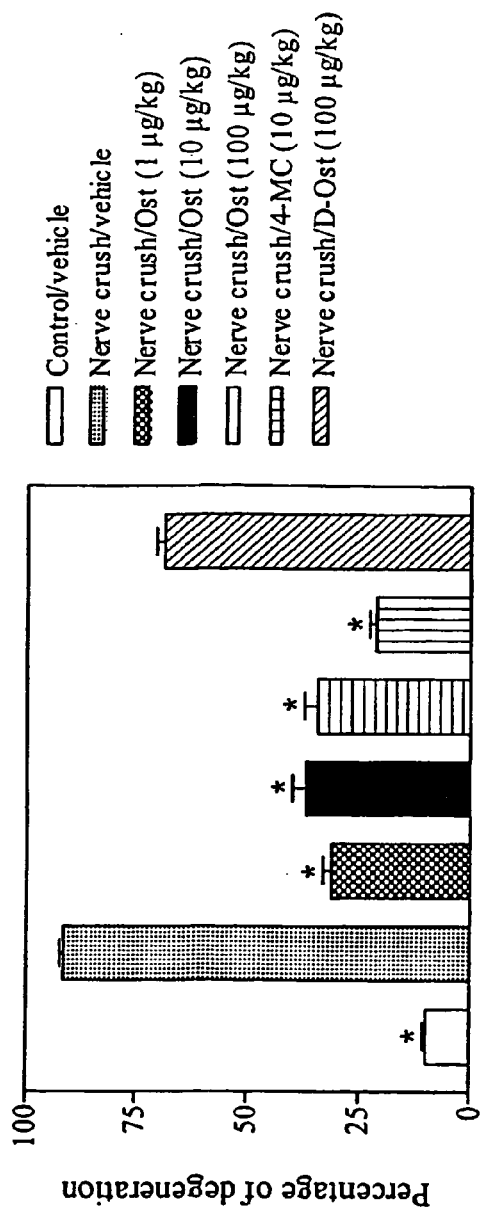
FIG. 21 shows the percentage of degenerated fibers in the neuropathic mice treated with vehicle, 1, 10 or 100 µg/kg of osteopontin (Ost), 10 µg/kg of a positive control compound (4-MC) or 100 µg/kg of denatured osteopontin (Ost-D).
Figure 22:
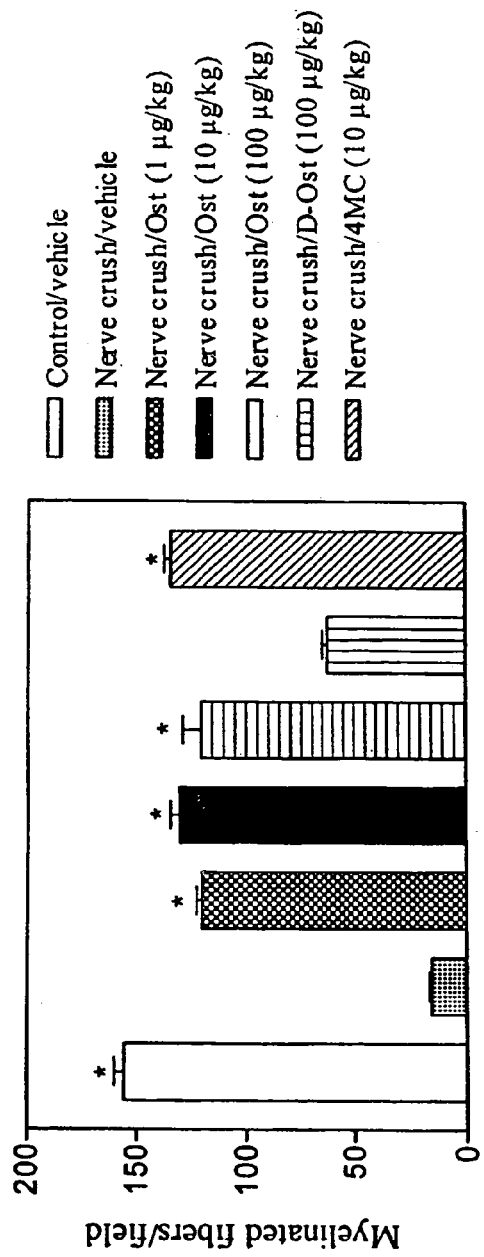
FIG. 22 shows total number of fibers per field in the neuropathic mice treated with vehicle, 1, 10 or 100 µg/kg of osteopontin (Ost), 10 µg/kg of a positive control compound (4-MC) or 100 µg/kg of denatured osteopontin (Ost-D).

Percentage of Degenerate Fibers (FIG. 21):

Statistical analysis revealed a significant intergroup difference in percentage of degenerate fibers per field ($p<0.001$; one way ANOVA) (FIG. 22). All nerve crush groups displayed a significant increased percentage of degenerate fibers ($p<0.001$, Dunnett's test). Moreover, nerve crush/treated mice presented a percentage significantly lower than that of nerve crush/vehicle group ($p<0.001$; Dunnett's test). Moreover, the D-osteopontin (100 µg/kg) treated group displayed an higher percentage of degenerated fibers than the osteopontin-treated groups ($p<0.001$; Dunnett's test).

Total Number of Fibers (FIG. 22):

Sections were observed using an optical microscope and morphometric analysis was performed with the aid of the Visiolab 2000 software (Biocom, Paris, France). Five sections per animal, 2 fields per section were analyzed. Only the functional myelinated fibers were recorded by the computer (all the degenerated fibers meaning with a degeneration the myelin sheath are not recorded).

CONCLUSIONS

The nerve crush model a very dramatic model of peripheral neuropathy. Immediately after the nerve crush most of the big diameter fibers are lost, due to the mechanical injury, leading to the strong decrease in the CMAP amplitude. The CMAP latency is not immediately affected but shows an increase at 21 days due to additional degeneration of small diameter fibers by secondary, immune mediated degeneration (macrophages, granulocytes). The CMAP duration is increased at day 7, peaks at day 14 and returns to levels at day 21 which are comparable to the 7 days timepoint. This is due to the fact that at 21 days, crush lesions allow for regeneration, an additional process of interest in relation to neuropathic states. This axonal sprouting/regeneration was also evident in control groups at the three weeks timepoint.

Osteopontin showed a protective effect in the nerve crush model in mice. Sensorimotor functions were significantly restored at 7, 14 and 21 days post injury in a dose dependent manner and morphological studies performed at 21 days post crush show a significant decrease in the percentage of degenerating fibers and a increase in total fiber number. OPN is as effective as the control molecule used in this study, 4-methylcatechol and heat inactivated, degenerated OPN protein does not show any significant effect on functional or histological parameters. This positive effect on functional and histological recovery may be due to OPN effects on:

direct protection of fibers from secondary immune mediated degeneration;
accelerated remyelination and protection of axons;
accelerated regeneration/sprouting of damaged axons;
increased myelin debris clean up by macrophages.

1. REFERENCES

2. Abramsky, O. and Ovadia, H. (1997) Frontiers in Multiple Sclerosis, clinical research and therapy. Martin Dunitz publisher, London.
3. Altschul S F et al, J Mol Biol, 215, 403–410, 1990, Altschul S F et al, Nucleic Acids Res., 25:389–3402, 1997
4. Barres, B. A., and Raff, M. C. Axonal control of oligodendrocyte development. Journal of Cell Biology 147(6): 1123–8, 1999.
5. Barres, B. A., Schmid, R., Sendtner, M., and Raff, M. C. Multiple extracellular signals are required for long-term oligodendrocyte survival. Development 118(1): 283–95, 1993.
6. Bjartmar, C., Yin, X., and Trapp, B. D. Axonal pathology in myelin disorders. Journal of Neurocytology 28: 383–395, 1999.
7. Breighton, B and Hayden, M R: S Afr Med J. Feb. 21, 1981; 59(8): 250.
8. Dal Canto, M. C., Melvold, R. W., Kim, B. S., and Miller, S. D. Two models of multiple sclerosis: experimental allergic encephalomyelitis (EAE) and Theiler's murine encephalomyelitis virus (TMEV) infection. A pathological and immunological comparison. Microsc. Res. Tech. 32(3): 215–29, 1995.
9. Derynk R. et al., Nature 285, 542–547, 1980
10. Devereux J et al, Nucleic Acids Res, 12, 387–395, 1984.
11. Dubois-Dalcq, M., Feigenbaum, V., and Aubourg, P. The neurobiology of X-linked adrenoleukodystrophy, a demyelinating peroxisomal disorder. Trends in Neurosciences 22(1): 4–12, 1999.
12. Dubois-Dalcq, M., and Murray, K. Why are growth factors important in oligodendrocyte physiology? Pathol Biol (Paris) 48(1): 80–6, 2000.
13. Fernández, P. A., Tang, D. G., Cheng, L., Prochiantz, A., Mudge, A. W., and Raff, M. C. Evidence that axon-derived neuregulin promotes oligodendrocyte survival in the developing rat optic nerve. Neuron 28(1): 81–90, 2000.
14. Franklin, R. J., and Hinks, G. L. Understanding CNS remyelination: clues from developmental and regeneration biology. Journal of Neuroscience Research 58(2): 207–13, 1999.
15. Grantham, Science, Vol. 185, pp. 862–864 (1974).
16. Grinspan, J. B., Reeves, M. F., Coulaloglou, M. J., Nathanson, D., and Pleasure, D. Re-entry into the cell cycle is required for bFGF-induced oligodendroglial dedifferentiation and survival. Journal of Neuroscience Research 46(4): 456–64, 1996.
17. Grinspan, J. B., Stern, J. L., Franceschini, B., and Pleasure, D. Trophic effects of basic fibroblast growth factor (bFGF) on differentiated oligodendroglia: a mechanism for regeneration of the oligodendroglial lineage. Journal of Neuroscience Research 36(6): 672–80, 1993.
18. Hajihosseini, M., Tham, T. N., and Dubois-Dalcq, M. Origin of oligodendrocytes within the human spinal cord. Journal of Neuroscience 16(24): 7981–94, 1996.
19. Hartung, H. P., van der Meche, F. G/, Pollard, J. D. (1998) Guillain-Barre syndrome, CIDP and other chronic immune-mediated neuropathies. Curr. Opin. Neurol., 11, 497–513
20. Hiremath, M. M., Saito, Y., Knapp, G. W., Ting, J. P., Suzuki, K., and Matsushima, G. K. Microglial/macrophage accumulation during Cuprizone-induced demyelination in C57BU/6 mice. Journal of Neuroimmunology 92(1–2): 38–49, 1998.
21. Ichikawa H, Itota T, Nishitani Y, Torii Y, Inoue K, Sugimoto T. Brain Res Apr. 28, 2000; 863(1–2):276–81
22. Jung, M., Krämer, E., Grzenkowski, M., Tang, K., Blakemore, W. F., Aguzzi, A., Khazaie, K., Chlichlia, K., von Blankenfeld, G., Kettenmann, H., and Trotter, J. Lines of murine oligodendroglial precursor cells immortalized by an activated neu tyrosine kinase show distinct degrees of interaction with axons in vitro and in vivo. European Journal of Neuroscience 7(6) 1245–65, 1995.
23. Kiefer et al. The cDNA and derived amino acid sequence for human osteopontin. Nucleic Acids Res. Apr. 25, 1989; 17(8):3306.
24. Kon S, Maeda M, Segawa T. Hagiwara Y. Horikoshi Y. Chikuma S, Tanaka K, Rashid M M, Inobe M, Chambers A F, Uede T. (2000) Antibodies to different peptides in osteopontin reveal complexities in the various secreted forms. Journal of Cellular Biochemistry 77(3): 487–98.
25. Kon S, Yokosaki Y. Maeda M, Segawa T. Horikoshi Y. Tsukagoshi H. Rashid M M, Morimoto J. Inobe M, Shijubo N. Chambers A F, Uede T. (2002) Mapping of functional epitopes of osteopontin by monoclonal antibodies raised against defined internal sequences. Journal of Cellular Biochemistry 84(2): 420–32.
26. Kunicki, T. J., Annis, D. S., and Felding-Habermann B. Molecular determinants of arg-gly-asp ligand specificity for β3 integrins. Journal of Biological Chemistry 272(7): 4103–7, 1997.
27. Lee et al. Transient upregulation of osteopontin mRNA in hippocampus and striatum following global forebrain ischemia in rats. Neurosci Lett. Aug. 20, 1999; 271 (2):81–4.
28. Lipton, S. A., and Rosenberg, P. A. (1994). Excitatory amino acids as a final common pathway for neurologic disorders. N Engl J Med, 330, 613–22.
29. Loius J. C., Magal E., Muir D., Manthorpe M., Varon S. (1992) CG-4 A new bipontial glial cell line from rat brain, is capable of differentiating in vitro into either mature oligodendrocytes or type-2 astrocytes. J Neuroscience Research 31, 193–204.

30. Lubetzki, C., Demerens, C., Anglade, P., Villarroya, H., Frankfurter, A., Lee, M. Y., and Zalc, B. Even in culture, oligodendrocytes myelinate solely axons. Proceedings of the National Academy of Sciences of the USA 90: 6820–4824, 1993.
31. Marchionni, M. A., Cannella, B., Hoban, C., Gao, Y. L., Garcia-Arenas, R., Lawson, D., Happel, E., Noel, F., Tofilon, P., Gwynne, D., and Raine, C. S. Neuregulin in neuron/glial interactions in the central nervous system. GGF2 diminishes autoimmune demyelination, promotes oligodendrocyte progenitor expansion, and enhances remyelination. Advances in Experimental and Medical Biology 468: 283–95, 1999.
32. Mark et al. (Mark D. F. et al., Proc. Natl. Acad. Sci. U.S.A., 81 (18) 5662–5666, 1984)
33. Matthieu, J. M., Comte, V., Tosic, M., and Honegger, P. Myelin gene expression during demyelination and remyelination in aggregating brain cell cultures. Journal of Neuroimmunology 40(2–3): 231–4, 1992.
34. McDonald. J. W., Althomsons, S. P., Hyrc, K. L., Choi, D. W., and Goldberg, M. P. (1998). Oligodendrocytes from forebrain are highly vulnerable to AMPA/kainate receptor-mediated excitotoxicity. Nat Med. 4, 291–7.
35. Morell, P., Barrett, C. V., Mason, J. L., Toews, A. D., Hostettler, J. D., Knapp, G. W., and Matsushima, G. K. Gene expression in brain during Cuprizone-induced demyelination and remyelination. Molecular and Cellular Neurosciences 12(4/5): 220–227, 1998.
36. Nait-Oumesmar, B., Decker, L., Lachapelle, F., Avellana-Adalid, V., Bachelin, C., and Van Evercooren, A. B. Progenitor cells of the adult mouse subventricular zone proliferate, migrate and differentiate into oligodendrocytes after demyelination. European Journal of Neuroscience 11(12):4357–66, 1999.
37. Ng, W. P., Cartel, N., Roder, J., Roach, A., and Lozano, A. Human central nervous system myelin inhibits neurite outgrowth. Brain Research 720(1–2): 17–24, 1996.
38. Noseworthy, J. H. Progress in determining the causes and treatment of multiple sclerosis. Nature 399: A40–A47, 1999.
39. Oldberg et al., Cloning and sequence analysis of rat bone sialoprotein (osteopontin) cDNA reveals an Arg-Gly-Asp cell-binding sequence.Proc Natl Acad Sci U S A. December 1986; 83(23):8819–23.
40. Pantoni, L., Garcia, J. H., and Gutierrez, J. A. (1996). Cerebral white matter is highly vulnerable to ischemia. Stroke, 27, 1641–6.
41. Pearson W R, Methods in Enzymology, 183, 63–99, 1990
42. Pearson W R and Lipman D J, Proc Nat Acad Sci USA, 85, 2444–2448, 1988
43. Petry, K. G., Boullerne, A. I., Pousset, F., Brochet, B., Caille, J. M., and Dousset, V. Experimental allergic encephalomyelitis animal models for analyzing features of multiple sclerosis. Pathol. Biol. (Paris) 48(1): 47–53, 2000.
44. Pohlau, D., Aktas, O., Epplen, C. Hartung, H. P., Hoffmann, V. and Przuntek, H. (1998) Promoting remyelination as a future therapeutic principle in Multiple Sclerosis. Nervenarzt, 69, 841–850.
45. Prineas, J. W., Barnard, R. O., Kwon, E. E., Sharer, L. R., and Cho, E. S. Multiple sclerosis: remyelination of nascent lesions. Annals of Neurology 33(2): 137–51, 1993.
46. Rodriguez-Peña, A. Oligodendrocyte development and thyroid hormone. Journal of Neurobiology 40(4): 497–512, 1999.
47. Rogister, B., Ben-Hur, T., and Dubois-Dalcq, M. From neural stem cells to myelinating oligodendrocytes. Molecular and Cellular Neurosciences 14(4–5): 287–300, 1999.
48. Sahrbacher, U. C., Lechner, F., Eugster, H. P., Frei, K, Lassmann, H., and Fontana, A. Mice with an inactivation of the inducible nitric oxide synthase gene are susceptible to experimental autoimmune encephalomyelitis. European Journal of Immunology 28(4): 1332–8, 1998.
49. Saitoh Y, Kuratsu J, Takeshima H, Yamamoto S, Ushio Y. (1995) Expression of osteopontin in human glioma, correlation with the malignancy. Laboratory Investigations 72(1): 55–63.
50. Scarlato, M., Beesley, J., and Pleasure, D. Analysis of oligodendroglial differentiation using cDNA arrays. Journal of Neuroscience Research 59(3): 430–5, 2000.
51. Scherer, S. S. Molecular genetics of demyelination: new wrinkles on an old membrane. Neuron 18: 13–16, 1997.
52. Scolding, N., and Lassmann, H. Demyelination and remyelination. Trends in Neurosciences 19(1): 1–2, 1996.
53. Shaw, C. E., Milner, R., Compston, A. S., and ffrench-Constant, C. Analysis of integrin expression on oligodendrocytes during axo-glial interaction by using rat-mouse xenocultures. Journal of Neuroscience 16(3): 1163–72, 1996.
54. Shin et al., Expression of osteopontin mRNA in the adult rat brain. Neurosci Lett. Oct. 1, 1999; 273(2):73–6.
55. Shepard H. M. et al., Nature, 294, 563–565, 1981
56. Sodek J, Ganss B, McKee M D, Crit Rev Oral Biol Med 2000;11(3):279–303.
57. Smith, P. K., Krohn, R. I., Hermanson, G. T., Mallia, A. K., Gartner, F. H., Provenzano, M D., Fujimoto, E. K., Goeke, N. M., Olson, B. J. and Klenk, D. C. (1985). Measurement of protein using bicinchoninic acid. Anal. .Biochem.150, 76–85.
58. Smith and Waterman J Mol Biol, 147,195–197, 1981, Advances in Applied Mathematics, 2, 482–489, 1981.
59. Storch, M. K., Piddlesden, S., Haltia, M., Iivanainen, M., Morgan, P., and Lassmann, H. Multiple sclerosis: in situ evidence for antibody- and complement-mediated demyelination. Annals of Neurology 43(4): 465–71, 1998.
60. Trojaborg W (1998) Acute and chronic neuropathies: new aspects of Guillain-Barre syndrome and chronic inflammatory demyelinating polyneuropathy, an overview and an update. Electroencephalogr Clin Neurophysiol., 107, 303–316.
61. Trotter, J., Bitter-Suermann, D., and Schachner, M. Differentiation-regulated loss of the polysialylated embryonic form and expression of the different polypeptides of the neural cell adhesion molecule by cultured oligodendrocytes and myelin. Journal of Neuroscience Research 22(4): 369–83, 1989.
62. Wiechelman, K., Braun, R. and Fitzpatrick, J. (1988). Investigation of the bicinchoninic acid protein assay: Identification of the groups responsible for color formation. Anal.Biochem. 175, 231–237. The degenerated fibers and the normal fibers were counted.
63. Whitney, L. W. Becker, K. G., Tresser, N. J., Caballero-Ramos, C. I., Munson, P. J., Prabhu, V. V., Trent, J. M., McFarland, H. F., and Biddison, W. E. Analysis of gene expression in multiple sclerosis lesions using cDNA microarrays. Annals of Neurology 46(3): 425–8, 1999.

The invention claimed is:

1. A method of treating a neurologic disease, comprising administering to a patient in need thereof a medicament comprising osteopontin, or an agonist of osteopontin activity, optionally together with a pharmaceutically acceptable carrier.

2. The method according to claim 1, wherein the neurologic disease is selected from the group consisting of traumatic nerve injury, stroke, demyelinating diseases of the central or the peripheral nervous system, neuropathies and neurodegenerative diseases.

3. The method according to claim 2, wherein the demyelinating disease is multiple sclerosis (MS).

4. The method of claim 2, wherein the neurodegenerative disease is selected from Alzheimer's disease, Parkinson's disease, Huntington's disease and amyotrophic lateral sclerosis (ALS).

5. The method according to claim 1, wherein the neurologic disease is caused by a congenital metabolic disorder.

6. The method according to claim 1, wherein the neurologic disease is a peripheral neuropathy.

7. The method according to claim 6, wherein the neurologic disease is diabetic neuropathy.

8. The method according to claim 1, wherein the osteopontin is selected from the group consisting of:

(a) a polypeptide comprising SEQ ID NO:1;
(b) a polypeptide comprising amino acids 1 to 168 or 170 of SEQ ID NO: 1;
(c) a polypeptide comprising amino acids 1 to 16 and 170 to 314 of SEQ ID NO:1;
(d) a polypeptide comprising amino acids 170 to 314 of SEQ ID NO:1;
(e) a polypeptide comprising SEQ ID NO:2;
(f) a polypeptide comprising SEQ ID NO:3;
(g) a mutein of any of (a) to (f), wherein the amino acid sequence has at least 40% or 50% or 60% or 70% or 80% or 90% identity to at least one of the sequences in (a) to (f);
(h) a mutein of any of (a) to (f) which is encoded by a DNA sequence which hybridizes to the complement of the native DNA sequence encoding any of (a) to (f);
(i) a mutein of any of (a) to (f) wherein any changes in the amino acid sequence are conservative amino acid substitutions to the amino acid sequences in (a) to (f); and
(j) a salt or an isoform, fused protein, functional derivative, active fraction or circularly permutated derivative of any of (a) to (f).

9. The method according to claim 8, wherein the osteopontin is PEGylated.

10. The method according to claim 1, wherein osteopontin is fused to a carrier molecule, a peptide or a protein that promotes the crossing of the blood brain barrier.

11. The method according to claim 10, wherein the fused protein comprises an immunoglobulin (Ig) fusion.

12. The method according to claim 1, comprising administering further an interferon, simultaneously, sequentially, or separately with respect to said administration of osteopontin or an agonist.

13. The method according to claim 12, wherein the interferon is interferon-β.

14. The method according to claim 1, wherein the osteopontin is administered in an amount of 0.001 to 100 mg/kg of body weight, or 1 to 10 mg/kg of body weight, or 5 mg/kg of body weight.

15. A pharmaceutical composition comprising osteopontin, or an agonist of osteopontin activity, and an interferon, optionally together with one or more pharmaceutically acceptable excipients, in an amount sufficient for treatment and/or prevention of a neurologic disease.

16. A method for treating a neurologic disease comprising administering to a patient in need thereof an effective amount of osteopontin, or of an agonist of osteopontin activity, optionally together with a pharmaceutically acceptable carrier.

17. A method for treating a neurologic disease comprising administering to a patient in need thereof an effective amount of osteopontin, or of an agonist of osteopontin activity, and an interferon, optionally together with a pharmaceutically acceptable carrier.

18. A method for treating a neurologic disease, comprising:
delivering a medicament to an appropriate site of action of the neurologic disease in a patient in need, wherein said medicament comprises osteopontin, or an agonist of osteopontin activity, optionally together with a pharmaceutically acceptable carrier.

19. A method in accordance with claim 18, wherein said delivering step comprises administering said medicament.

* * * * *

SEQUENCE LISTING

<160> NUMBER OF SEQ ID NOS: 5

<210> SEQ ID NO 1
<211> LENGTH: 314
<212> TYPE: PRT
<213> ORGANISM: Homo sapiens

<400> SEQUENCE: 1

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 2
<211> LENGTH: 299
<212> TYPE: PRT
<213> ORGANISM: Homo sapiens

<400> SEQUENCE: 2

```
Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Leu Pro Ser Lys Ser Asn
    50                  55                  60

Glu Ser His Asp His Met Asp Asp Met Asp Asp Glu Asp Asp Asp Asp
65                  70                  75                  80

His Val Asp Ser Gln Asp Ser Ile Asp Ser Asn Asp Ser Asp Asp Val
                85                  90                  95

Asp Asp Thr Asp Asp Ser His Gln Ser Asp Glu Ser His His Ser Asp
            100                 105                 110

Glu Ser Asp Glu Leu Val Thr Asp Phe Pro Thr Asp Leu Pro Ala Thr
            115                 120                 125

Glu Val Phe Thr Pro Val Val Pro Thr Val Asp Thr Tyr Asp Gly Arg
130                 135                 140

Gly Asp Ser Val Val Tyr Gly Leu Arg Ser Lys Ser Lys Lys Phe Arg
145                 150                 155                 160

Arg Pro Asp Ile Gln Tyr Pro Asp Ala Thr Asp Glu Asp Ile Thr Ser
                165                 170                 175

His Met Glu Ser Glu Glu Leu Asn Gly Ala Tyr Lys Ala Ile Pro Val
            180                 185                 190

Ala Gln Asp Leu Asn Ala Pro Ser Asp Trp Asp Ser Arg Gly Lys Asp
        195                 200                 205

Ser Tyr Glu Thr Ser Gln Leu Asp Asp Gln Ser Ala Glu Thr His Ser
    210                 215                 220

His Lys Gln Ser Arg Leu Tyr Lys Arg Lys Ala Asn Asp Glu Ser Asn
225                 230                 235                 240

Glu His Ser Asp Val Ile Asp Ser Gln Glu Leu Ser Lys Val Ser Arg
                245                 250                 255

Glu Phe His Ser His Glu Phe His Ser His Glu Asp Met Leu Val Val
            260                 265                 270

Asp Pro Lys Ser Lys Glu Glu Asp Lys His Leu Lys Phe Arg Ile Ser
        275                 280                 285

His Glu Leu Asp Ser Ala Ser Ser Glu Val Asn
    290                 295

<210> SEQ ID NO 3
<211> LENGTH: 286
<212> TYPE: PRT
<213> ORGANISM: Homo sapiens

<400> SEQUENCE: 3

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Asn Ala
            20                  25                  30

Val Ser Ser Glu Glu Thr Asn Asp Phe Lys Gln Glu Thr Leu Pro Ser
        35                  40                  45

Lys Ser Asn Glu Ser His Asp His Met Asp Asp Met Asp Asp Glu Asp
    50                  55                  60

Asp Asp Asp His Val Asp Ser Gln Asp Ser Ile Asp Ser Asn Asp Ser
```

```
                65                  70                  75                  80
Asp Asp Val Asp Asp Thr Asp Ser His Gln Ser Asp Glu Ser His
                    85                  90                  95

His Ser Asp Glu Ser Asp Glu Leu Val Thr Asp Phe Pro Thr Asp Leu
                    100                 105                 110

Pro Ala Thr Glu Val Phe Thr Pro Val Val Pro Thr Val Asp Thr Tyr
                    115                 120                 125

Asp Gly Arg Gly Asp Ser Val Val Tyr Gly Leu Arg Ser Lys Ser Lys
                    130                 135                 140

Lys Phe Arg Arg Pro Asp Ile Gln Tyr Pro Asp Ala Thr Asp Glu Asp
145                 150                 155                 160

Ile Thr Ser His Met Glu Ser Glu Glu Leu Asn Gly Ala Tyr Lys Ala
                    165                 170                 175

Ile Pro Val Ala Gln Asp Leu Asn Ala Pro Ser Asp Trp Asp Ser Arg
                    180                 185                 190

Gly Lys Asp Ser Tyr Glu Thr Ser Gln Leu Asp Asp Gln Ser Ala Glu
                    195                 200                 205

Thr His Ser His Lys Gln Ser Arg Leu Tyr Lys Arg Lys Ala Asn Asp
210                 215                 220

Glu Ser Asn Glu His Ser Asp Val Ile Asp Ser Gln Glu Leu Ser Lys
225                 230                 235                 240

Val Ser Arg Glu Phe His Ser His Glu Phe His Ser His Glu Asp Met
                    245                 250                 255

Leu Val Val Asp Pro Lys Ser Lys Glu Glu Asp Lys His Leu Lys Phe
                    260                 265                 270

Arg Ile Ser His Glu Leu Asp Ser Ala Ser Ser Glu Val Asn
                    275                 280                 285

<210> SEQ ID NO 4
<211> LENGTH: 22
<212> TYPE: DNA
<213> ORGANISM: homo sapiens

<400> SEQUENCE: 4
agcctgcacc cagatcctat ag                                              22

<210> SEQ ID NO 5
<211> LENGTH: 21
<212> TYPE: DNA
<213> ORGANISM: homo sapiens

<400> SEQUENCE: 5
gcgcaaggag attctgcttc t                                               21
```